United States Patent
Yamato et al.

(10) Patent No.: US 6,673,850 B1
(45) Date of Patent: Jan. 6, 2004

(54) PHOTOINITIATORS AND THEIR APPLICATIONS

(75) Inventors: Hitoshi Yamato, Takarazuka (JP); Masaki Ohwa, Kobe (JP); Toshikage Asakura, Minoo (JP); Akira Matsumoto, Amagasaki (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/959,174

(22) PCT Filed: Apr. 27, 2000

(86) PCT No.: PCT/EP00/03812

§ 371 (c)(1), (2), (4) Date: Oct. 18, 2001

(87) PCT Pub. No.: WO00/68218

PCT Pub. Date: Nov. 16, 2000

(30) Foreign Application Priority Data

May 10, 1999 (EP) .............................. 99810413

(51) Int. Cl.$^7$ .............................. C08F 2/46; C08F 2/50
(52) U.S. Cl. .............................. 522/33; 522/34; 522/35; 522/44; 522/904; 522/153; 522/157; 522/158; 522/178; 522/179; 522/182
(58) Field of Search .............................. 522/33, 34, 35, 522/44, 904, 153, 157, 158, 178, 179, 182

(56) References Cited

U.S. PATENT DOCUMENTS

| | | | | |
|---|---|---|---|---|
| 4,559,371 A | * | 12/1985 | Husler et al. .................. | 522/14 |
| 4,582,862 A | | 4/1986 | Berner et al. .................. | 522/14 |
| 4,672,079 A | * | 6/1987 | Li Bassi et al. ............... | 522/35 |
| 4,739,052 A | * | 4/1988 | Husler et al. ................. | 544/174 |
| 4,946,960 A | * | 8/1990 | Wade et al. .................. | 548/150 |
| 4,977,293 A | * | 12/1990 | Hatton et al. ................. | 558/153 |
| 5,077,402 A | * | 12/1991 | Desobry et al. ............... | 544/87 |
| 5,389,699 A | * | 2/1995 | Rehmer et al. ................ | 522/35 |
| 5,395,903 A | * | 3/1995 | Charmot et al. ............... | 526/220 |
| 5,466,721 A | * | 11/1995 | Share ........................... | 522/34 |
| 5,506,279 A | | 4/1996 | Babu et al. .................... | 522/34 |
| 5,527,925 A | * | 6/1996 | Chabrecek et al. ........... | 549/430 |
| 5,532,112 A | * | 7/1996 | Kohler et al. ................ | 430/281.1 |
| 5,534,629 A | * | 7/1996 | Desobry et al. .............. | 544/78 |
| 5,554,663 A | * | 9/1996 | Desobry et al. .............. | 522/8 |
| 5,621,018 A | * | 4/1997 | Chabrecek et al. ........... | 522/35 |
| 5,629,356 A | * | 5/1997 | Desobry et al. .............. | 522/34 |
| 5,744,512 A | * | 4/1998 | Kohler et al. ................ | 522/34 |
| 5,837,746 A | * | 11/1998 | Kohler et al. ................ | 522/8 |
| 6,022,906 A | * | 2/2000 | Ohwa et al. .................. | 522/8 |
| 6,057,380 A | * | 5/2000 | Birbaum et al. .............. | 522/8 |
| 6,087,412 A | * | 7/2000 | Chabrecek et al. ........... | 522/35 |
| 6,099,122 A | * | 8/2000 | Chabrecek et al. ........... | 351/160 H |
| 6,204,306 B1 | * | 3/2001 | Chabrecek et al. ........... | 523/106 |

FOREIGN PATENT DOCUMENTS

| | | | |
|---|---|---|---|
| EP | 284561 A2 | * 9/1988 | ........... C07C/97/10 |
| EP | 597747 A1 | * 5/1994 | ......... C07C/321/18 |
| EP | 0 911 350 | 4/1999 | |
| GB | 2320027 A | * 6/1998 | ......... C07C/323/29 |
| WO | 96/20919 | 7/1996 | |
| WO | 99/62961 | 12/1999 | |

OTHER PUBLICATIONS

Abst. Page for EP 0 911 350.
Specification for U.S. application No. 09/726,684.
Specification for U.S. application No. 09/701,457.

* cited by examiner

*Primary Examiner*—James J. Seidleck
*Assistant Examiner*—Sanza L McClendon
(74) *Attorney, Agent, or Firm*—David R. Crichton

(57) ABSTRACT

Photoinitiators of formula (Ia) or (Ib) having chain transfer groups, wherein n is 1 or 2; PI is for example a group of formula (IIa); PI' inter alia is a group of formula (IIIa); Ar is for example phenyl; $Ar_2$ is inter alia phenylene; $R_1$ and $R_2$ are for example $C_1$–$C_8$alkyl, or $R_1$ and $R_2$ together $C_2$–$C_9$alkylene; $M_1$ inter alia is —$NR_3R_4$ or —OH; $M_1'$ is for example a group (c); $R_3'$ is a direct bond, $C_1$–$C_{12}$alkylene, or phenylene; $R_3$ is for example hydrogen, or $C_1$–$C_{12}$alkyl; $R_4$ is e.g. $C_1$–$C_{12}$alkyl; $A_1$ and $A_2$ are for example a direct bond; CT is a chain transfer group; are useful for the preparation of macrophotoinitiators which can be employed for preparing block copolymers.

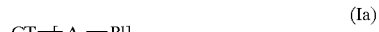

(Ia)

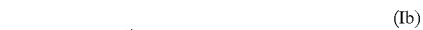

(Ib)

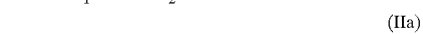

(IIa)

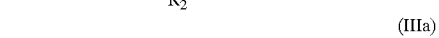

(IIIa)

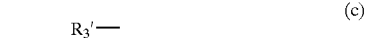

(c)

15 Claims, No Drawings

PHOTOINITIATORS AND THEIR APPLICATIONS

The present application refers to photoinitiator compounds comprising addition fragmentation agent (AFA) type chain transfer groups, macrophotoinitiators, which are obtained by the polymerization of monomers in the presence of photoinitiators with said chain transfer groups and the photopolymerization of said macrophotoinitiators to give block copolymers.

In European Patent Application No. 98810501.1, filed May 29, 1998 photoinitiator compounds comprising SH-substitutents as chain transfer agents are disclosed. Y. Yagci et al in J. Macromol. Sci. Chem., A28(1), pp. 129–141 (1991) describe the use of azo-benzoin compounds as initiators for the preparation of block-copolymers, thermally polymerizing the first monomer with the compounds and then polymerizing the second monomer photochemically. In J. of Polym. Sci., Part A, Polymer Chemistry, Vol. 34, 3471–3484 (1996) and FR-A 2715653 R. Popielarz employs compounds having thermal chain transferring moieties and thermal initiating moieties for the preparation of block-copolymers. Some odorless functional copolymers by using AFA type chain transfer agents are disclosed for examples in WO 88/4304, WO 91/7387, WO 91/7440 and U.S. Pat. No. 5,395,903.

In technique, there still exists a need for reactive, easy to prepare, easy to handle and odorless photoinitiator compounds and there is a need for easy controllable preparation methods for defined block copolymers. By means of photopolymerization with specific macrophotoinitiators such copolymers are obtainable.

Subject of the invention therefore are odorless photoinitiator compounds having chain transfer groups. The compounds comprising chain transfer groups are those of formula Ia or Ib

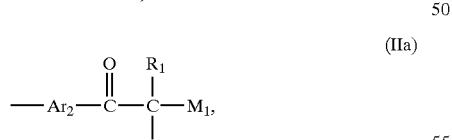

wherein n is 1 or 2;

PI is a group of formula IIa, IIb or IIc

(IIa)

(IIb)

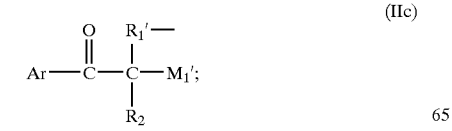

(IIc)

PI' is a group of formula IIIa or IIIb

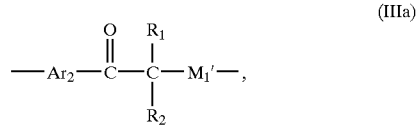

(IIIa)

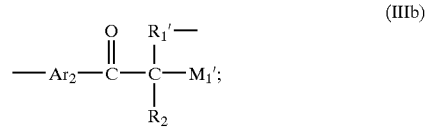

(IIIb)

Ar is phenyl, biphenylyl or benzoylphenyl, each of which is unsubstituted or substituted 1 to 5 times by halogen, $C_1-C_{12}$alkyl, $C_3-C_{12}$alkenyl, $C_5-C_6$cycloalkyl, phenyl-$C_1-C_3$alkyl, —COOH, —COO($C_1-C_4$alkyl), —$OR_7$, —$SR_8$, —$SOR_8$, —$SO_2R_8$, —CN, —$SO_2NH_2$, —$SO_2NH$ ($C_1-C_4$alkyl), —$SO_2$—N($C_1-C_4$alkyl)$_2$, —$NR_9R_{10}$, —$NHCOR_9$, or by a group of formula IV,

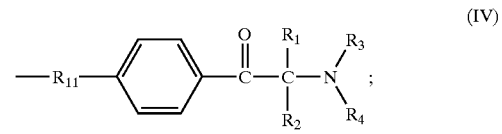

(IV)

or Ar is a group of formula V or VI

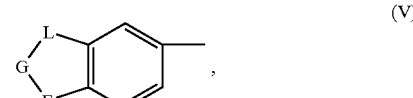

(V)

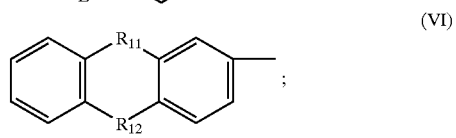

(VI)

$Ar_2$ is

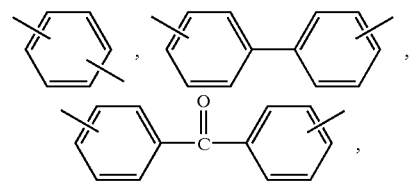

each of which is unsubstituted or substituted 1 to 5 times by halogen, $C_1-C_{12}$alkyl, $C_3-C_{12}$alkenyl, $C_5-C_6$cycloalkyl, phenyl-$C_1-C_3$alkyl, —COOH, —COO($C_1-C_4$alkyl), —$OR_7$, —$SR_8$, —$SOR_8$, —$SO_2R_8$, —CN, —$SO_2NH_2$, —$SO_2NH$ ($C_1-C_4$alkyl), —$SO_2$—N($C_1-C_4$alkyl)$_2$, —$NR_9R_{10}$, —$NHCOR_9$, or by a group of formula IV;

or $Ar_2$ is a group of formula Va or VIa

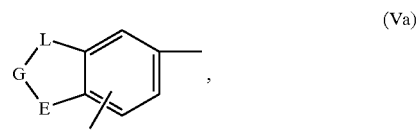

(Va)

-continued

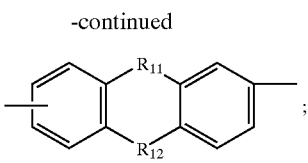
(VIa)

G is unbranched or branched $C_1$-$C_7$alkylene;

L and E independently of one another are a direct bond, 13 O—, —S— or —N($R_6$)—, provided that L and E are not both a direct bond simultaneously;

$R_1$ and $R_2$ independently of one another are $R_7$O—, $C_1$-$C_8$alkyl, which is unsubstituted or substituted by OH, $C_1$-$C_4$alkoxy, $SR_8$, CN, ($C_1$-$C_8$alkyl)O(CO)—, ($C_1$-$C_4$alkyl)—(OC)O— or —N($R_3$)($R_4$), or $R_1$ and $R_2$ independently of one another are $C_3$-$C_6$alkenyl, phenyl, chlorophenyl, $R_7$—O-phenyl, $R_8$—S-phenyl or phenyl-$C_1$-$C_3$-alkyl, or $R_1$ and $R_2$ together are unbranched or branched $C_2$-$C_9$alkylene, $C_3$-$C_9$oxaalkylene or $C_3$-$C_9$azaalkylene, or $R_1$ and $R_2$ independently of one another are a radical of formula VII or VIII

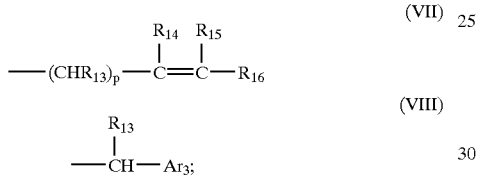
(VII)

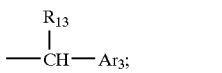
(VIII)

p is 0 or 1;

$Ar_3$ is phenyl, naphthyl, furyl, thienyl or pyridiyl, each of which is unsubstituted or substituted by halogen, SH, OH, $C_1$-$C_{12}$alkyl, OH-substituted $C_1$-$C_4$alkyl, halogen-substituted $C_1$-$C_4$alkyl, SH-substituted $C_1$-$C_4$alkyl, N($R_{17}$)$_2$-substituted $C_1$-$C_4$alkyl, $C_1$-$C_{12}$alkoxy-substituted $C_1$-$C_4$alkyl, ($C_1$-$C_{18}$alkyl)O(OC)-substituted $C_1$-$C_4$alkyl, $CH_3$O($CH_2CH_2O$)$_m$CO-substituted $C_1$-$C_4$alkyl, ($C_1$-$C_4$alkyl)(OC)O-substituted $C_1$-$C_4$alkyl, $C_1$-$C_{12}$alkoxy, ($C_1$-$C_{18}$alkyl)(OC)O-substituted $C_1$-$C_4$alkoxy, $CH_3$O($CH_2CH_2O$)$_m$CO-substituted $C_1$-$C_4$alkoxy, —(OCH$_2$CH$_2$)$_m$OH, —(OCH$_2$CH$_2$)$_m$OCH$_3$, $C_1$-$C_8$alkylthio, phenoxy, —COO ($C_1$-$C_{18}$alkyl), —CO(OCH$_2$CH$_2$)$_m$OCH$_3$, phenyl or benzoyl;

m is 1 to 20;

$M_1$ is —NR$_3$R$_4$ or —OH, or, when $R_1$ and $R_2$ are $R_7$O—, $M_1$ is Ar;

$M_1'$ is a group

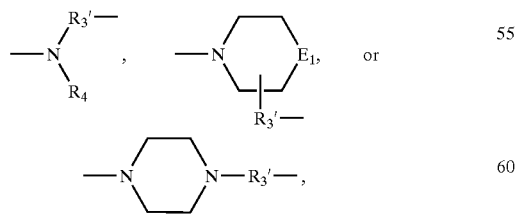

or, when $R_1$ and $R_2$ are $R_7$O—, $M_1'$ is $Ar_2$;

$R_1'$ and $R_3'$ independently of one another are a direct bond, $C_1$-$C_{12}$alkylene, or phenylene;

$E_1$ is —CH$_2$—, —O—, —N($R_6$)— or —S—;

$R_3$ is hydrogen, $C_1$-$C_{12}$alkyl, $C_2$-$C_4$alkyl, which is substituted by OH, SH, $C_1$-$C_4$alkoxy, CN or —COO ($C_1$-$C_4$alkyl); or $R_3$ is $C_3$-$C_5$alkenyl, $C_5$-$C_{12}$-cycloalkyl or phenyl-$C_1$-$C_3$alkyl;

$R_4$ is $C_1$-$C_{12}$alkyl; $C_2$-$C_4$alkyl, which is substituted by OH, SH, $C_1$-$C_4$alkoxy, CN or —COO($C_1$-$C_4$alkyl); or $R_4$ is $C_3$-$C_5$alkenyl, $C_5$-$C_{12}$-cycloalkyl, phenyl-$C_1$-$C_3$alkyl; phenyl which is unsubstituted or substituted by halogen, $C_1$-$C_{12}$alkyl, $C_1$-$C_4$alkoxy or —COO($C_1$-$C_4$alkyl); or $R_4$ together with $R_2$ is $C_1$-$C_7$alkylene, phenyl-$C_1$-$C_4$alkylene, o-xylylene, 2-butenylene, $C_2$-$C_{30}$oxaalkylene or $C_2$-$C_3$azaalkylene;

or $R_3$ and $R_4$ together are $C_3$-$C_7$alkylene, optionally interrupted by —O—, —S—, —CO— or —N($R_6$)— and which $C_3$-$C_7$alkylene is unsubstituted or substituted by OH, SH, $C_1$-$C_4$alkoxy or —COO($C_1$-$C_4$alkyl);

$R_6$ is hydrogen, $C_1$-$C_{12}$alkyl, OH-substituted $C_1$-$C_{12}$alkyl, SH-substituted $C_1$-$C_{12}$alkyl or HS—(CH$_2$)$_n$—COO-substituted $C_1$-$C_{12}$alkyl; $C_2$-$C_{12}$alkyl, which is interrupted by —O—, —NH— or —S—; or $R_6$ is $C_3$-$C_5$alkenyl, phenyl-$C_1$-$C_3$-alkyl, —CH$_2$CH$_2$CN, $C_1$-$C_4$alkyl-CO—CH$_2$CH$_2$—, OH-substituted $C_1$-$C_4$alkyl-CO—CH$_2$CH$_2$—, SH-substituted $C_1$-$C_4$alkyl-CO—CH$_2$CH$_2$—, $C_2$-$C_8$alkanoyl, OH-substituted $C_2$-$C_8$alkanoyl, SH-substituted $C_2$-$C_8$alkanoyl or benzoyl;

$R_7$ is hydrogen, $C_1$-$C_{12}$alkyl, $C_3$-$C_{12}$-alkenyl, cyclohexyl, hydroxycyclohexyl; $C_1$-$C_4$alkyl, which is mono- or polysubstituted by Cl, Br, CN, SH, —N($C_1$-$C_4$alkyl)$_2$, piperidinyl, morpholinyl, OH, $C_1$-$C_4$alkoxy, —OCH$_2$CH$_2$CN, —OCH$_2$CH$_2$COO ($C_1$-$C_4$alkyl), —O(CO)R$_{19}$, —COOH, —COO ($C_1$-$C_8$alkyl), —CONH($C_1$-$C_4$alkyl), —CON ($C_1$-$C_4$alkyl)$_2$,

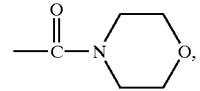

—CO($C_1$-$C_4$alkyl) or by

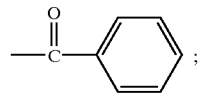

or $R_7$ is 2,3-epoxypropyl, —(CH$_2$CH$_2$O)$_n$H; phenyl which is unsubstituted or substituted by halogen, $C_1$-$C_4$alkyl, $C_1$-$C_4$alkoxy or —COO($C_1$-$C_4$alkyl); or $R_7$ is phenyl-$C_1$-$C_3$-alkyl, tetrahydropyranyl, tetrahydrofuranyl, —COOR$_{19}$, —COO ($C_1$-$C_8$alkyl), —CONH($C_1$-$C_4$alkyl), —CON ($C_1$-$C_8$alkyl)$_2$, —Si(R$_{20}$)(R$_{21}$)$_2$, or —SO$_2$R$_{22}$;

$R_8$ is hydrogen, $C_1$-$C_{12}$alkyl, $C_3$-$C_{12}$alkenyl, cyclohexyl, hydroxycyclohexyl; $C_1$-$C_4$alkyl, which is mono- or polysubstituted by Cl, Br, CN, SH, —N($C_1$-$C_4$alkyl)$_2$, piperidinyl, morpholinyl, OH, $C_1$-$C_4$alkoxy, —OCH$_2$CH$_2$CN, —OCH$_2$CH$_2$COO ($C_1$-$C_4$alkyl), —O(CO)R$_{19}$, —COOH, —COO ($C_1$-$C_8$-alkyl), —CONH($C_1$-$C_4$alkyl)$_2$,

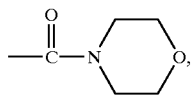

—CO($C_1$–$C_4$alkyl) or

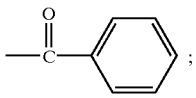

or $R_8$ is 2,3-epoxypropyl, phenyl-$C_1$–$C_3$alkyl, phenyl-$C_1$–$C_3$hydroxyalkyl; phenyl which is unsubstituted or mono- or poly-substituted by halogen, SH, $C_1$–$C_4$alkyl, $C_1$–$C_4$alkoxy or —COO($C_1$–$C_4$alkyl); or $R_8$ is 2-benzothiazyl, 2-benzimidazolyl, —$CH_2CH_2$—O—$CH_2CH_2$—SH or —$CH_2CH_2$—S—$CH_2CH_2$—SH;

$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or poly-substituted by $C_1$–$C_{12}$alkyl or halogen; or $R_9$ and $R_{10}$ together are $C_2$–$C_7$alkylene, optionally interrupted by —O—, —S—, —CO— or —N($R_6$)—;

$R_{11}$ and $R_{12}$ independently of one another are a direct bond, —$CH_2$—, —$CH_2CH_2$—, —O—, —S—, —CO— or —N($R_6$)—; provided that $R_{11}$ and $R_{12}$ are not a direct bond simultaneously;

$R_{13}$ is hydrogen, $C_1$–$C_8$alkyl or phenyl;

$R_{14}$, $R_{15}$ and $R_{16}$ independently of one another are hydrogen or $C_1$–$C_4$alkyl;

$R_{17}$ is hydrogen, $C_1$–$C_8$alkyl or phenyl;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl; or phenyl which is unsubstituted or substituted by $C_1$–$C_{14}$alkyl;

$A_1$ and $A_2$ independently of one another are a direct bond, —X[($CH_2$)$_l$X']$_q$—[($C_6H_4$)$_o$X"]$_r$—, —O—, —S— or —N($R_6$)—;

X, X' and X" independently of each other are a direct bond, —O—, —S—, —N($R_6$)—, —O(CO)—, —COO— —NHCO—, —CONH— or —CO—;

l is an integer from 0 to 10;

q is an integer from 0 to 5:

o and r independently of one another are an integer 0, 1 or 2;

CT when n is 1, is a group of formula IXa, IXb, Xa or Xb,

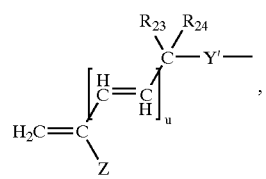

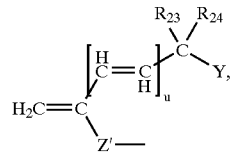

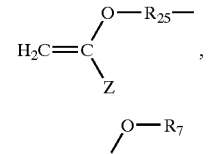

or, when n is 2, CT is a group of formula XI and XII,

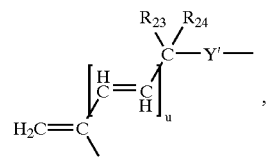

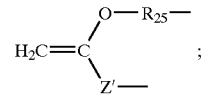

Y is —W($R_8$)$_s$;

Y' is —W($R_8$)$_t$13 $R_{25}$—;

W is S, Si, Se, P, Br, Cl, Sn, —O—O—, S(=O), S(=O)$_2$, or P(=O);

Z is —COO$R_7$, —CONR$_9R_{10}$, —CN, or —Ar;

Z' is —COO$R_{25}$—, —CONR$_9R_{25}$—, or —Ar$_2$—;

s is an integer from 0 to 3;

t is an integer 0, 1 or 2;

u is 0 or 1;

$R_{23}$ and $R_{24}$ independently of one another are hydrogen, or $C_1$–$C_8$alkyl; or $R_{23}$ and $R_{24}$ together are $C_5$–$C_7$cyloalkyl; and $R_{25}$ is a direct bond, $C_1$–$C_4$alkylene or phenylene.

The following explanations refer to the whole context of the application.

$C_1$–$C_{18}$alkyl is linear or branched and is, for example, $C_1$–$C_{14}$-, $C_1$–$C_{12}$-, $C_1$–$C_8$-, $C_1$–$C_6$- or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl and octadecyl.

$C_1$–$C_{14}$alkyl, $C_1$–$C_{12}$alkyl, $C_1$–$C_8$alkyl, $C_1$–$C_6$alkyl and $C_1$–$C_4$alkyl have the same meanings as given above for $C_1$–$C_{20}$alkyl up to the corresponding number of C-atoms.

Mono- or polysubstituted $C_1$–$C_4$alkyl is substituted 1 to 6 times, for example 1 to 4 times, especially once or twice.

$C_2$–$C_{12}$alkyl interrupted by 1 to 9, 1–5, 1–3 or 1 or 2 —O—, —N($R_6$)—, —S—, —C(O)—, produces, for example structural units such as —$CH_2$—O—$CH_2$—, —$CH_2$—S—$CH_2$—, —$CH_2$—N($CH_3$)—$CH_2$—, —$CH_2CH_2$—O—$CH_2CH_2$—, —[$CH_2CH_2$O]$_y$—, —[$CH_2CH_2$O]$_y$—$CH_2$—, where y = 1–5, —($CH_2CH_2$O)$_5$$CH_2CH_2$—, —$CH_2$—CH($CH_3$)—O—$CH_2$—CH($CH_3$)— or —$CH_2$—CH($CH_3$)—O—$CH_2$—$CH_2CH_2$—. Also the interrupted $C_2$–$C_{12}$alkyl is linear or branched.

$C_2$–$C_{12}$alkylene is linear or branched alkylene, for example $C_1$–$C_9$alkylene, $C_1$–$C_7$alkylene, $C_1$–$C_6$alkylene, $C_1$–$C_4$alkylene, namely methylene, ethylene, propylene, 1-methylethylene 1,1-dimethyl-ethylene, 2,2-dimethylpropylene, butylene, 1-methylbutylene, 1-methylpropylene, 2-methyl-propylene, pentylene, hexylene, heptylene, octylene, nonylene, decylene, dodecylene, tetradecylene or hexadecylene.

$C_1$–$C_9$alkylene, $C_1$–$C_7$alkylene and $C_1$–$C_6$alkylene have the same meanings as given above for $C_2$–$C_{16}$alkylene up to the corresponding number of C-atoms.

If $R_1$ and $R_2$ together are $C_2$–$C_9$alkylene, together with the C-atom to which they are bound for example propyl, pentyl, hexyl, octyl or decyl rings are produced. If $R_1$ and $R_2$ together are $C_3$–$C_9$oxaalkylene or $C_3$–$C_9$azaalkylene, said rings are interrupted by O or N atoms. Thus, they are, for example piperidine, azolidine, oxolane or oxane rings If $R_3$ and $R_4$ together are $C_3$–$C_7$alkylene, optionally interrupted by —O—, —S—, —CO— or —N($R_6$)—, together with the N-atom to which they are bound, for example morpholino or piperidino groups are formed.

If $R_9$ and $R_{10}$ together are $C_2$–$C_7$alkylene, optionally interrupted by —O—, —S—, —CO— or —N($R_6$)—, together with the N-atom to which they are bound, for example morpholino or piperidino groups are formed.

$C_3$–$C_{12}$alkenyl, for example $C_3$–$C_6$alkenyl or $C_3$–$C_5$alkenyl radicals may be mono or polyunsaturated and may be linear or branched and are for example allyl, methallyl, 1,1-dimethylallyl, 1-butenyl, 3-butenyl, 2-butenyl, 1,3-pentadienyl, 5-hexenyl or 7-octenyl, especially allyl. $C_3$–$C_6$alkenyl, $C_3$–$C_5$alkenyl and $C_2$–$C_4$alkenyl have the same meanings as given above for $C_3$–$C_{12}$alkenyl up to the corresponding number of C-atoms.

$C_2$–$C_8$alkanoyl is for example $C_2$–$C_6$-, $C_2$–$C_4$- or $C_2$–$C_3$alkanoyl. These radicals are linear branched and are for example ethanoyl, propanoyl, 2-methylpropanoyl, hexanoyl or octanoyl. $C_2$–$C_3$alkanoyl has the same meanings as given for $C_2$–$C_8$alkanoyl up to the corresponding number of C-atoms.

$C_3$–$C_8$cycloalkyl, $C_5$–$C_{12}$cycloalkyl are for example $C_5$–$C_8$- or $C_5$–$C_6$cycloalkyl, namely cyclopropyl, cyclobutyl, cyclopentyl, cyclohexyl, cyclooctyl, cyclododecyl, especially cyclopentyl and cyclohexyl, preferably cyclohexyl. $C_5$–$C_6$cycloalkyl is cyclopentyl or cyclohexyl.

$C_4$–$C_8$cycloalkenyl is, for example, $C_5$–$C_6$cycloalkenyl. Examples are cyclobutenyl, cyclopentenyl, cyclohexenyl, cycloheptenyl, or cyclooctenyl, especially cyclopentenyl or cyclohexenyl.

$C_1$–$C_{12}$alkoxy, is for example $C_1$–$C_8$alkoxy, especially $C_1$–$C_4$alkoxy, and is a linear or branched radical, for example, methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy or tert-butyloxy, preferably methoxy.

$C_1$–$C_8$alkoxy and $C_1$–$C_4$alkoxy have the same meanings as given for $C_1$–$C_{12}$alkoxy up to the corresponding number of C-atoms.

$C_1$–$C_8$alkylthio, for example $C_1$–$C_6$- or $C_1$–$C_4$alkylthio is linear or branched and is, for example methylthio, ethylthio, n-propylthio, i-propylthio, n-butylthio, i-butylthio, s-butylthio, t-butylthio, pentylthio, hexylthio or octylthio, preferably methylthio or butylthio.

Phenyl-$C_1$–$C_3$-alkyl is for example benzyl, phenylethyl, a-methylbenzyl or α,α-dimethylbenzyl, especially benzyl.

Substituted phenyl-$C_1$–$C_3$alkyl is substituted one to four times, for example once, twice or three times, especially twice or three times, on the phenyl ring.

Substituted phenyl is substituted one to four times, for example once, twice or three times, especially once or twice. Substituents are, for example in position 2, 3, 4, 5 or 6, especially in position 2, 6 or 3 of the phenyl ring.

Mono- or polysubstituted phenyl is substituted one to four times, for example once, twice or three times, especially once or twice.

Halogen is fluorine, chlorine, bromine and iodine, especially fluorine, chlorine and bromine, preferably bromine and chlorine.

Examples for Ar being a group of formula V are

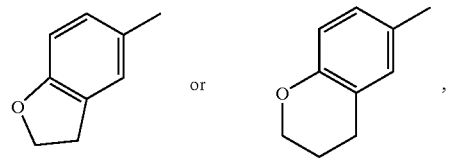

wherein L is O,
G is $C_2$- or $C_3$alkylene and E is a direct bond.

AFA type chain transfer group-containing photoinitiator compounds are obtained, for instance, by reacting thiol-containing photoinitiators and AFA type chain transfer agents. AFA type chain transfer agents are disclosed, for example, in WO 88/04304 and U.S. Pat. No. 5,395,903.

More specifically, AFA type of chain transfer group-containing photoinitiators can be prepared by treating thiol-containing photoinitiators with monomers, for example, methyl 2-(bromomethyl)acrylate, 2-(bromomethyl)acrylic acid, ethyl 1,3-dibromopropane-2-carboxylate, 1,3-dibromopropane-2-carboxylic acid, or -(bromomethyl) styrene.

These reactions are carried out in a solvent such as methanol, ethanol, dichloromethane, tetrahydrofuran (THF) or dimethylformamide (DMF) in the presence of a base, for example potassium carbonate, potassium hydrogen carbonate, sodium carbonate, sodium hydroxide, or triethylamine, and generally are carried out at a temperature of −20° C. to 80° C., preferably 0° C. to 40° C. These methods are known to the person skilled in the art and described, for example, in Macromolecules 24, 3689–3695 (1991).

Another preparation method is, for example, the condensation of hydroxy group or amine group containing photoinitiators with the corresponding acrylic acid (e.g. 2-(butylmercaptomethyl)acrylic acid, 2-(bromomethyl) acrylic acid etc.) using condensation reagents such as 1,3-dicyclohexylcarbodiimide (hereinafter called "DCC").

These reactions for example are carried out in a solvent such as dichloromethane, THF, DMF, chloroform, or toluene at a temperature of −20° C. to 50° C., preferably 0° C. to 30° C. These methods are described, for example, in Can. J. Chem., 66, 1701–1705 (1988).

The preparation of thiol-containing photoinitiators, which are used as starting materials to prepare the compounds of the present invention is known and for example described in U.S. Pat. No. 5,077,402 and GB 2320027. These thiol-containing photoinitiator compounds can, for example, be prepared from halophenyl aliphatic ketones by treatment with an excess of the corresponding dithiol or polythiol. Thiol compounds can for example also be obtained from the corresponding vinyl, hydroxy, halogen or amino precursors by known methods. See, for example "The Chemistry of the Thiol Group", ed. S. Patai, John Wiley & Sons, p. 163, New York, 1974. Further, hydroxy groups can be transformed to thiol groups by the reaction with hydrogen sulfide or phosphorous pentasulfides, or via the corresponding halogens. The esterification of alcohols with a mercaptocarboxylic acid, such as mercaptoacetic acid or mercaptopropionic acid provides another convenient access to thiols. Amines can be converted to thiols by alkylation with mercapto halides or by amidation with a mercaptocarboxylic acid, such as mercaptoacetic acid or mercaptopropionic acid. The performance of such reactions and the reaction conditions for such reactions are generally known to the person skilled in the art.

Preference is given to compounds of formula Ia, wherein when n is 1, CT is a group of formula IXa or IXb and when n is 2, CT is a group of formula XI.

Other preferred compounds are such, wherein PI is a group of formula IIa;

$Ar_2$ is

[structure: phenyl ring]

which is unsubstituted or substituted 1 to 4 times by halogen, $C_1$–$C_{12}$alkyl, or —$OR_7$;

$R_1$ and $R_2$ independently of one another are $C_1$–$C_8$alkyl, which is unsubstituted or substituted by OH, or $C_1$–$C_4$alkoxy, or $R_1$ and $R_2$ independently of one another are $C_3$–$C_6$alkenyl, phenyl, chlorophenyl, or phenyl-$C_1$–$C_3$-alkyl, or $R_1$ and $R_2$ independently of one another are a radical of formula VII or VIII;

$Ar_3$ is phenyl;

$M_1$ is —$NR_3R_4$;

$R_3$ is hydrogen, $C_1$–$C_{12}$alkyl; or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl; or $R_3$ and $R_4$ together are $C_3$–$C_7$alkylene, optionally interrupted by —O—;

$R_7$ is hydrogen, or $C_1$–$C_{12}$alkyl;

$R_{13}$, $R_{14}$, $R_{15}$ and $R_{16}$ are hydrogen;

$A_1$ is a direct bond, —X[($CH_2$)$_l$X']$_q$—[($C_6H_4$)$_o$X"]$_r$—, —O—, —S— or —N($R_6$)—;

$R_6$ is hydrogen or $C_1$–$C_{12}$alkyl;

X, X' and X" independently of each other are a direct bond, —O—, —S—, or —N($R_6$)—;

l is an integer from 0 to 4;

q is an integer 0 or 1;

CT when n is 1, is a group of formula IXa or IXb or, when n is 2, CT is a group of formula XI, Y is —W($R_8$)$_s$;

Y' is —W($R_8$)$_t$$R_{25}$—;

W is S;

$R_8$ is hydrogen or $C_1$–$C_{12}$alkyl;

Z is —$COOR_7$, —$CONR_9R_{10}$, or —Ar;

$R_9$ and $R_{10}$ independently of each other are hydrogen or $C_1$–$C_{12}$alkyl;

Ar is phenyl;

Z' is —$COOR_{25}$— or —$CONR_9R_{25}$—;

u and t are 0;

s is 1;

$R_{23}$ and $R_{24}$ are hydrogen; and $R_{25}$ is a direct bond or $C_1$–$C_4$alkylene.

The photoinitiator compounds of formula Ia and Ib according to the invention can be used as chain transfer agents.

The macrophotoinitiators are obtained by thermally polymerizing a monomer and the above defined photoinitiator compound comprising an AFA type chain transfer group. Another object of the invention is a macrophotoinitiator obtained by thermally polymerizing a monomer and a photoinitiator compound of formula Ia or Ib.

Suitable monomers to prepare the macrophotoinitiators according to the invention are of formula XIII $$Y_2\text{—}\underset{\underset{Y_1}{|}}{C}\text{=}\underset{\underset{Y_3}{|}}{C}\text{—}X_1, \quad \text{(XIII)}$$

wherein $X_1$ is —CN, —OSi($R_{26}$)$_3$, —$R_{27}$, —$OR_{28}$, —$SR_{28}$, —$NR_{29}R_{30}$,

[structures showing: —C(H)=C(H)—$X_2$, —C($X_2$)=C(H)—H, —C(H)=C(H)—C(=O)—$X_2$, —C(=O)—$X_2$;]

or $X_1$ is phenyl or benzyl each of which is unsubstituted or substituted by halogen, $C_1$–$C_{12}$alkyl, $C_1$–$C_{12}$alkoxy, $C_3$–$C_8$cycloalkyl, —COOH, —COO($C_1$–$C_{12}$alkyl), —O(CO)O($C_1$–$C_{12}$alkyl), tetrahydropyranyloxy, tetrahydrofuranyloxy, or tetrahydrofurfuryloxy;

$Y_1$, $Y_2$ and $Y_3$ independently of one another are hydrogen, $C_1$–$C_4$alkyl, halogen, —CN or —$COOR_7$; or $Y_1$ and $Y_3$ together are $C_3$–$C_7$alkylene, optionally interrupted by —O—, —S—, —CO— or —N($R_6$)— and which $C_3$–$C_7$alkylene is unsubstituted or substituted by OH, $C_1$–$C_4$alkoxy or —COO($C_1$–$C_4$alkyl);

$X_2$ is —OSi($R_{26}$)$_3$, —$R_{27}$, —$OR_{28}$, —$SR_{28}$, —$NR_{29}R_{30}$;

$R_{26}$ independently of one another are hydrogen; $C_1$–$C_{20}$alkyl, $C_3$–$C_{12}$-alkenyl, $C_3$–$C_8$cycloalkyl, $C_4$–$C_8$cycloalkenyl, each of which is unsubstituted or mono- or polysubstituted by F, Cl, Br, CN, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —O(CO)$R_{19}$, —COOH, —COO($C_1$–$C_8$alkyl), —CONH($C_1$–$C_4$alkyl), —CON($C_1$–$C_4$alkyl)$_2$, —CO($C_1$–$C_4$alkyl) or by

[structure: —C(=O)—phenyl]

or $R_{26}$ is 2,3-epoxypropyl, —(CH$_2$CH$_2$O)$_m$H or —(CH$_2$CH$_2$O)$_m$R$_{19}$;

or $R_{26}$ is phenyl, pyridinyl, biphenylyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, or —COO($C_1$–$C_{12}$alkyl); or $R_{26}$ is phenyl-$C_1$–$C_3$alkyl, $OR_7$, —$NR_9R_{10}$, or —NHCOR$_9$;

$R_{27}$ is hydrogen; $C_1$–$C_{20}$alkyl, $C_3$–$C_{12}$-alkenyl, $C_3$–$C_8$cycloalkyl, $C_4$–$C_8$ cycloalkenyl each of which is unsubstituted or mono- or polysubstituted by F, Cl, Br, CN, —N($C_1$–$C_4$alkyl)$_2$, phenyl, phenoxy, piperidino, morpholino, OH, $C_1$–$C_4$alkoxy, —$OCH_2CH_2CN$, —$OCH_2CH_2COO(C_1$–$C_4$alkyl), —$O(CO)R_{19}$, —COOH, —$COO(C_1$–$C_8$alkyl), —CONH($C_1$–$C_4$alkyl), —$CON(C_1$–$C_4$alkyl)_2$, —CO($C_1$–$C_4$alkyl) or by

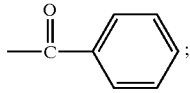

or $R_{27}$ is 2,3-epoxypropyl, or —$(CH_2CH_2O)_mH$;
or $R_{27}$ is phenyl, pyridinyl, biphenylyl, benzyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, —$COO(C_1$–$C_{12}$alkyl), —$O(CO)O(C_1$–$C_{12}$alkyl)$, tetrahydropyranyloxy, tetrahydrofuranyloxy, or tetrahydrofurfuryloxy;
or $R_{27}$ is phenyl-$C_1$–$C_3$alkyl, tetrahydropyranyl, tetrahydrofuranyl, adamantyl, camphoryl; and optionally $R_{27}$ contains one or more reactive substituents of formula

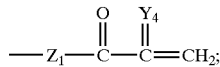

$R_{28}$ is hydrogen; $C_1$–$C_{20}$alkyl, $C_3$–$C_{12}$-alkenyl, $C_3$–$C_8$cycloalkyl, $C_4$–$C_8$cycloalkenyl each of which is unsubstituted or mono- or polysubstituted by F, Cl, Br, CN, —$N(C_1$–$C_4$alkyl)_2$, phenyl, phenoxy, piperidino, morpholino, OH, $C_1$–$C_4$alkoxy, —$OCH_2CH_2CN$, —$OCH_2CH_2COO(C_1$–$C_4$alkyl), —$O(CO)R_{19}$, —COOH, —$COO(C_1$–$C_8$alkyl), —CONH($C_1$–$C_4$alkyl), —$CON(C_1$–$C_4$alkyl)_2$, —CO($C_1$–$C_4$alkyl) or by

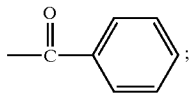

or $R_{28}$ is 2,3-epoxypropyl, or —$(CH_2CH_2O)_mH$;
or $R_{28}$ is phenyl, pyridinyl, biphenylyl, benzyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, —$COO(C_1$–$C_{12}$alkyl), —$O(CO)O(C_1$–$C_{12}$alkyl)$, tetrahydropyranyloxy, tetrahydrofuranyloxy, or tetrahydrofurfuryloxy;
or $R_{28}$ is phenyl-$C_1$–$C_3$alkyl, tetrahydropyranyl, tetrahydrofuranyl, adamantyl, camphoryl; and optionally $R_{28}$ contains one or more reactive substituents of formula

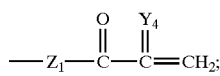

$R_{29}$ and $R_{30}$ independently of one another are hydrogen; $C_1$–$C_{12}$alkyl, or $C_2$–$C_4$alkyl each of which is substituted by OH, $C_1$–$C_4$alkoxy, CN or —COO($C_1$–$C_4$alkyl);
or $R_{29}$ and $R_{30}$ independently of one another are $C_3$–$C_5$alkenyl, cyclohexyl, phenyl-$C_1$–$C_3$alkyl, adamantyl, camphoryl unsubstituted phenyl or phenyl which is mono- or poly-substituted by $C_1$–$C_{12}$alkyl or halogen;
or $R_{29}$ and $R_{30}$ together are $C_2$–$C_7$alkylene optionally interrupted by —O—, —S— or —N($R_6$)—;
$Y_4$ is hydrogen or $CH_3$;
$Z_1$ is —O— or —N($R_{28}$)—;
$R_6$ is hydrogen, $C_1$–$C_{12}$alkyl, OH-substituted $C_1$–$C_{12}$alkyl, SH-substituted $C_1$–$C_{12}$alkyl or HS—$(CH_2)_n$—COO-substituted $C_1$–$C_{12}$alkyl; $C_2$–$C_{12}$alkyl, which is interrupted by —O—, —NH— or —S—; or $R_6$ is $C_3$–$C_5$alkenyl, phenyl-$C_1$–$C_3$-alkyl, —$CH_2CH_2CN$, $C_1$–$C_4$alkyl-CO—$CH_2CH_2$—, OH-substituted $C_1$–$C_4$alkyl-CO—$CH_2CH_2$—, SH-substituted $C_2$–$C_4$alkyl-CO—$CH_2CH_2$—, $C_2$–$C_8$alkanoyl, OH-substituted $C_2$–$C_8$alkanoyl, SH-substituted $C_2$–$C_8$alkanoyl or benzoyl; and n is 1 or 2.

Accordingly, a subject of the invention is a macrophotoinitiator, wherein the monomer is of formula (XIII).

A preferred macrophotoinitiator is of formula XIII, wherein
$X_1$ is —CN, or

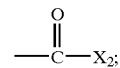

or $X_1$ is phenyl or benzyl each of which is unsubstituted or substituted by halogen, $C_1$–$C_{12}$alkyl, $C_1$–$C_{12}$alkoxy, $C_3$–$C_8$cycloalkyl, —COOH, —$COO(C_1$–$C_{12}$alkyl), —$O(CO)O(C_1$–$C_{12}$alkyl)$, tetrahydropyranyloxy, tetrahydrofuranyloxy, or tetrahydrofurfuryloxy;
$Y_1$ and $Y_2$ are hydrogen;
$Y_3$ is hydrogen or $C_1$–$C_4$ alkyl;
$X_2$ is —$OR_{28}$ or —$NR_{29}R_{30}$.

Suitable monomers are hydrophilic, amphiphilic or hydrophobic.

Examples of hydrophilic monomers are (meth)acrylamide, N,N-dimethyl(meth)acrylamide, N-isopropenyl(meth)acrylamide, N-vinylformamide, (meth)acrylic acid, crotonic acid, itaconic acid, cinnamic acid, 2-hydroxyethyl(meth)acrylate, 2-hydroxypropyl(meth)acrylate, maleic acid, maleic acid anhydride, n-(1,1-dimethyl 3-oxobutyl)(meth)acrylate, 4-hydroxystyrene, 4-hydroxymethyl styrene, p-1-(2-hydroxybutyl)styrene, p-1-(2-hydroxypropyl)styrene, p-2-(2-hydroxypropyl)styrene and styrene sulfonic acid.

Examples of amphiphilic monomers or oligomers are (meth)acrylonitrile, N-(meth)acrylmorpholine, N-vinylpyrrolidone, N-vinylacetamide, N-vinyl-N-methylacetamide, vinyl methyl ether. Polyethylene glycol mono-(meth)acrylate, methoxy poly(ethylene glycol)mono-(meth)acrylate, poly(propylene glycol)mono-(meth)acrylate. N-vinylcaprolactam, N-vinylcarbazole, 4-vinylbenzyl tetrahydrofurfuryl ether and glycidyl(meth)acrylate.

Examples of hydrophobic monomers are methyl(meth)acrylate, ethyl(meth)acrylate, n-butyl(meth)acrylate, tert-butyl(meth)acrylate, 2-ethylhexyl(meth)acrylate, isobornyl(meth)acrylate, lauryl(meth)acrylate, stearyl(meth)acrylate, 1-naphtyl(meth)acrylate, 2-naphtyl(meth)acrylate, adamantyl(meth)acrylate, styrene, 2,4,6-trimethystyrene, 2,5-dichlorostyrene, α-methoxystyrene, α-methylstyrene, 3-methylstyrene, 4-methylstyrene, 3-nitrostyrene, 4-chloromethylstyrene, 4-aminostyrene, 4-tert-butylstyrene, 4-tert-butoxycarbonyloxystyrene, 3-bromostyrene, 4-bromostyrene, 2-chlorostyrene, 3-chlorostyrene, 4-chlorostyrene, 4-cyanostyrene, 4-cyclohexylstyrene, dimethylaminomethyl-styrene, pentachlorostyrene, 4-iodostyrene, β-methoxystyrene, 2-methoxystyrene, 4-methoxystyrene, 1- vinylnaphtalene, 2-vinylnaphtalene, vinyl acetate, vinyl propionate, isobutyl vinyl ether, vinyl chloride, 4-vinylbenzyl chloride, 2-fluoroethyl(meth) acrylate, perfluorocyclohexyl(meth)acrylate, perfluorooctyl (meth)acrylate, 2,2,3,3-tetrafluoropropyl(meth)acrylate, 2,2, 2-trifluoroethyl(meth)acrylate and 3-(trifluoromethyl) benzyl(meth)acrylate.

The monomers can be used alone or in any desired mixtures.

Preferred monomers are selected from the group consisting of acrylates, methacrylates and styrene derivatives.

The macrophotoinitiators according to the present invention are prepared, by thermally polymerizing a monomer with a photoinitiator having a chain tranfer group as defined above. The person skilled in the art generally knows how to conduct a thermal polymerization.

Generally, thermal initiators can be employed, for instance azobisisobutyronitrile (AIBN), N-acetyl N'-α-cyanoethyl diimide, 2-cyano-2-propyl-azo-formamide, N-acetyl N'-α-cyanocyclopentyl diimide, 3,6-dicyano-3,6-dimethyl-1,2-diazocyclo-1-pentane, N-acetyl N'-α-cyanocycloheptyl diimide, phenyl-azo-triphenylmethane, 4-nitrophenyl-azo-triphenylmethane, 4-methoxyphenyl-azo-2-(methylpropanedinitrile), benzoyl peroxide, methyl ethyl ketone peroxide, t-butyl peroxybenzoate or t-butylperoxy-2-ethyl hexanoate. These compounds usually are added in a concentration from 0.005 mol % to 5 mol %, based on the monomer, preferably in a concentration from 0.05 mol % to 1 mol %.

The photoinitiator having a chain transferring moiety can be combined in any ratio with the monomers to control the molecular weight of the obtained polymer. The molar ratio of photoinitiator:monomer is for example in the range from 1:100,000 to 1:1; preferably from 1:50,000 to 1:1.

The polymerization usually is carried out in bulk or in any solution at any concentration. Examples of suitable solvents are hydrocarbons such as benzene, toluene, xylene, cyclohexane; esters such as ethyl acetate, butyl acetate, amyl acetate; ketones such as acetone, methyl ethyl ketone, methyl isobutyl ketone, cyclohexanone; ethers such as tetrahydrofuran and 1,4-dioxane; alcohols such as methanol, ethanol, isobutyl alcohol 1,2,6-hexanetriol glycerin; amides such as N,N-dimethylformamide, N-methylformamide, N,N-diethylformamide, N-methylacetamide, N,N-dimethylacetamide, N-methylpropionamide; pyrrolidones such as 1-methyl-2-pyrrolidone, pyrrolidone ε-caprolactam; glycols such as ethylene glycol, propylene glycol, butylene glycol, tri(methylene glycol), tri(ethylene glycol), hexylene glycol, di(ethylene glycol), diethylene glycol, di(propylene glycol), poly(ethylene glycol); glycol ethers such as 2-methoxyethanol, 2-ethoxyethanol, 2-(2-methoxy)ethoxy ethanol, 2-propoxyethanol, 2-butoxyethanol, di(ethylene glycol)monomethyl ether, di(ethylene glycol)monoethyl ether, di(ethylene glycol)monobutyl ether, tri(ethylene glycol)monoethyl ether, 1-methoxy-2-propanol, 1-ethoxy-2-propanol, di(propylene glycol)monomethyl ether, di(propylene glycol)monoethyl ether, tri(propylene glycol) monomethyl ether, 3-methoxyl-3-methyl-1-butanol; halogenated hydrocarbon, such as chloroform or methylene chloride. The solvent may also be in the form of a mixture of two or more of the above-mentioned solvents.

The polymerization generally is carried out in inert atmosphere in order to avoid inactivation of the generated radicals. Examples of suitable inert gases are nitrogen, helium, neon, argon and xenon.

The polymerization usually is conducted at an appropriate temperature at which the monomers can be polymerized. The temperature strongly depends on the choice of the monomer, initiator and solvent. The temperature generally is in the range from 40° C. to 180° C., preferably from 60° C. to 130° C.

The number and weight average molecular weights of the obtained macrophotoinitiator expediently is determined by a common method such as for example (gel permeation chromatography) GPC measurement, calibrated by the standard polystyrene or/and poly(methyl methacrylate). The number and weight average molecular weights of the obtained macrophotoinitiator are in the range from 300 to 10,000,000, preferably from 500 to 1,000,000.

Accordingly, a process for the preparation of a macrophotoinitiator, characterized in that a photoinitiator with a chain transfer group as described above is thermally polymerized with a monomer is another subject of the invention.

The invention also pertains to a macrophotoinintiator, which is obtained by reacting a photoinitiator of formula Ia or Ib, as defined above with a monomer of formula XII.

Preferably the macrophotoinintiator is of formula XIV

wherein n is 1 or 2;

PI is a photoinitiator moiety $CT_1$ is —Y'—, $R_{25}$—,

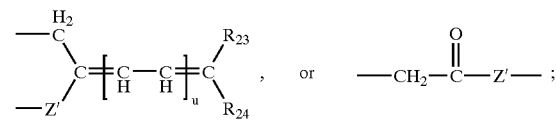

u is 0 or 1;

J is a polymeric group;

$A_1$ is a direct bond, —X[$(CH_2)_l$X']$_q$—[$(C_6H_4)_o$X"]$_r$—, —O—, —S— or —N($R_6$)—;

X, X' and X" independently of each other are a direct bond, —O—, —S—, —N($R_6$)—, —O(CO)—, —COO— —NHCO—, —CONH— or —CO—;

l is an integer from 0 to 10;

q is an integer from 0 to 5;

o and r independently of one another are an integer 0, 1 or 2;

Z' is —COO$R_{25}$—, —CONR$_9$R$_{25}$—, or —Ar$_2$—;

Y' is —W(R$_8$)$_t$—R$_{25}$—;

t is an integer 0, 1 or 2;

W is S, Si, Se, P, Br, Cl, Sn, —O—O—, S(=O), S(=O)$_2$, or P(=O);

$Ar_2$ is

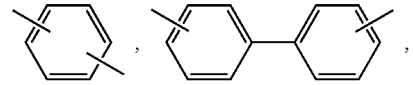

-continued

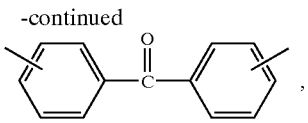

each of which is unsubstituted or substituted 1 to 5 times by halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SR$_8$, —SOR$_8$, —SR$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of formula IV

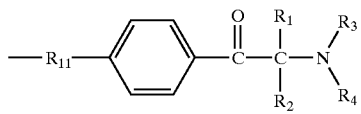 (IV);

or Ar$_2$ is a group of formula Va or VIa

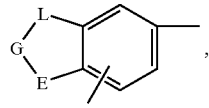 (Va)

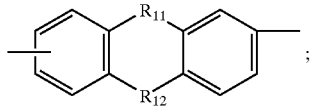 (VIa)

G is unbranched or branched $C_1$–$C_7$alkylene;
L and E independently of one another are a direct bond, —O—, —S— or —N(R$_6$)—, provided that L and E are not both a direct bond simultaneously;
R$_1$ and R$_2$ independently of one another are R$_7$O—, $C_1$–$C_8$alkyl, which is unsubstituted or substituted by OH, $C_1$–$C_4$alkoxy, SR$_8$, CN, ($C_1$–$C_8$alkyl)O(CO)—, ($C_1$–$C_4$alkyl)-(OC)O— or —N(R$_3$)(R$_4$), or R$_1$ and R$_2$ independently of one another are $C_3$–$C_6$alkenyl, phenyl, chlorophenyl, R$_7$—O-phenyl, R$_8$—S-phenyl or phenyl-$C_1$–$C_3$-alkyl, or R$_1$ and R$_2$ together are unbranched or branched $C_2$–$C_9$alkylene, $C_3$–$C_9$oxaalkylene or $C_3$–$C_9$azaalkylene, or R$_1$ and R$_2$ independently of one another are a radical of formula VII or VIII

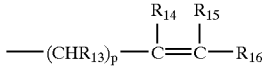 (VII)

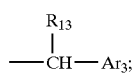 (VIII)

Ar$_3$ is phenyl, naphthyl, furyl, thienyl or pyridiyl, each of which is unsubstituted or substituted by halogen, SH, OH, $C_1$–$C_{12}$alkyl, OH-substituted $C_1$–$C_4$alkyl, halogen-substituted $C_1$–$C_4$alkyl, SH-substituted $C_1$–$C_4$alkyl, N(R$_{17}$)$_2$-substituted $C_1$–$C_4$alkyl, $C_1$–$C_{12}$alkoxy-substituted $C_1$–$C_4$alkyl, ($C_1$–$C_{18}$alkyl)O(OC)-substituted $C_1$–$C_4$alkyl, $CH_3O(CH_2CH_2O)_m$CO-substituted $C_1$–$C_4$alkyl, ($C_1$–$C_4$alkyl)(OC)O-substituted $C_1$–$C_4$alkyl, $C_1$–$C_{12}$alkoxy, ($C_1$–$C_{18}$alkyl)(OC)O-substituted $C_1$–$C_4$alkoxy, $CH_3O(CH_2CH_2O)_m$CO-substituted $C_1$–$C_4$alkoxy, —(OCH$_2$CH$_2$)$_m$OH, —(OCH$_2$CH$_2$)$_m$OCH$_3$, $C_1$–$C_8$alkylthio, phenoxy, —COO($C_1$–$C_{18}$alkyl), —CO(OCH$_2$CH$_2$)$_m$OCH$_3$, phenyl or benzoyl;

m is 1 to 20;

R$_3$ is hydrogen, $C_1$–$C_{12}$alkyl, $C_2$–$C_4$alkyl, which is substituted by OH, SH, $C_1$–$C_4$alkoxy, CN or —COO($C_1$–$C_4$alkyl); or R$_3$ is $C_3$–$C_5$alkenyl, $C_5$–$C_{12}$-cycloalkyl or phenyl-$C_1$–$C_3$alkyl;

R$_4$ is $C_1$–$C_{12}$alkyl; $C_2$–$C_4$alkyl, which is substituted by OH, SH, $C_1$–$C_4$alkoxy, CN or —COO($C_1$–$C_4$alkyl); or R$_4$ is $C_3$–$C_5$alkenyl, $C_5$–$C_{12}$-cycloalkyl, phenyl-$C_1$–$C_3$alkyl; phenyl which is unsubstituted or substituted by halogen, $C_1$–$C_{12}$alkyl, $C_1$–$C_4$alkoxy or —COO($C_1$–$C_4$alkyl);

or R$_4$ together with R$_2$ is $C_1$–$C_7$alkylene, phenyl-$C_1$–$C_4$alkylene, o-xylylene, 2-butenylene, $C_2$–$C_{20}$oxaalkylene or $C_2$–$C_3$azaalkylene; or R$_3$ and R$_4$ together are $C_3$–$C_7$alkylene, optionally interrupted by —O—, —S—, —CO— or —N(R$_6$)— and which $C_3$–$C_7$alkylene is unsubstituted or substituted by OH, SH, $C_1$–$C_4$alkoxy or —COO($C_1$–$C_4$alkyl);

R$_6$ is hydrogen, $C_1$–$C_{12}$alkyl, OH-substituted $C_1$–$C_{12}$alkyl, SH-substituted $C_1$–$C_{12}$alkyl or HS—(CH$_2$)$_n$—COO-substituted $C_1$–$C_{12}$alkyl; $C_2$–$C_{12}$alkyl, which is interrupted by —O—, —NH— or —S—; or R$_6$ is $C_3$–$C_5$alkenyl, phenyl-$C_1$–$C_3$-alkyl, —CH$_2$CH$_2$CN, $C_1$–$C_4$alkyl-CO—CH$_2$CH$_2$—, OH-substituted $C_1$–$C_4$alkyl-CO—CH$_2$CH$_2$—, SH-substituted $C_1$–$C_4$alkyl-CO—CH$_2$CH$_2$—, $C_2$–$C_8$alkanoyl, OH-substituted $C_2$–$C_8$alkanoyl, SH-substituted $C_2$–$C_8$alkanoyl or benzoyl;

R$_7$ is hydrogen, $C_1$–$C_{12}$alkyl, $C_3$–$C_{12}$-alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidinyl, morpholinyl, OH, $C_1$–$C_4$alkoxy, —OCH$_2$CH$_2$CN, —OCH$_2$CH$_2$COO($C_1$–$C_4$alkyl), —O(CO)R$_{19}$, —COOH, —COO($C_1$–$C_8$alkyl), —CONH($C_1$–$C_4$alkyl), —CON($C_1$–$C_4$alkyl)$_2$,

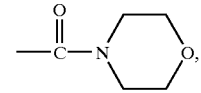

—CO($C_1$–$C_4$alkyl) or by

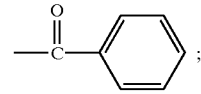

or R$_7$ is 2,3-epoxypropyl, —(CH$_2$CH$_2$O)$_n$H; phenyl which is unsubstituted or substituted by halogen, $C_1$–$C_4$alkyl, $C_1$–$C_4$alkoxy or —COO($C_1$–$C_4$alkyl); or R$_7$ is phenyl-$C_1$–$C_3$-alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si(R$_{20}$)(R$_{21}$)$_2$, or —SO$_2$R$_{22}$;

$R_8$ is hydrogen, $C_1$–$C_{12}$alkyl, $C_3$–$C_{12}$alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidinyl, morpholinyl, OH, $C_1$–$C_4$alkoxy, —OCH$_2$CH$_2$CN, —OCH$_2$CH$_2$COO($C_1$–$C_4$alkyl), —O(CO)R$_{19}$, —COOH, —COO($C_1$–$C_8$-alkyl), —CON($C_1$–$C_4$alkyl)$_2$,

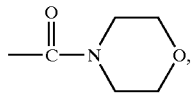

—CO($C_1$–$C_4$alkyl) or

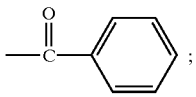

or $R_8$ is 2,3-epoxypropyl, phenyl-$C_1$–$C_3$alkyl, phenyl-$C_1$–$C_3$hydroxyalkyl; phenyl which is unsubstituted or mono- or poly-substituted by halogen, SH, $C_1$–$C_4$alkyl, $C_1$–$C_4$alkoxy or —COO($C_1$–$C_4$alkyl); or
$R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;
$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or poly-substituted by $C_1$–$C_{12}$alkyl or halogen; or $R_9$ and $R_{10}$ together are $C_2$–$C_7$alkylene, optionally interrupted by —O—, —S— or —N(R$_6$)—;
$R_{11}$ and $R_{12}$ independently of one another are a direct bond, —CH$_2$—, —CH$_2$CH$_2$—, —O—, —S—, —CO— or —N(R$_6$)—; provided that $R_{11}$ and $R_{12}$ are not a direct bond simultaneously;
$R_{13}$ is hydrogen, $C_1$–$C_8$alkyl or phenyl;
$R_{14}$, $R_{15}$ and $R_{16}$ independently of one another are hydrogen or $C_1$–$C_4$alkyl;
$R_{17}$ is hydrogen, $C_1$–$C_8$alkyl or phenyl;
$R_{19}$ is $C_1$–$C_4$alkyl, $C_2$–$C_4$alkenyl or phenyl;
$R_{20}$ and $R_{21}$ independently of one another are $C_1$–$C_4$alkyl or phenyl;
$R_{22}$ is $C_1$–$C_{18}$alkyl; or phenyl which is unsubstituted or substituted by $C_1$–$C_{14}$alkyl;
$R_{23}$ and $R_{24}$ independently of one another are hydrogen, or $C_1$–$C_8$alkyl; or $R_{23}$ and $R_{24}$ together are $C_5$–$C_7$cyloalkyl; and
$R_{25}$ is a direct bond, $C_1$–$C_4$alkylene or phenylene.

J as a polymeric group is to be understood as a radical resulting from a polymer or of a copolymer. Examples for polymer groups J are radicals of poly(methacrylate), poly(acrylate), poly(methacrylic acid), poly(acrylic acid), polystyrene, derivatives of polystyrene, poly(diene), polyacrylonitrile, poly(vinyl alcohol), poly(vinyl ester). Examples for copolymer groups J are radicals of poly(methacrylates), poly(acrylates), poly(methacrylates-co-styrene), poly(acrylates-co-styrene). Preferred are poly(methacrylate), poly(acrylate), poly(methacrylic acid), poly(acrylic acid), and polystyrene.

If $CT_1$ is a group

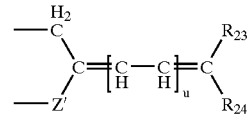

with u=0 a $CT_1$ is

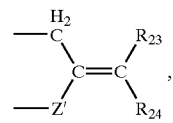

if u=1 a group

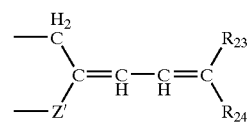

is meant.

Preferred are macrophotoinitiators, wherein PI is a group of formula IIa.

In particular interesting are macrophotoinitiators of formula XIV, wherein
PI is a group of formula IIa

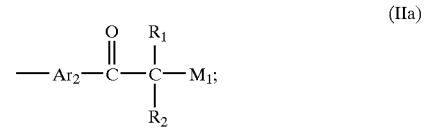

(IIa)

$CT_1$ is —Y'—, —R$_{25}$— or

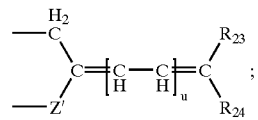

u and t are 0;
l is an integer from 0 to 4;
q is an integer 0 or 1;
o and r independently of one another are an integer 0, 1 or 2;
Z' is —COOR$_{25}$— or —CONR$_9$R$_{25}$—;
Y' is —W$_{(s)t}$—R$_{25}$—;
W is S;
Ar$_2$ is

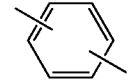

which is unsubstituted or substituted 1 to 4 times by halogen, $C_1$–$C_{12}$alkyl or —OR$_7$;
$R_1$ and $R_2$ independently of one another are $C_1$–$C_8$alkyl which is unsubstituted or substituted by OH, or $C_1$–$C_4$alkoxy; or $R_1$ and $R_2$ independently of one another are $C_3$–$C_6$alkenyl, phenyl, chlorophenyl, or phenyl-$C_1$–$C_3$-alkyl; or $R_1$ and $R_2$ independently of one another are a radical of formula VII or VIII;

$Ar_3$ is phenyl;

$M_1$ is —$NR_3R_4$;

$R_3$ is hydrogen, $C_1$–$C_{12}$alkyl, $C_3$–$C_5$alkenyl, $C_5$–$C_{12}$cycloalkyl or phenyl-$C_1$–$C_3$alkyl;

$R_4$ is $C_1$–$C_{12}$alkyl; or $R_3$ and $R_4$ together are $C_3$–$C_7$alkylene, optionally interrupted by —O—;

$R_6$, $R_7$, $R_8$ and $R_9$ independently of each other are hydrogen or $C_1$–$C_{12}$alkyl;

$R_{13}$, $R_{14}$, $R_{15}$, $R_{16}$, $R_{23}$ and $R_{24}$ are hydrogen; and $R_{25}$ is a direct bond, or $C_1$–$C_4$alkylene.

In accordance with the invention, the macrophotoinitiators can be used as photoinitiators for the photopolymerization of ethylenically unsaturated compounds or of mixtures which comprise such compounds.

The invention therefore also relates to photopolymerizable compositions comprising (A) at least one ethylenically unsaturated photopolymerizable compound and (B) at least one macrophotoinitiator as described above.

The composition may comprise additionally to the component (B) at least one further photoinitiator (C), and/or further coinitiators (D) and/or other additives (E).

The photosensitivity of the novel compositions as described above can extend in general from about 200 nm to 600 nm (UV region).

Ethylenically unsaturated photopolymerizable compounds, component (A), may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl)isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3,000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl and 2,2-di(4-hydroxyphenyl)propane. Examples of polyepoxides are those based on the above mentioned polyols, especially the aromatic polyols, and epichlorohydrin. Other suitable polyols are polymers or copolymers containing hydroxyl groups in the polymer chain or in side groups, examples being polyvinyl alcohol and copolymers thereof, polyhydroxyalkyl methacrylates or copolymers thereof or novolak resins. Further polybis which are suitable are oligoesters having hydroxyl end groups.

Examples of aliphatic and cycloaliphatic polyols are alkylenediols having preferably 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligo-amides having amino end groups. Examples of such unsaturated amides are methylenebisacrylamide, 1,6-hexamethylenebisacrylamide, diethylenetriaminetrismethacrylamide, bis(methacrylamidopropoxy)ethane, 1-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 carbon atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl(meth)acrylates.

The photopolymerizable compounds can be used alone or in any desired mixtures. Preferably used are mixtures of polyol(meth)acrylates.

Binders as well can be added to the novel compositions, and this is particularly expedient when the photopolymerizable-compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5,000 to 2,000,000, preferably 10,000 to 1,000,000. Examples are: homo- and copolymers of acrylates and methacrylates, for example copolymers of methyl methacrylate/ethyl acrylate/methacrylic acid, poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylenadipamide), and polyesters such as poly(ethylene glycol terephtalate) and poly(hexamethylene glycol succinate) and polyimides.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors.

The use of heat-curable resins at the same time is important for use in systems known as hybrid systems, which in a first stage are photopolymerized and in a second stage are cross-linked by means of thermal aftertreatment.

The macrophotoinitiators according to the invention are further suitable as initiators for curing of oxidative drying systems, such as are for example described in "Lehrbuch der Lacke und Beschichtungen", [textbook on varnishes and coatings] Vol. III, 296–328, Verlag W. A. Colomb in Heenemann GmbH, Berlin-Oberschwandorf (1976).

In addition to the photoinitiator the photopolymerizable mixtures may include various additives (E). Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are 1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydro-xyphenyl)-benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy-4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butybenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbo-methoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl)sebacate, bis-(2,2,6,6-tetramethylpiperidyl)succinate, bis-(1,2,2,6,6-pentamethylpiperidyl)sebacate, bis-(1,2,2,6,6-pentamethylpiperidyl)n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexa-methylenediamine and 4-tert-octylamino-2,6-dichloro-1,3,5-s-triazine, tris-(2,2,6,6-tetramethyl-4-piperidyl)nitrilo-triacetate, tetrakis-(2,2,6,6-tetramethyl-4-piperidyl)-1,2,3,4-butane tetraoate, 1,1'-(1,2-ethan-diyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro-[4.5]-decane-2,4-dione, bis-(1-octyloxy-2,2,6,6-tetramethylpiperidyl)sebacate, bis-(1-octyloxy-2,2,6,6-tetramethylpiperidyl)succinate, condensation product of N,N'-bis-(2,2,6,6-tetra-methyl-4-piperidyl) hexamethylenediamine and 4-morpholino-2,6-dichloro-1,3,5-triazine condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione and 3-dodecyl-1-(1,2,2,6,6-pentamethyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]4,6-bis(2,4-dimethylphenyl)-1,3,5-triazine, 2-[4-dodecyl/tridecyl-oxy-(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythrityl diphosphite, tris-(2,4-di-tert-butylphenyl)phosphite, diisodecyl pentaerythrityl diphosphite, bis-(2,4-di-tert-butylphenyl)pentaerythrityl diphosphite, bis-(2,6-di-tert-butyl4-methylphenyl)pentaerythrityl diphosphite, bis-isodecyloxy pentaerythrityl diphosphite, bis-(2,4-di-tert-butyl-6-methylphenyl)pentaerythrityl diphosphite, bis-(2,4,6-tri-tert-butylphenyl)pentaerythrityl diphosphite, tristearyl sorbityl triphosphite, tetrakis-(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl)methyl phosphite and bis(2,4-di-tert-butyl-6-methylphenyl)ethyl phosphite.

Further additives known in the art may be added, as for example flow improvers and adhesion promoters.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention. Examples are mercaptanes, amines and benzothiazol.

Photopolymerization can also be accelerated by adding further photosentisizers or coinitiators (D) which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, camphor quinone, but also eosine, rhodamine and erythrosine dyes.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (D) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP 445624.

Further customary additives, depending on the intended use, are optical brighteners, fillers, pigments, dyes, wetting agents or levelling assistants.

In order to cure thick and pigmented coatings it is appropriate to add glass microspheres or pulverized glass fibres, as described for example in U.S. Pat. No. 5,013,768.

The choice of additive is made depending on the field of application and on properties required for this field. The additives described above are customary in the art and accordingly are added in amounts which are usual in the respective application.

The invention also provides compositions comprising as component (A) at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10,000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one $\alpha,\beta$-ethylenically unsaturated carboxylic acid, of polyurethane (meth)acrylates and of acrylic copolymers which contain $\alpha,\beta$-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP 41125, and suitable waterdispersible, radiation-curable prepolymers of urethane. acrylates can be found in DE 2936039.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel macrophotoinitiators. It is of course also possible to use mixtures with known photoinitiators (C), for example mixtures with benzophenone, benzophenone derivatives, acetophenone, acetophenone derivatives, for example $\alpha$-hydroxycycloalkyl phenyl ketones or 2-hydroxy-2-methyl-1-phenyl-propanone, dialkoxyacetophenones, $\alpha$-hydroxy- or $\alpha$-aminoacetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, monoacyl phosphine oxides, e.g. (2,4,6-trimethylbenzoyl)diphenylphosphine oxide, bisacylphosphine oxides, bis(2,6-dimethoxy-benzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, ferrocenium compounds, or titanocenes, e.g. bis(cyclopentadienyl)-bis(2,6-difluoro-3-pyrryl-phenyl)titanium.

Where the novel macrophotoinitiators are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene)($\eta^5$-cyclopentadienyl)iron (II)hexafluorophosphate.

The photopolymerizable compositions generally comprise 0.05 to 15% by weight, preferably 0.1 to 5% by weight, of the macrophotoinitiator, based on the composition. The amount refers to the sum of all photoinitiators added, if mixtures of initiators are employed. Accordingly, the amount either refers to the photoinitiator (B) or the photoinitiators (B)+(C).

In the prior art the most well-known method for preparing block copolymers is anionic polymerization. This method is, however, sensitive against impurities or low polymerization temperature, and it is only suitable for limited kinds of monomers.

Several attempts to prepare block copolymers by means of radical polymerization have been reported. In J. Macromol. Sci. Chem., A28(1), pp. 129–141 (1991) Yagci and his coworkers, for instance, have disclosed the preparation of a block copolymer using an azo compound having photoinitiating groups. These initiators, however, have a poor thermal stability and are explosive due to the azo group. Moreover, the macrophotoinitiators obtained by the described method have broad molecular weight distribution. Popielarz has employed compounds having thermal chain transferring moieties and thermal initiating moieties to prepare a block copolymer. The macrophotoinitiator is prepared by thermally polymerizing a monomer in the presence of a compound which acts as a chain transfer agent. Again azo compounds are employed, which are unstable and explosive. Moreover some of the azo groups even decompose during the preparation of the macrophotoinitiators and lose the property for polymerizing the second monomer.

Block copolymers have not been prepared from macrophotoinitiators which are thermally stable and have a narrow molecular weight distribution so far.

Accordingly, another object of the invention are block copolymers obtained by the photopolymerization of the above described macrophotoinitiators with radically polymerizable monomers. In particular block-copolymers obtained by photopolymerizing monomers of formula XIII and a macrophotoinitiator as described above.

Monomers which are useful for the preparation of the block copolymers are of formula XIII, as described above.

These monomers can be hydrophilic, amphiphilic or hydrophobic.

Examples of hydrophilic monomers are (meth)acrylamide, N,N-dimethyl(meth)acrylamide, N-isopropenyl (meth)acrylamide, N-vinylformamide, (meth)acrylic acid, crotonic acid, itaconic acid, cinnamic acid, 2-hydroxyethyl(meth)acrylate, 2-hydroxypropyl(meth)acrylate, maleic acid, maleic acid anhydride, n-(1,1-dimethyl 3-oxobutyl)(meth)acrylate, 4-hydroxystyrene, 4-hydroxymethyl styrene, p-1-(2-hydroxybutyl)styrene, p-1-(2-hydroxypropyl)styrene, p-2-(2-hydroxypropyl)styrene and styrene sulfonic acid.

Examples of amphiphilic monomers or oligomers are (meth)acrylonitrile, N-(meth)acrylmorpholine, N-vinylpyrrolidone, N-vinylacetamide, N-vinyl-N-methylacetamide, vinyl methyl ether, polyethylene glycol mono-(meth)acrylate, methoxy poly(ethylene glycol)mono-(meth)acrylate, poly(propylene glycol)mono-(meth)acrylate. N-vinylcaprolactam, N-vinylcarbazole, 4-vinylbenzyl tetrahydrofurfuryl ether and glycidyl(meth)acrylate.

Examples of hydrophobic monomers are methyl(meth)acrylate, ethyl(meth)acrylate, n-butyl(meth)acrylate, tert-butyl(meth)acrylate, 2-ethylhexyl(meth)acrylate, isobornyl(meth)acrylate, lauryl(meth)acrylate, stearyl(meth)acrylate, 1-naphtyl(meth)acrylate, 2-naphtyl(meth)acrylate, adamantyl(meth)acrylate, styrene, 2,4,6-trimethystyrene, 2,5-dichlorostyrene, α-methoxystyrene, α-methylstyrene, 3-methylstyrene, 4-methylstyrene, 3-nitrostyrene, 4-chloromethylstyrene, 4-aminostyrene, 4-tert-butylstyrene, 4-tert-butoxycarbonyloxystyrene, 3-bromostyrene, 4-bromostyrene, 2-chlorostyrene, 3-chlorostyrene, 4-chlorostyrene, 4-cyanostyrene, 4-cyclohexylstyrene, dimethylaminomethyl-styrene, pentachlorostyrene, 4-iodostyrene, β-methoxystyrene, 2-methoxystyrene, 4-methoxystyrene, 1-vinylnaphtalene, 2-vinylnaphtalene, vinyl acetate, vinyl propionate, isobutyl vinyl ether, vinyl chloride, 4-vinylbenzyl chloride, 2-fluoroethyl(meth)acrylate, perfluorocyclohexyl(meth)acrylate, perfluorooctyl(meth)acrylate, 2,2,3,3-tetrafluoropropyl(meth)acrylate, 2,2,2-trifluoroethyl(meth)acrylate and 3-(trifluoromethyl) benzyl(meth)acrylate. The monomers can be used alone or in any desired mixtures.

Preferred block copolymers according to the invention are of formula XV

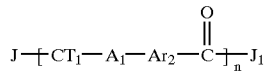

(XV), wherein n is 1 or 2;

Ar$_2$ is

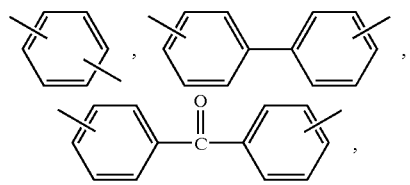

each of which is unsubstituted or substituted 1 to 5 times by halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SR$_8$, —SOR$_8$, —SO$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of formula IV

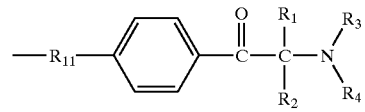

(IV);

or Ar$_2$ is a group of formula Va or VIa

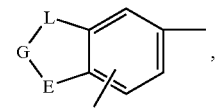

(Va)

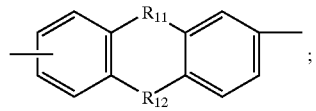

(VIa)

G is unbranched or branched $C_1$–$C_7$alkylene;

L and E independently of one another are a direct bond, —O—, —S— or —N(R$_6$)—, provided that L and E are not both a direct bond simultaneously;

R$_1$ and R$_2$ independently of one another are R$_7$O—, $C_1$–$C_8$alkyl, which is unsubstituted or substituted by OH, $C_1$–$C_4$alkoxy, SR$_8$, CN, ($C_1$–$C_8$alkyl)O(CO)—, ($C_1$–$C_4$alkyl)-(OC)O— or —N(R$_3$)(R$_4$), or R$_1$ and R$_2$ independently of one another are $C_3$–$C_6$alkenyl, phenyl, chlorophenyl, R$_7$—O-phenyl, R$_8$—S-phenyl or phenyl-$C_1$–$C_3$-alkyl, or R$_1$ and R$_2$ together are unbranched or branched $C_2$–$C_9$alkylene, $C_3$–$C_9$oxaalkylene or $C_3$–$C_9$azaalkylene, or R$_1$ and R$_2$ independently of one another are a radical of formula VII or VIII

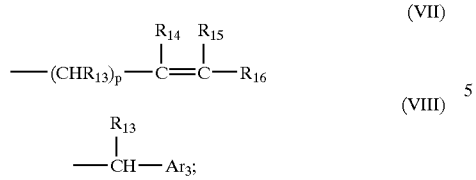

(VII)

(VIII)

p is 0 or 1;

Ar₃ is phenyl, naphthyl, furyl, thienyl or pyridiyl, each of which is unsubstituted or substituted by halogen, SH, OH, $C_1$–$C_{12}$alkyl, OH-substituted $C_1$–$C_4$alkyl, halogen-substituted $C_1$–$C_4$alkyl, SH-substituted $C_1$–$C_4$alkyl, $N(R_{17})_2$-substituted $C_1$–$C_4$alkyl, $C_1$–$C_{12}$alkoxy-substituted $C_1$–$C_4$alkyl, $(C_1$–$C_{18}$alkyl)O(OC)-substituted $C_1$–$C_4$alkyl, $CH_3O(CH_2CH_2O)_m$CO-substituted $C_1$–$C_4$alkyl, $(C_1$–$C_4$alkyl)(OC)O-substituted $C_1$–$C_4$alkyl, $C_1$–$C_{12}$alkoxy, $(C_1$–$C_{18}$alkyl)(OC)O-substituted $C_1$–$C_4$alkoxy, $CH_3O(CH_2CH_2O)_m$CO-substituted $C_1$–$C_4$alkoxy, —$(OCH_2CH_2)_m$OH, —$(OCH_2CH_2)_m$OCH$_3$, $C_1$–$C_8$alkylthio, phenoxy, —$COO(C_1$–$C_{18}$alkyl), —$CO(OCH_2CH_2)_m$OCH$_3$, phenyl or benzoyl;

m is 1 to 20;

$R_3$ is hydrogen, $C_1$–$C_{12}$alkyl, $C_2$–$C_4$alkyl, which is substituted by OH, SH, $C_1$–$C_4$alkoxy, CN or —COO($C_1$–$C_4$alkyl); or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl; $C_2$–$C_4$alkyl, which is substituted by OH, SH, $C_1$–$C_4$alkoxy, CN or —COO($C_1$–$C_4$alkyl); or $R_4$ is $C_3$–$C_5$alkenyl, $C_5$–$C_{12}$-cycloalkyl, phenyl-$C_1$–$C_3$alkyl; phenyl which is unsubstituted or substituted by halogen, $C_1$–$C_{12}$alkyl, $C_1$–$C_4$alkoxy or —COO($C_1$–$C_4$alkyl);

or $R_4$ together with $R_2$ is $C_1$–$C_7$alkylene, phenyl-$C_1$–$C_4$alkylene, o-xylylene, 2-butenylene, $C_2$–$C_3$oxaalkylene or $C_2$–$C_3$azaalkylene;

or $R_3$ and $R_4$ together are $C_3$–$C_7$alkylene, optionally interrupted by —O—, —S—, —CO— or —N(R$_6$)— and which $C_3$–$C_7$alkylene is unsubstituted or substituted by OH, SH, $C_1$–$C_4$alkoxy or —COO($C_1$–$C_4$alkyl);

$R_6$ is hydrogen, $C_1$–$C_{12}$alkyl, OH-substituted $C_1$–$C_{12}$alkyl, SH-substituted $C_1$–$C_{12}$alkyl or HS—(CH$_2$), —COO-substituted $C_1$–$C_{12}$alkyl; $C_2$–$C_{12}$alkyl, which is interrupted by —O—, —NH— or —S—; or $R_6$ is $C_3$–$C_5$alkenyl, phenyl-$C_1$–$C_3$-alkyl, —CH$_2$CH$_2$CN, $C_1$–$C_4$alkyl-CO—CH$_2$CH$_2$—, OH-substituted $C_1$–$C_4$alkyl-CO—CH$_2$CH$_2$—, SH-substituted $C_1$–$C_4$alkyl-CO—CH$_2$CH$_2$—, $C_2$–$C_8$alkanoyl, OH-substituted $C_2$–$C_8$alkanoyl, SH-substituted $C_2$–$C_8$alkanoyl or benzoyl;

$R_7$ is hydrogen, $C_1$–$C_{12}$alkyl, $C_3$–$C_{12}$-alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidinyl, morpholinyl, OH, $C_1$–$C_4$alkoxy, —OCH$_2$CH$_2$CN, —OCH$_2$CH$_2$COO($C_1$–$C_4$alkyl), —O(CO)R$_{19}$, —COOH, —COO($C_1$–$C_8$alkyl), —CONH($C_1$–$C_4$alkyl), —CON($C_1$–$C_4$alkyl)$_2$,

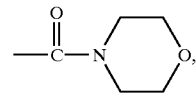

—CO($C_1$–$C_4$alkyl) or by

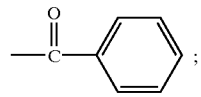

or $R_7$ is 2,3-epoxypropyl, —(CH$_2$CH$_2$O)$_n$H; phenyl which is unsubstituted or substituted by halogen, $C_1$–$C_4$alkyl, $C_1$–$C_4$alkoxy or —COO($C_1$–$C_4$alkyl); or $R_7$ is phenyl-$C_1$–$C_3$-alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si(R$_{20}$)(R$_{21}$)$_2$, or —SO$_2$R$_{22}$;

$R_8$ is hydrogen, $C_1$–$C_{12}$alkyl, $C_3$–$C_{12}$alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidinyl, morpholinyl, OH, $C_1$–$C_4$alkoxy, —OCH$_2$CH$_2$CN, —OCH$_2$CH$_2$COO($C_1$–$C_4$alkyl), —O(CO)R$_{19}$, —COOH, —COO($C_1$–$C_8$-alkyl), —CON($C_1$–$C_4$alkyl)$_2$,

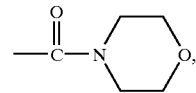

—CO($C_1$–$C_4$alkyl) or

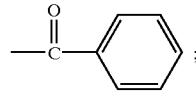

or $R_8$ is 2,3-epoxypropyl, phenyl-$C_1$14 $C_3$alkyl, phenyl-$C_1$–$C_3$hydroxyalkyl; phenyl which is unsubstituted or mono- or polysubstituted by halogen, SH, $C_1$–$C_4$alkyl, $C_1$–$C_4$alkoxy or —COO($C_1$–$C_4$alkyl); or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or poly-substituted by $C_1$–$C_{12}$alkyl or halogen; or $R_9$ and $R_{10}$ together are $C_2$–$C_7$alkylene, optionally interrupted by —O—, —S— or —N(R$_6$)—;

$R_{11}$ and $R_{12}$ independently of one another are a direct bond, —CH$_2$—, —CH$_2$CH$_2$—, —O—, —S—, —CO— or —N(R$_6$)—; provided that $R_{11}$ and $R_{12}$ are not a direct bond simultaneously;

$R_{13}$ is hydrogen, $C_1$–$C_8$alkyl or phenyl;

$R_{14}$, $R_{15}$ and $R_{16}$ independently of one another are hydrogen or $C_1$–$C_4$alkyl;

$R_{17}$ is hydrogen, $C_1$–$C_8$alkyl or phenyl;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl; or phenyl which is unsubstituted or substituted by $C_1$–$C_{14}$alkyl;

$A_1$ is a direct bond, —X[(CH$_2$)$_l$X']$_q$—[(C$_6$H$_4$)$_o$X"]$_r$—, —O—, —S— or —N(R$_6$)—;

X, X' and X" independently of each other are a direct bond, —O—, —S—, —N(R$_6$)—, —O(CO)—, —COO— —NHCO—, —CONH— or —CO—;

l is an integer from 0 to 10;

q is an integer from 0 to 5;

o and r independently of one another are an integer 0, 1 or 2;

$CT_1$ is —Y'—, —$R_{25}$—,

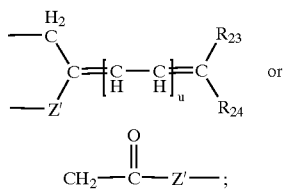

or

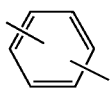

Z' is —COOR$_{25}$—, —CONR$_9$R$_{25}$—, or —Ar$_2$—;

Y' is —W(R$_8$)$_t$R$_{25}$—;

t is an integer 0, 1 or 2;

W is S, Si, Se, P, Br, Cl, Sn, —O—O—, S(=O), S(=O)$_2$, or P(=O);

$R_{23}$ and $R_{24}$ independently of one another are hydrogen, or $C_1$–$C_8$alkyl; or $R_{23}$ and $R_{24}$ together are $C_5$–$C_7$cyloalkyl; and $R_{25}$ is a direct bond, $C_1$–$C_4$alkylene or phenylene.

u is 0 or 1; and

J and $J_1$ independently of one another are a polymeric group, provided that J and $J_1$ are not simultaneously the same groups.

Further preferred block copolymers are such, wherein formula XV $Ar_2$ is

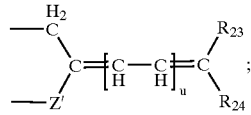

which is unsubstituted or substituted 1 to 4 times by halogen, $C_1$–$C_{12}$alkyl or —OR$_7$;

$R_7$ is hydrogen or $C_1$–$C_{12}$alkyl;

X, X' and X" independently of each other are a direct bond, —O—, —S— or —N(R$_6$)—;

$R_6$ is hydrogen or $C_1$–$C_{12}$alkyl;

l is an integer from 0 to 4;

q is an integer from 0 or 1;

o and r independently of one another are an integer 0, 1 or 2;

$CT_1$ is —Y'— or

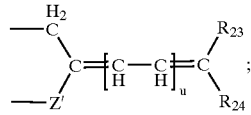

Z' is —COOR$_{25}$— or —CONR$_9$R$_{25}$—;

t and u are 0;

W is S;

$R_8$ and $R_9$ independently of one another are hydrogen or $C_1$–$C_{12}$alkyl;

$R_{23}$ and $R_{24}$ are hydrogen; and $R_{25}$ is a direct bond or $C_1$–$C_4$alkylene.

Accordingly, for example, the following block-copolymers are obtained: polystyrene-block-polybutadiene, polystyrene-block-polyisobutene, polybutadiene-block-poly(tert-butyl methacrylate) or polyisoprene block-poly(tert-butyl methacrylate), which, for example can be employed as lubricant or oil; poly(ethylhexyl methacrylate)-block-poly(methacrylic acid), which can be employed, for example, as a pigment dispersant or an emulsion stabilizer; polystyrene-block-polybutadiene, polystyrene-block-poly(methyl acrylate), (polyacrylo-nitrile-random-polystyrene)-block-(polystyrene-random-polybutadiene), polybutadiene-block-poly(dimethyl itaconate), which, for example, can be employed as thermoplastic elastomers; polystyrene-block-poly(vinyl acetate), poly(methyl methacrylate)-block-poly(vinyl acetate), which, for example, can be employed as polymeric additive for polyester resin FRP molding; {poly(butyl methacrylate)-random-poly(methyl methacrylate)}-block-poly(perfluoroethyl acrylate), polystyrene-block-poly(hydroxylethyl methacrylate), which can be employed, for example, as surface treatment reagent; polystyrene-block-poly(tert-butyl methacrylate), polystyrene-block-poly(methyl methacrylate), polystyrene-block-poly(tert-butyl acrylate), polystyrene-block-poly(4-vinylpyridine), polystyrene-block-poly(2-vinylpyridine), polystyrene-block-poly(tert-butylstyrene), polybutadiene-block-poly(methyl methacrylate), polyisoprene-block-poly(methyl methacrylate), polybutadiene-block-poly(tert-butyl acrylate), polyisoprene-block-poly(tert-butyl acrylate), poly(methyl methacrylate)-block-poly(tert-butyl methacrylate), poly(methyl methacrylate)-block-poly(tert-butyl acrylate), poly(methyl methacrylate)-block-poly(2-vinylpyridine), poly(methyl methacrylate)-block-poly(4-vinylpyridine), poly(tert-butyl methacrylate)-block-poly(tert-butyl methacrylate)-block-poly(tert-butyl acrylate), poly(tert-butyl acrylate)-block-poly(2-vinylpyridine), poly(tert-butyl acrylate)-block-poly(4-vinylpyridine), poly(2-vinylpyridine)-block-poly(4-vinylpyridine), and so on.

Examples for amphiphilic block copolymers are polystyrene-block-poly(sodium methacrylate), polystyrene-block-poly(sodium acrylate), polystyrene-block-poly(methacrylic acid), polystyrene-block-poly(acrylic acid), polystyrene-block-poly(N-methyl-4-vinylpyridinium iodide), polystyrene-block-poly(N-methyl-2-vinylpyridinium iodide), polystyrene-block-poly(2-hydroxyethyl acrylate), polystyrene-block-poly(2-hydroxyethyl methacrylate), polystyrene-block-poly(2-hydroxyethyl acrylate), polystyrene-block-poly(2-hydroxyethyl methacrylate), polyisoprene-block-poly(sodium methacrylate), polyisoprene-block-poly(sodium acrylate), polyisoprene-block-poly(methacrylic acid), polyisoprene-block-poly(acrylic acid), polyisoprene-block-poly(N-methyl-4-vinylpyridinium iodide), polyisoprene-block-poly(N-methyl-2-vinylpyridinium iodide), polyisoprene-block-poly(2-hydroxyethyl acrylate), polyisoprene-block-poly(2-hydroxyethyl methacrylate), polyisoprene-block-poly(2-hydroxyethyl acrylate), polybutadiene-block-poly(2-hydroxyethyl methacrylate), polybutadiene-block-poly(sodium methacrylate), polybutadiene-block-poly(sodium acrylate), polybutadiene-block-poly(methacrylic acid), polybutadiene-block-poly(acrylic acid), polybutadiene-block-poly(N-methyl-4-vinylpyridinium iodide), polybutadiene-block-poly(N-methyl-2-vinylpyridinium iodide), polybutadiene-block-poly(2-hydroxyethyl acrylate), polybutadiene-block-poly(2-hydroxyethyl methacrylate), polybutadiene-block-poly(2-hydroxyethyl acrylate), polybutadiene-block-poly(2-hydroxyethyl methacrylate), poly(methyl methacrylate)-block-poly(2-hydroxyethyl methacrylate), poly(methyl methacrylate)-block-poly(sodium methacrylate), poly(methyl methacrylate)-block-poly(sodium acrylate), poly(methyl methacrylate)-block-poly(methacrylic acid), poly(methyl methacrylate)-block-poly(acrylic acid), poly(methyl methacrylate)-block-poly(N-methyl-4-vinylpyridinium iodide), poly(methyl methacrylate)-block-poly(N-methyl-2-vinylpyridinium iodide), poly(methyl methacrylate)-block-poly(2-hydroxyethyl acrylate), poly(methyl methacrylate)-block-poly(2-hydroxyethyl methacrylate), poly(methyl methacrylate)-block-poly(2-hydroxyethyl acrylate), poly(methyl methacrylate)-block-poly(2-hydroxyethyl methacrylate), poly(tert-butyl methacrylate)-block-poly(2-hydroxyethyl methacrylate), poly(tert-butyl methacrylate)-block-poly(sodium methacrylate), poly(tert-butyl methacrylate)-block-poly(sodium acrylate), poly(tert-butyl methacrylate)-block-poly(methacrylic acid), poly(tert-butyl methacrylate)-block-poly(acrylic acid), poly(tert-butyl methacrylate)-block-poly(N-methyl-4-vinylpyridinium iodide), poly(tert-butyl methacrylate)-block-poly(N-methyl-2-vinylpyridinium iodide), poly(tert-butyl methacrylate)-block-poly(2-hydroxyethyl acrylate), poly(tert-butyl methacrylate)-block-poly(2-hydroxyethyl methacrylate), poly(tert-butyl methacrylate)-block-poly(2-hydroxyethyl acrylate), poly(tert-butyl methacrylate)-block-poly(2-hydroxyethyl methacrylate), poly(ethylhexyl methacrylate)-block-poly(acrylic acid), poly(ethylhexyl acrylate)-block-poly(methacrylic acid), poly(ethylhexyl acrylate)-block-poly(acrylic acid).

Subject of the invention also is a process for preparing a block copolymer of formula XV, characterized in that a macrophotoinitiator as descsribed above and at least one radically polymerizable monomer are mixed and irradiated with light.

The photopolymerization can be carried out in bulk or in any solution at any concentration. Examples of suitable solvents are hydrocarbons such as benzene, toluene, xylene, cyclohexane; esters such as ethyl acetate, butyl acetate, amyl acetate; ketones such as acetone, methyl ethyl ketone, methyl isobutyl ketone, cyclohexanone; ethers such as tetrahydrofuran and 1,4-dioxane; alcohols such as methanol, ethanol, isobutyl alcohol 1,2,6-hexanetriol glycerin; amides such as N,N-dimethylformamide, N-methylformamide, N,N-diethylformamide, N-methylacetamide, N,N-dimethylacetamide, N-methylpropionamide; pyrrolidones such as 1-methyl-2-pyrrolidone, pyrrolidone ε-caprolactam; glycols such as ethylene glycol, propylene glycol, butylene glycol, tri(methylene glycol), tri(ethylene glycol), hexylene glycol, di(ethylene glycol), diethylene glycol, di(propylene glycol), poly(ethylene glycol); glycol ethers such as 2-methoxyethanol, 2-ethoxyethanol, 2-(2-methoxy)ethoxy ethanol, 2-propoxyethanol, 2-butoxyethanol, di(ethylene glycol)monomethyl ether, di(ethylene glycol)monoethyl ether, di(ethylene glycol)monobutyl ether, tri(ethylene glycol)monoethyl ether, 1-methoxy-2-propanol, 1-ethoxy-2-propanol, di(propylene glycol)monomethyl ether, di(propylene glycol)monoethyl ether, tri(propylene glycol) monomethyl ether, 3-methoxyl-3-methyl-1-butanol; halogenated hydrocarbon, such as chloroform or methylene chloride. The solvent may also be in the form of a mixture of two or more of the above-mentioned solvents.

It is appropriate to conduct the polymerization in an inert atmosphere in order to avoid inactivation of the generated radicals. Examples of suitable inert gases are nitrogen, helium, neon, argon and xenon.

The polymerization usually is conducted at an appropriate temperature at which the monomers can be polymerized. The temperature strongly depends on the choice of the monomer and solvent. It should be higher than the melting point of the employed monomers and solvents and lower than the boiling point of them. The temperature is generally in the range from −40° C. to 180° C., preferably from 0° C. to 100° C.

The photopolymerization can also be conducted according to the method described in WO 98/37105 in order to prepare oligomers having a specific molecular weight.

The number and weight average molecular weights of the obtained block copolymers can be determined by a common method such as GPC measurement calibrated by the standard styrene or/and methacrylate and are in the range from 300 to 10,000,000, preferably from 500 to 1,000,000.

Block copolymers generally are useful for various applications and also the block-copolymers according to the invention can be employed for various purposes.

Polystyrene-block-polybutadiene or polystyrene-block-polyisobutene can, for example, be a key component for "low temperature adhesives for photographic materials" as disclosed in U.S. Pat. No. 4,126,464.

Poly(tert-butyl methacrylate)-block-polybutadiene or poly(tert-butyl methacrylate)-block-polyisoprene, for instance, can be employed as lubricant as disclosed in U.S. Pat. No. 5,002,676.

Amphiphilic block copolymers, especially poly(hydroxyhexyl methacrylate)-block-{poly(methyl methacrylate)-random-poly(acrylic acid)} or poly(hydroxyhexyl methacrylate)-block-poly(methyl methacrylate), are for example employed as bio-compatible polymers for medical materials, as is decribed in JP 3-223377 A.

Polystyrene-block-polydiene, especially polystyrene-block-polybutadiene and polystyrene-block-polyisoprene, can be used as a material for an imageable resist composition as is for example disclosed in U.S. Pat. No. 5,318,877.

Poly(ethylhexyl methacrylate)-block-poly(methacrylic acid) exhibits a very good pigment dispersibility and emulsion stability, as is described in an article in Progress in Organic Coating 27(1996), 255–260.

According to Ueda, Kagaku To Kogyo [Chemical Industry Japan], 70(5), 184–190, the following block copolymers are suitable for many proposes, for instance as thermoplastic elastomers: polystyrene-block-polybutadiene, poly(methyl acrylate)-block-polystyrene, (polyacrylonitrile-random-polystyrene)-block-(polystyrene-random-polybutadiene), poly(dimethyl itaconate)-block-polybutadiene; as polymeric additives for polyester resin FRP molding: polystyrene-block-poly(vinyl acetate), poly(methyl methacrylate)-block-poly(vinyl acetate); as surface treatment reagent: {poly(butyl methacrylate)-random-poly(methyl methacrylate)}-block-poly(perfluoroethyl acrylate), poly(hydroxylethyl methacrylate)-block-polystyrene.

Accordingly, subject of the invention is the use of block copolymers according to the present invention for the preparation of pigment dispersants, emulsion stabilizers, plastic elastomers, antishrinking agents, coatings, powder coatings, medical materials, imaging materials, thermal transfer imaging resins; for the preparation of tackfiers for adhesives, base resins for hot melt adhesives, pressure sensitive adhesives, or solvent applied adhesives, laminating adhesives for glass, adhesives for adhering a polymer; for the preparation of oil additives for smoke suppression, viscositiy modifiers for lubricating oils, pour point depressants for fuels or oils; for the preparation of modifiers for asphalt, wire insulations or jacketing, tougheners for polyolefines, drip suppressants for synthetic polymers, additives for wax candles for smoke suppression or drip control, blown or cast films or sheets, foamed objects, hoses, non-woven fabrics, roofing membranes, tougheners for thermoplastics or thermosets, internal plasticizers for polymers, capliner resins, fine denier fibres, compatibilizing agents, flexible pouches, wrap packaging films, as base for synthetic lubricants; as base polymer for caulking; as base resin for carpet backings, as additive to thermoplastic polymers to improve the adhesion of paint thereto, or as antifogging agents.

Such applications are, for example, described in U.S. Pat. No. 5,880,241.

To perform the photopolymerization, either of the novel compositions (comprising a macrophotoinitiator and a radically polymerizable monomer) or to perform the photopolymerisation for the prepapration of the block-copolymers according to the invention suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-pressure, high-pressure and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as KrF lasers for exposure at 248 nm or ArF lasers are also suitable. Lasers in the visible region can also be employed. By this method it is possible to produce printed circuits in the electronics industry, lithographic offset printing plates or relief printing plates, and also photographic image recording materials.

The photopolymerizable compositions as well as the block copolymers according to the invention can be used for various purposes, for example as printing ink, as a clear finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres.

The compositions according to the invention are further suitable for the production of medical equipment (e.g. contact lenses), auxiliaries or implants.

Further the compositions according to the invention are suitable for the preparation of gels with thermotropic properties, as for example described in DE 19700064 and EP 678534.

Accordingly, a further subject of the invention is the use of a macrophotoinitiator according to the invention for producing pigmented and non-pigmented paints and varnishes, for producing clear and pigmented aqueous dispersions, powder coatings, printing inks, printing plates, adhesives, dental filling compositions, wave-guides, optical switches, color proofing systems, glass fiber cable coatings, screen printing stencils, resist materials, composite compositions, for photographic reproductions, for producing masks for screen printing, for photoresists for printed electronic circuits, for encapsulating electrical and electronic components, for producing magnetic recording materials, for producing three-dimensional objects by means of stereolithography or bulk-curing, and as image recording material, especially for holographic recording.

The novel macrophotoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel macrophotoinitiator can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a photoinitiator according to the invention, similar formulations being described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutile titanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiator the powder coating formulations may also include UV absorbers. Appropriate examples are listed above in sections 1.–8.

The novel photocurable compositions are suitable, for example, as coating materials for substrates of all kinds, for example wood, textiles, paper, ceramics; glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 $\mu$m to more than 100 $\mu$m, for example 20 mm or 0.02 to 10 cm, preferably 0.02 to 2 cm.

The invention therefore also pertains to a substrate coated with a photopolymerizable composition as described above.

The novel radiation-sensitive compositions further find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing plates, for the production of printing formes for relief printing, planographic printing, rotogravure or of screen printing formes, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording or image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 $\mu$m to 10 $\mu$m, while for printed circuits it is from 1.0 $\mu$m to about 100 $\mu$m.

Following the coating of the substrates, the solvent is removed, generally by drying, to leave a coat of the photo resist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes. The photopolymerizable composition comprising the macrophotoinitiator, as well as the block copolymers according to the invention can be used in color filter (color mosaique) resists.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel compositions are suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqeos solutions.

Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", [glass fiber-enforced plastics] page 610, Springer Veriag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

In the following examples the following photoinitiators with chain transfer groups are used to prepare the macro-photoinitiators according to the invention:

1

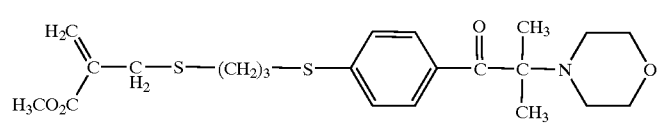

2

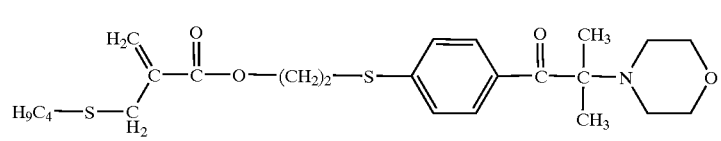

-continued

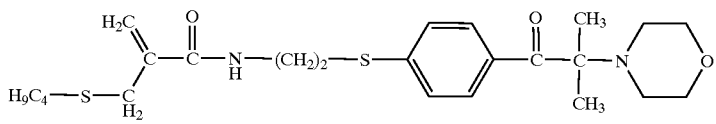
3

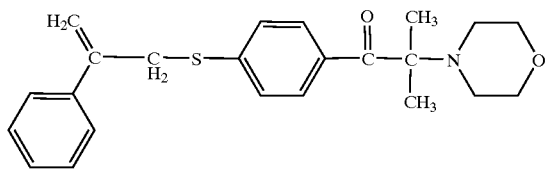
4

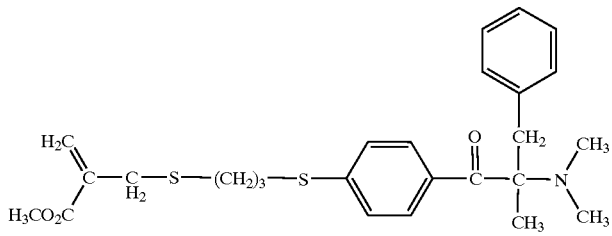
6

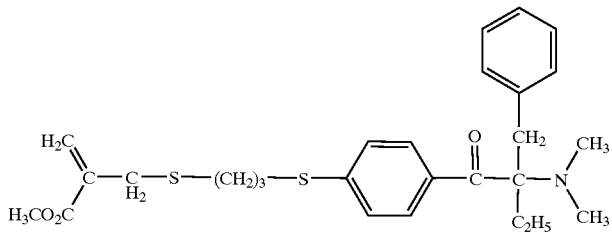
7

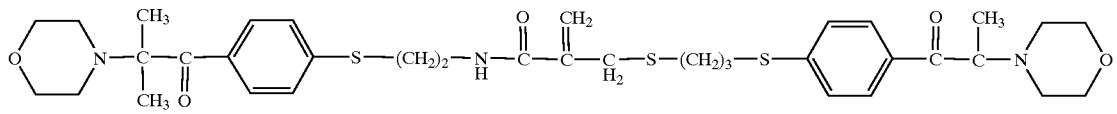

In the following examples

MMA=methylmethacrylate (Tokyo Kasei Kogyo Co., Ltd. Tokyo Japan) and styrene (Wako Pure Chemical industries, Osaka Japan) are purified and destilled under vacuum just before the polymerization.

Toluene (Wako Pure Chemical Industries, Osaka Japan) is destilled for purification.

AIBN=2,2'-Azobisisobutyronitrile (Nacalai Tesques, Kyoto Japan) is used as received from the provider.

GPC measurement=Gel Permeation Chromatography (method described below)

A) Preparation of Photoinitiators with Chain Transfer Groups

EXAMPLE 1

2-{3-[4-(2-Methyl-2-morpholin-4-yl-propionyl)-phenylthio]-propylthiomethyl}-acrylic acid methyl ester (1)

1.1 2-(4-Fluorophenyl)-3,3-dimethyl-2-methoxyoxirane 100.32 g (0.41 mol) of 2-bromo-1-(fluorophenyl)-2-methylpropan-1-one, prepared by brominating 1-(4-fluorophenyl)-2-methylpropane-1-one analogously to EP 3002, are dissolved in 80 ml of dry methanol. 24.3 g (0.45 mol) of sodium methoxide in a solvent mixture of 60 ml of dry methanol and 120 ml of chlorobenzene are added dropwise at 20° C. The methanol is then distilled off and the residue is taken up with chlorobenzene. The salt is filtered off, and the chlorobenzene solution is concentrated. The liquid crude product, 90.8 g, is further purified by distillation, 60° C. at 0.2 mmHg.

1.2 1-(4-Fluorophenyl)-2-methyl-2-morpholin-4-yl-propan-1-one 69.3 g (0.35 mol) of 2-(4-fluorophenyl)-3,3-dimethyl-2-methoxyoxirane and 200 ml of dry morpholine are mixed, and the mixture is heated to reflux temperature (about 130° C.). After 26 hr, the excess of morpholine is distilled off. The residue is taken up with toluene and washed with water and saturated sodium chloride solution successively. The toluene solution is dried with $MgSO_4$ and is concentrated. The residue, 88.1 g, crystallizes from ethanol with a melting point of 63–66° C.

1.3 1-[4-(3-Mercaptopropylthio)phenyl]-2-methyl-2-morpholin-4-yl-propane-1-one 52.8 g (0.488 mol) of 1,3-propanedithiol are dissolved in 100 ml of dry dimethylacetamide, and the solution is heated to about 40° C. together with 22.0 g of potassium carbonate. 20.0 g (0.08 mol) of 1-(4-fluorophenyl)-2-methyl-2-morpholin-4-yl-propan-1-one in 50 ml of dry dimethylacetamide are added dropwise over 14 hr. The suspension is stirred for additional 5 hr, then the solid is filtered off and washed with toluene. The excesses of 1,3-propanedithiol and toluene are distilled off. The residue is dissolved in ethyl acetate and the resulting solution is washed with saturated ammonium chloride solution, is dried over $MgSO_4$ and is concentrated. The residue is recrystallized from ethanol. The obtained product has a melting point of 67–68° C.

The structure is confirmed by the $^1$H-NMR spectrum (CDCl$_3$): δ1.31 (s, 6H), 1.39 (t, 1H), 2.00 (m, 2H), 2.57 (t, 4H), 2.70 (q, 2H), 3.13 (t, 2H), 3.69 (t, 4H), 7.28 (d, 2H), 8.50 (d, 2H).

1.3 2-{3-[4-(2-Methyl-2-morpholin-4-yl-propionyl)-phenylthio]-propylthiomethyl}-acrylic acid methyl ester 3.0 g (8.8 mmol) of 1-[4-(3-mercaptopropylthio)phenyl]-2-methyl-2-morpholin-4-yl-propane-1-one are dissolved in 1.50 ml of methanol. To the solution are successively added 1.89 g (10.6 mmol) of methyl 2-(bromomethyl)acrylate and 1.22 g (8.8 mmol) of potassium carbonate, and the reaction mixture is stirred at room temperature for 10 min. The reaction mixture is poured into water and extracted with ethyl acetate. The organic phase is washed with water, and dried over MgSO4. After distilling off the ethyl acetate, the residue is purified by means of column chromatography on silica gel with ethyl acetate-hexane (1:3) as an eluent, and an oily product is obtained.

The structure is confirmed by the $^1$H-NMR spectrum (CDCl$_3$): δ1.31 (s, 6H), 1.97 (m, 2H), 2.57(m, 4H), 2.62 (t, 2H), 3.10 (t, 2H), 3.39 (s, 2H), 3.72 (m, 4H), 3.79 (s, 3H), 5.64 (s, 1H), 6.21 (s, 1H), 7.27 (d, 2H), 8.50 (d, 2H).

EXAMPLE 2

2-Butylthiomethyl-acrylic acid 2-[4-(2-methyl-2-morpholin-4-yl-propionyl)-phenylthio]-ethyl ester
(2)

2.1 1-[4-(2-Hydroxyethylthio)phenyl]-2-methyl-2-morpholin-4-yl-propane-1-one 3.0 g (11.9 mmol) of 1-(4-fluorophenyl)-2-methyl-2-morpholin-4-yl-propan-1-one and 0.93 g (11.9 mmol) of 2-mercaptoethanol are dissolved in 10 ml of dry dimethylacetamide, and the solution is heated to about 50° C. together with 3.29 g of potassium carbonate overnight. The reaction mixture is poured into water and extracted with ethyl acetate. The organic phase is washed with water, dried over MgSO$_4$ and evaporated. The residue is purified by means of column chromatography on silica gel with ethyl acetate-hexane (1:3) as an eluent.

The structure is confirmed by the $^1$H-NMR spectrum (CDCl$_3$): δ1.31 (s, 6H), 1.98 (t, 1H), 2.57(m, 4H), 3.22 (t, 2H), 3.69 (m, 4H), 3.85 (q, 2H), 7.33 (d, 2H), 8.50 (d, 2H).

2.2 2-Butylthiomethyl-acrylic acid 2-[4-(2-methyl-2-morpholin-4-yl-propionyl)-phenylthio]-ethyl ester 1.0 g (3.2 mmol) of 1-[4-(2-Hydroxyethylthio)phenyl]-2-methyl-2-morpholin-4-yl-propane-1-one and 0.56 g (3.2 mmol) of 2-(butylthiomethyl)acrylic acid are dissolved in 20 ml of dry dimethylacetamide and cooled to −20° C. To the solution is added 0.68 g (3.54 mmol) of 1-ethyl-3-(3-dimethylaminopropyl)carbodiimide hydrochloride in 5 ml of dry dimethylacetamide. The mixture is gradually warmed to room temperature and stirred overnight. To the mixture is added ethyl acetate. The mixture then is washed with saturated sodium chloride solution and dried over MgSO$_4$. After distilling off the ethyl acetate, the residue is purified by means of column chromatography on silica gel with ethyl acetate-hexane (1:2) as an eluent, and an oily product is obtained.

The structure is confirmed by the $^1$H-NMR spectrum (CDCl$_3$), δ0.91 (t, 3H), 1.31 (s, 6H),1.35–1.42 (m, 2H), 1.51–1.59 (m, 2H), 2.45 (t, 2H), 2.57 (m, 4H), 3.30 (t, 2H), 3.35 (s, 2H), 3.70 (m, 4H), 4.41 (t, 2H), 5.65 (s, 1H), 6.18 (s, 1H), 7.35 (d, 2H), 8.51 (d, 2H).

EXAMPLE 3

2-Butylthioethyl-N-{2-[4-(2-methyl-2-morpholin-4-yl-propionyl)-phenylsulfanyl]-ethyl}-acrylamide (3)

3.1 1-[4-(2-Amino-ethylthio)-phenyl]-2-methyl-2-morpholin-4-yl-propan-1-one 3.0 g (11.9 mmol) of 1-(4-fluorophenyl)-2-methyl-2-morpholin-4-yl-propan-1-one and 2.76 (35.8 mmol) of 2-aminoethanethiol are dissolved in 30 ml of dry dimethylacetamide, and the solution is heated to about 70° C. together with 3.29 g of potassium carbonate overnight. The reaction mixture is poured into water and extracted with ethyl acetate. After the organic phase is washed with water, the amine compound is extracted with hydrochloric acid solution (pH 1) and washed with ethyl acetate. The aqueous phase is neutralized with sodium hydroxide solution and extracted with ethyl acetate. This organic phase is washed with water and dried over MgSO$_4$. After distilling off the ethyl acetate, the desired product is obtained. The structure is confirmed by the $^1$H-NMR spectrum (CDCl$_3$), δ1.31 (s, 6H), 2.57(m, 4H), 3.01 (t, 2H), 3.17 (t, 2H), 3.69 (m, 4H), 7.30 (d, 2H), 8.50 (d, 2H).

3.2 2-Butylthiomethyl-N-{2-[4-(2-methyl-2-morpholin-4-yl-propionyl)-phenylsulfanyl]-ethyl}-acrylamide 0.45 g (1.5 mmol) of 1-[4-(2-amino-ethylthio)-phenyl]-2-methyl-2-morpholin-4-yl-propan-1-one and 0.26 g (1.5 mmol) of 2-(butylthiomethyl)acrylic acid are dissolved in 15 ml of dry dimethylacetamide and cooled to −20° C. To the solution is added 0.268 g (1.7 mmol) of 1-ethyl-3-(3-dimethylaminopropyl)carbodiimide in 5 ml of dry dimethylacetamide containing 1% of methylenechloride. The mixture is gradually warmed to room temperature and stirred overnight. To the mixture is added ethyl acetate and washed with 1 N hydrochloric acid solution containing sodium chloride, saturated sodium hydrogen carbonate solution, and water. The organic phase is dried over MgSO$_4$. After distilling off the, ethyl acetate, the residue is purified by means of column chromatography on silica gel with ethyl acetate-hexane (1:1) as an eluent, and an oily product is obtained.

The structure is confirmed by the $^1$H-NMR spectrum (CDCl$_3$), δ0.91 (t, 3H), 1.31 (s, 6H),1.41 (m, 2H), 1.55 (m, 2H), 2.45 (t, 2H), 2.57 (m, 4H), 3.22 (t, 2H), 3.37 (s, 2H), 3.62 (q, 2H), 3.69 (m, 4H), 5.39 (s, 1H), 5.89 (s, 1H), 7.00 (br, 1H), 7.35 (d, 2H), 8.51 (d, 2H).

EXAMPLE 4

2-Methyl-2-morpholin-4-yl-1-[4-(2-phenyl-allylsulfanyl)-phenyl]-propan-1-one (4)

4.1 (1-Bromomethyl-vinyl)benzene 100 g of N-bromosuccinimide are added to the mixture of 250 ml of α-methylstyrene and 40 ml of carbon tetrachloride. The resulting mixture is heated to reflux for 5 min. and cooled in an ice-water bath. Filtration and concentration give the desired compound, 1-bromo-2-phenylpropene, and an isomer thereof (65:35).

4.2 2-Phenyl-prop-2-ene-1-thiol 19.2 g of potassium thioacetic acetate in 100 ml of dried dimethylacetamide are added dropwise to 25.5 g of (1-bromomethyl-vinyl)benzene at room temperature. After stirring for 16 hr, the mixture is poured into water and extracted with ethyl acetate. The ethyl acetate solution is dried over MgSO$_4$ and is concentrated to give a crude oil. The crude product is purified by means of column chromatography on silica gel with hexane. 5.1 g of the purified product are dissolved in 50 ml of ethanol. To the solution are added 15 ml of 2N sodium hydroxide solution and the resulting mixture is stirred for 2 hr at room temperature. 15 ml of 2N hydrochloric acid solution are added and the ethanol is distilled off. The product is extracted with ethyl acetate and the organic phase is washed with water and saturated sodium chloride solution successively and then is dried over $MgSO_4$. After distilling off the ethyl acetate, the residue is purified by means of column chromatography on silica gel with ethyl acetate-hexane (1:99) as an eluent, and an oily product is obtained.

The structure is confirmed by the $^1$H-NMR spectrum ($CDCl_3$), δ1.60 (t, 1H), 3.65 (d, 2H), 5.31 (s, 1H), 5.37 (s, 1H), 7.30–7.46 (m, 5H).

4.3 2-Methyl-2-morpholin-4-yl-1-[4-(1-phenyl-vinylthio)-phenyl]-propan-1-one 3.18 g (12.7 mmol) of 1-(4-fluorophenyl)-2-methyl-2-morpholin-4-yl-propan-1-one and 1.84 g (12.2 mmol) of 2-phenyl-prop-2-ene-1-thiol are dissolved in 50 ml of dry dimethylacetamide, and the solution is stirred with 3.49 g of potassium carbonate overnight. The reaction mixture is poured into water and extracted with ethyl acetate. The organic phase is washed with water, dried over $MgSO_4$ and evaporated. The residue is purified by means of column chromatography on silica gel with ethyl acetate-hexane (10:90) as an eluent.

The structure is confirmed by the $^1$H-NMR spectrum ($CDCl_3$), δ1.31 (s, 6H), 2.56 (m, 4H), 3.70 (m, 4H), 4.13 (s, 2H), 5.38 (s, 1H), 5.45 (s, 1H), 7.26–7.48 (m, 7H), 8.49 (d, 2H).

EXAMPLE 5

2-{3-[4-(2-Dimethylamino-2-methyl-3-phenyl-propionyl)-phenylthio]-propylthiomethyl}-acrylic acid methyl ester (5)

5.1 1-(4-Fluorophenyl)-2-dimethylamino-2-benzyl-propan-1-one 11.2 g of sodium hydride (66% in oil) are washed with hexane to remove oil, and added to 200 ml of dry dimethylacetamide. 50.0 g (0.256 mol) of 1-(4-fluorophenyl)-2-dimethylamino-propan-1-one, prepared by the method described in U.S. Pat. No. 5,534,629, are dissolved in 50 ml of dry dimethylacetamide, and added to the above solution dropwise. Successively, 48.2 g (0.282 mol) of benzyl bromide are slowly added dropwise with stirring, and warmed up to 105° C. After the mixture is stirred at 105° C. overnight, the reaction mixture is poured to 500 ml of ice-water and extracted with toluene. The organic phase is washed with water, dried over $MgSO_4$ and evaporated. The residue is purified by means of column chromatography on silica gel with ethyl acetate-hexane (1:20) as an eluent.

The structure is confirmed by the $^1$H-NMR spectrum ($CDCl_3$), δ1.17 (s, 3H), 2.33 (s, 6H), 2.96 (d, 1H), 3.39 (d, 1H), 6.87 (m, 2H), 7.03–7.13 (m, 5H), 8.55 (m, 2H).

5.2 1-[4-(3-Mercaptopropylthio)phenyl]-2-dimethylamino-2-benzyl-propan-1-one 22.8 g (0.21 mol) of 1,3-propanedithiol are dissolved in 50 ml of dry dimethylacetamide, and the solution is heated to about 50° C. together with 4.8 g of potassium carbonate. 10.0 g of 1-(4-fluorophenyl)-2-dimethylamino-2-benzyl-propan-1-one in 50 ml of dry dimethylacetamide are added dropwise. The suspension is stirred at 50° C. overnight, then the solid is filtered off. The excesses of 1,3-propanedithiol and dimethylacetamide are distilled off. To the residue is added toluene, then the precipitate is filtered off. After toluene is distilled off, the residue is purified by means of column chromatography on silica gel with ethyl acetate-hexane (1:9) as an eluent, and an oily product is obtained.

The structure is confirmed by the $^1$H-NMR spectrum ($CDCl_3$), δ1.16 (s, 3H), 1.40 (t, 1H), 2.02 (m, 2H), 2.34 (s, 6H), 2.71 (q, 2H), 2.96 (d, 1H), 3.14 (t, 2H), 3.68 (d, 1H), 6.88 (m, 2H), 7.12 (m, 3H), 7.29 (d, 2H), 8.44 (d, 2H).

5.3 2-{3-[4-(2-Dimethylamino-2-methyl-3-phenyl-propionyl)-phenylthio]-propylthiomethyl}-acrylic acid methyl ester 1.5 g (4.0 mmol) of 1-[4-(3-mercaptopropylthio)phenyl]-2-dimethylamino-2-benzyl-propan-1-one are dissolved in 100 ml of methanol. To the solution are successively added 0.86 g (4.8 mmol) of methyl 2-(bromomethyl)acrylate and 0.55 g (4.0 mmol) of potassium carbonate, and the resulting reaction mixture is stirred at room temperature for 10 min. The reaction mixture is added to water and extracted with ethyl acetate. The organic phase is washed with water, and dried over $MgSO_4$. After distilling off the ethyl acetate, the residue is purified by means of column chromatography on silica gel with ethyl acetate-hexane (1:7) as an eluent, and an oily product is obtained.

The structure is confirmed by the $^1$H-NMR spectrum ($CDCl_3$), δ1.16 (s, 3H), 1.98 (m, 2H), 2.34 (s, 6H), 2.63 (t, 2H), 2.96 (d, 1H), 3.11 (t, 2H), 3.39 (s, 2H), 3.41 (d, 1H), 3.78 (s, 3H), 5.64 (s, 1H), 6.21 (s, 1H), 6.88 (m, 2H) 7.12 (m, 3H), 7.27 (d, 2H), 8.44 (d, 2H).

EXAMPLE 6

2-{3-[4-(2-Benzyl-2-dimethylamino-butyryl)-phenylthio]-propylthiomethyl}-acrylic acid methyl ester (6)

6.1 1-(4-Fluorophenyl)- 2-dimethylamino-2-methylpent-4-en-1-one 11.2 g of sodium hydride (66% in oil) are washed with hexane to remove oil, and added to 200 ml of dry dimethylacetamide. 50.0 g (0.256 mol) of 1-(4-fluorophenyl)-2-dimethylamino-propan-1-one, prepared by the method described in U.S. Pat. No. 5,534,629, are dissolved in 50 ml of dry dimethylacetamide, and added to the above solution dropwise. Successively, 34.1 g (0.282 mol) of benzyl bromide are slowly added dropwise with stirring, and warmed up to 105° C. After the mixture is stirred at 105° C. overnight, the reaction mixture is poured into 500 ml of ice-water and extracted with toluene. The organic phase is washed with water, dried over $MgSO_4$ and evaporated. The residue is purified by means of column chromatography on silica gel with ethyl acetate-hexane (1:9) as an eluent.

The structure is confirmed by the $^1$H-NMR spectrum ($CDCl_3$), δ1.19 (s, 3H), 2.28 (s, 6H), 2.42 (m, 1H), 2.70 (m, 1H), 4.79–4.93 (m, 2H), 5.51 (m, 1H), 7.05 (m, 2H), 8.53 (m, 2H).

6.2 1-[4-(3-Mercaptopropylthio)phenyl]-2-dimethylamino-2-methylpent-4-en-1-one 25.0 g (0.23 mol) of 1,3-propanedithiol are dissolved in 80 ml of dry dimethylacetamide, and 6.0 g of potassium carbonate are added. 10.0 g of 1-(4-fluorophenyl)-2-dimethylamino-2-methylpent-4-en-1-one in 20 ml of dry dimethylacetamide are added dropwise. The suspension is stirred at 50° C. overnight, then the solid is filtered off. The excesses of 1,3-propanedithiol and dimethylacetamide are distilled off. To the residue is added toluene, then the precipitate is filtered off. After toluene is distilled off, the residue is purified by means of column chromatography on silica gel with ethyl acetate-hexane (1:10) as an eluent, and an oily product is obtained.

The structure is confirmed by the $^1$H-NMR spectrum ($CDCl_3$), δ1.18 (s, 3H), 1.39 (t, 1H), 2.00 (m, 2H), 2.27 (s, 6H), 2.42 (m, 1H), 2.66–2.72 (m, 3H), 3.12 (t, 2H), 4.83–4.93 (m, 2H), 5.52 (m, 1H), 7.26 (d, 2H), 8.38 (d, 2H).

6.3 2-{3-[4-(2-Benzyl-2-dimethylamino-butyryl)-phenylthio]-propylthiomethyl}-acrylic acid methyl ester 1.88 g (4.8 mmol) of 1-[4-(3-mercaptopropylthio)phenyl]-2-dimethylamino-2-methylpent-4-en-1-one are dissolved in 30 ml of dry dimethylacetamide. To the solution are successively added 1.03 g (5.8 mmol) of methyl 2-(bromomethyl)acrylate and 0.66 g (4.8 mmol) of potassium carbonate, and the reaction mixture is stirred at room temperature for 10 min. The reaction mixture is then poured into water and extracted with ethyl acetate. The organic phase is washed with water, and dried over $MgSO_4$. After distilling off the ethyl acetate, the residue is purified by means of column chromatography on silica gel with ethyl acetate-hexane (1:7) as an eluent, and an oily product is obtained.

The structure is confirmed by the $^1$H-NMR spectrum ($CDCl_3$), δ0.68 (t, 3H), 1.18–1.86 (m, 1H), 1.98 (m, 2H), 2.03–2.09 (m, 1H), 2.36 (s, 6H), 2.61 (t, 2H), 3.09 (t, 2H), 3.19 (s, 2H), 3.38 (s, 2H), 3.78 (s, 3H), 5.63 (s, 1H), 6.20 (s, 1H), 7.17–7.26 (m, 7H), 8.26 (d, 2H).

EXAMPLE 7

N-{2-[4-(2-Methyl-2-morpholin-4-yl-propionyl)-phenylthio]-ethyl}-2-{3-[4-2-methyl-2-morpholin-4-yl-propionyl)-phenylthio]-propylthiomethyl}-acrylamide (7)

7.1 2-{3-[4-(2-Methyl-2-morpholin-4-yl-propionyl)-phenylthio]-propylthiomethyl}-acrylic acid 3.0 g (8.8 mmol) of 1-[4-(3-mercaptopropylthio)phenyl]-2-methyl-2-morpholin-4-yl-propane-1-one are dissolved in 70 ml of ethanol. To the solution are successively added 1.75 g (10.6 mmol) of 2-(bromomethyl)acrylic acid and 2.44 g (17.6 mmol) of potassium carbonate, and the reaction mixture is stirred at room temperature for 7 h. The reaction mixture is poured into water and neutralized with 2% hydrochloric acid solution, then extracted with ethyl acetate. The organic phase is washed with saturated sodium chloride solution, and dried over $MgSO_4$. After distilling off the ethyl acetate, the desired compound is obtained.

7.2 N-{2-[4-(2-Methyl-2-morpholin4-yl-propionyl)-phenylthio]-ethyl}-2-{3-[4-(2-morpholin-4-ylpropionyl)-phenylthio]-propylthiomethyl}-acrylamide 1.27 g (4.1 mmol) of 1-[4-(2-amino-ethylthio)-phenyl]-2-methyl-2-morpholin-4-yl-propan-1-one, 1.75 g (4.1 mmol) of 2-{3-[4-(2-Methyl-2-morpholin-4-yl-propionyl)-phenylthio]-propylthiomethyl}-acrylic acid, and 0.69 g (4.5 mmol) of 1-hydroxy-1H-benzotriazole mono-hydrate are dissolved in 50 ml of methylene chloride and cooled to −20° C. To the solution are added dropwise 0.70 g (4.5 mmol) of 1-ethyl-3-(3-dimethylaminopropyl)carbodiimide in 10 ml of methylene chloride for 1 h. The mixture is gradually warmed to room temperature and stirred overnight. After distilling off methylene chloride, ethyl acetate is added to the residue. The mixture is then washed with 2% hydrochloric acid solution, saturated sodium hydrogen carbonate solution, and saturated sodium chloride solution. The organic phase is dried over $MgSO_4$. After distilling off the ethyl acetate, the residue is purified by means of column chromatography on silica gel with ethyl acetate-hexane (2:1) as an eluent, and an oily product is obtained.

The structure is confirmed by the $^1$H-NMR spectrum ($CDCl_3$), δ1.31 (s, 12H), 1.97 (m, 2H), 2.57(m, 8H), 2.62 (t, 2H), 3.10 (t, 2H), 3.21 (t, 2H), 3.38 (s, 2H), 3.60 (q, 2H), 3.69 (m, 8H), 5.38 (s, 1H), 5.81 (s, 1H), 6.79 (br, 1H), 7.26 (d, 2H), 7.33 (d, 2H), 8.48–8.52 (m, 4H).

Determination of the chain transfer rate of the photoinitiators:

A solution of 3 mM 2,2'-azobisisobutyronitrile (AIBN) in monomer is prepared. Samples comprising 2.00 ml of AIBN solution in a 2 ml glass ample and 0.1850, 0.0925, 0.0370, 0.0185 or 0 mmol of the photoinitiator are prepared by dissolving the photoinitiator in the AIBN solution. The ample is sealed under argon flow and polymerization is carried out at 60° C. for 1 h. The reaction mixture is then poured into 100 ml of hexane to remove unreacted monomer, the formed polymer is collected by filtration and dried under vacuum over night.

The chain transfer constant of the photoinitiator is calculated by the data of number of average molecular weight (Mn) determined by GPC measurement (Gel Permeation Chromatography); calibrated with standard polystyrenes. This method is for example described in J. Chromatogr., 83, 111 (1973). The standards, of the various photoinitiators are summarized in table 1.

Molecular weight (Mw) is also determined by GPC measurement mentioned above. Mw/Mn is commonly used as an index of the molecular weight distribution of the obtained polymers and copolymers.

TABLE 1

Chain transfer rate (Ctr) of the photoinitiators for the polymerization of MMA and Styrene

| Compound | Ctr for MMA | Ctr for styrene |
|---|---|---|
| 1 | 0.53 | 0.94 |
| 2 | 0.62 | |
| 4 | 0.91 | 0.68 |
| 7 | 0.28 | |

B) Preparation of Macrophotoinitiators

EXAMPLE 8

Synthesis of Macrophotoinitiator 1 (MPI-1)

2.1 ml of MMA, 0.4 ml of toluene, containing 0.925 M of compound 1, prepared as described in Example 1, 0.5 ml of 50 mM AIBN in toluene and 2.0 ml of toluene are mixed in a 5 ml ample.

The ample is sealed under argon flow and heated in a water bath at 60° C. for 21 hrs. The reaction mixture is poured into methanol to remove unreacted monomers. The precipitated polymer is collected by filtration and dried at 30° C. under vacuum over night. The yield is 1430 mg. The number average molecular weight (Mn) is determined as 23100 by GPC measurement calibrated with standard polystyrenes; Mw/Mn=1.78.

EXAMPLE 9

Synthesis of Macrophotoinitiator 2 (MPI-2)

2.1 ml of MMA, 1 ml of toluene containing 0.925 M of compound 4, prepared as described in Example 4, 0.5 ml of 50 mM AIBN in toluene and 1.4 ml of toluene are mixed in a 5 ml ample.

The ample is sealed under argon flow and heated in a water bath at 60° C. for 21 hrs. The reaction mixture is poured into methanol to remove unreacted monomers. The precipitated polymer is collected by filtration and dried at 30° C. under vacuum over night. The yield is 735 mg. The number average molecular weight (Mn) is determined as 13300 by GPC measurement calibrated with standard polystyrenes; Mw/Mn=1.50.

EXAMPLE 10

Synthesis of Macrophotoinitiator 3 (MPI-3)

1.3 ml of MMA, 2.0 ml of toluene containing 0.925 M of compound 7, prepared as described in Example 7, 0.5 ml of 50 mM AIBN in toluene and 1.2 ml of toluene are mixed in a 5 ml ample.

The ample is sealed under argon flow and heated in a water bath at 60° C. for 21 hrs. The reaction mixture is poured into methanol to remove unreacted monomers. The precipitated polymer is collected by filtration and dried at 30° C. under vacuum over night. The yield is 775 mg. The number average molecular weight (Mn) is determined as 11300 by GPC measurement calibrated with standard polystyrenes; Mw/Mn=1.47.

EXAMPLE 11

Synthesis of Macrophotoinitiator 4 (MPI-4)

2.1 ml of styrene, 0.4 ml of toluene containing 0.925 M of compound 1, prepared as described in Example 1, 0.5 ml of 50 mM AIBN in toluene and 2.0 ml of toluene are mixed in a 5 ml ample.

The ample is sealed under argon flow and heated in a water bath at 60° C. for 21 hrs. The reaction mixture is poured into methanol to remove unreacted monomers. The precipitated polymer is collected by filtration and dried at 30° C. under vacuum over night. The yield is 407 mg. The number average molecular weight (Mn) is determined as 6400 by GPC measurement calibrated with standard polystyrenes; Mw/Mn=1.55.

EXAMPLE 12

Synthesis of Macrophotoinitiator 5 (MPI-5)

2.1 ml of styrene, 0.2 ml of toluene containing 0.925 M of compound 5, prepared as described in Example 5, 0.5 ml of 50 mM AIBN in toluene and 2.2 ml of toluene are mixed in a 5 ml ample.

The ample is sealed under argon flow and heated in a water bath at 60° C. for 21 hrs. The reaction mixture is poured into methanol to remove unreacted monomers. The precipitated polymer is collected by filtration and dried at 30° C. under vacuum over night. The yield is 505 mg. The number average molecular weight (Mn) is determined as 10700 by GPC measurement calibrated with standard polystyrenes; Mw/Mn=1.72.

EXAMPLE 13

Synthesis of Macrophotoinitiator 6 (MPI-6)

2.1 ml of styrene, 0.4 ml of toluene containing 0.925 M of compound 6, prepared as described in Example 6, 0.5 ml of 50 mM AIBN in toluene and 2.0 ml of toluene are mixed in a 5 ml ample.

The ample is sealed under argon flow and heated in a water bath at 60° C. for 21 hrs. The reaction mixture is poured into methanol to remove unreacted monomers. The precipitated polymer is collected by filtration and dried at 30° C. under vacuum over night. The yield is 372 mg. The number average molecular weight (Mn) is determined as 7800 by GPC measurement calibrated with standard polystyrenes; Mw/Mn=1.58.

C) Preparation of Block-copolymers

EXAMPLE 14

Synthesis of Block Copolymer 1 (BC-1)

50 mg of MPI-2, prepared as described in Example 9 (Mn=13300), are dissolved in 1.0 ml of styrene in an optical cell. The cell is sealed under argon flow and irradiated for 1 hour with UV lamps: twelve fluorescent lamps (Chemical lamp FL15BL made by Toshiba (360 nm, 5.8 mW/cm$^2$).

The reaction mixture is poured into methanol. The precipitated block copolymer is collected by filtration and dried under vacuum. The yield is 85 mg. The number average molecular weight (Mn) is determined as 26500 by GPC measurement calibrated with standard polystyrenes; Mw/Mn=1.83.

EXAMPLE 15

Synthesis of Block Copolymer 2 (BC-2)

50 mg of MPI-3, prepared as described in Example 10 (Mn=11300), are dissolved in 1.0 ml of styrene in an optical cell. The cell is sealed under argon flow and irradiated for 1 hr with UV lamps (360 nm, 5.8 mW/cm$^2$). The reaction mixture is poured into methanol. The precipitated block copolymer is collected by filtration and dried under vacuum. The yield is 87 mg. The number average molecular weight (Mn) is determined as 36900 by GPC measurement calibrated with standard polystyrenes; Mw/Mn=2.30.

EXAMPLE 16

Synthesis of Block Copolymer 3 (BC-3)

50 mg of MPI-4, prepared as described in Example 11 (Mn=6400), are dissolved in 1 ml of MMA in an optical cell. The cell is sealed under argon flow and irradiated for 1 hour with UV lamps (360 nm, 5.8 mW/cm$^2$). The reaction mixture is poured into hexane. The precipitated block copolymer is collected by filtration and dried under vacuum. The yield is 342 mg. The number average molecular weight (Mn) is determined as 28000 by GPC measurement calibrated with standard polystyrenes; Mw/Mn=4.37.

EXAMPLE 17

Synthesis of Block Copolymer 4 (BC-4)

50 mg of MPI-5, prepared as described in Example 12 (Mn=10700), are dissolved in 1.0 ml of MMA in an optical cell. The cell is sealed under argon flow and irradiated for 1 hr with UV lamps (360 nm, 5.8 mW/cm$^2$). The reaction mixture is poured into methanol. The precipitated block copolymer is collected by filtration and dried under vacuum. The yield is 293 mg. The number average molecular weight (Mn) is determined as 33200 by GPC measurement calibrated with standard polystyrenes; Mw/Mn=3.51.

What is claimed is:

1. Compounds of formula Ia or Ib

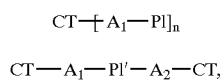

wherein n is 1 or 2;

PI is a group of formula IIa, IIb or IIc

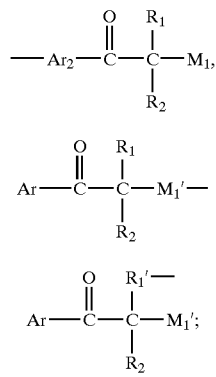

PI' is a group of formula IIIa or IIIb

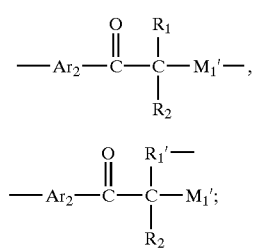

Ar is phenyl, biphenylyl or benzoylphenyl, each of which is unsubstituted or substituted 1 to 5 times by halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SR$_8$, —SOR$_8$, —SO$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of formula IV,

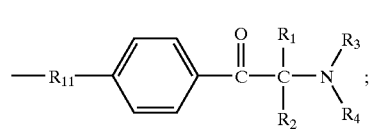

or Ar is a group of formula V or VI

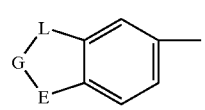

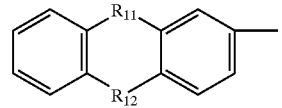

Ar$_2$ is

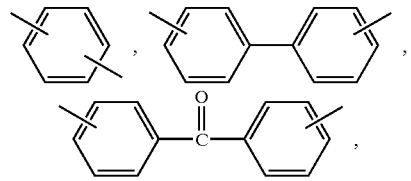

each of which is unsubstituted or substituted 1 to 5 times by halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SR$_8$, —SOR$_8$, —SO$_2$R$_8$, —CN, —SO$_2$NH$_2$, —SO$_2$NH ($C_1$–$C_4$alkyl), —SO$_2$—N($C_1$–$C_4$alkyl)$_2$, —NR$_9$R$_{10}$, —NHCOR$_9$, or by a group of formula IV;

or Ar$_2$ is a group of formula Va or VIa

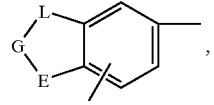

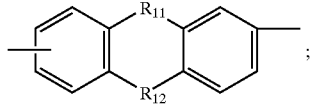

G is unbranched or branched $C_1$–$C_7$alkylene,

L and E independently of one another are a direct bond, —O—, —S— or —N(R$_6$)—, provided that L and E are not both a direct bond simultaneously;

R$_1$ and R$_2$ independently of one another are R$_7$O—; $C_1$–$C_8$alkyl, which is unsubstituted or substituted by OH, $C_1$–$C_4$alkoxy, SR$_8$, CN, ($C_1$–$C_8$alkyl)O(CO)—, ($C_1$–$C_4$alkyl)-(OC)O— or —N(R$_3$)(R$_4$); or R$_1$ and R$_2$ independently of one another are $C_3$–$C_6$alkenyl, phenyl, chlorophenyl, R$_7$—O-phenyl, R$_8$—S-phenyl or phenyl-$C_1$–$C_3$-alkyl, or R$_1$ and R$_2$ together are unbranched or branched $C_2$–$C_9$alkylene, $C_3$–$C_9$oxaalkylene or $C_3$–$C_9$azaalkylene, or R$_1$ and R$_2$ independently of one another are a radical of formula VII or VIII

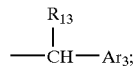

p is 0 or 1;

Ar$_3$ is phenyl, naphthyl, furyl, thienyl or pyridiyl, each of which is unsubstituted or substituted by halogen, SH, OH, $C_1$–$C_{12}$alkyl, OH-substituted $C_1$–$C_4$alkyl, halogen-substituted $C_1$–$C_4$alkyl, SH-substituted $C_1$–$C_4$alkyl, $N(R_{17})_2$-substituted $C_1$–$C_4$alkyl, $C_1$–$C_{12}$alkoxy-substituted $C_1$–$C_4$alkyl, $(C_1$–$C_{18}$alkyl)O(OC)-substituted $C_1$–$C_4$alkyl, $CH_3O(CH_2CH_2O)_m CO$-substituted $C_1$–$C_4$alkyl, $(C_1$–$C_4$alkyl)(OC)O-substituted $C_1$–$C_4$alkyl, $C_1$–$C_{12}$alkoxy, $(C_1$–$C_{18}$alkyl)(OC)O-substituted $C_1$–$C_4$alkoxy, $CH_3O(CH_2CH_2O)_m CO$-substituted $C_1$–$C_4$alkoxy, —$(OCH_2CH_2)_m OH$, —$(OCH_2CH_2)_m OCH_3$, $C_1$–$C_8$alkylthio, phenoxy, —$COO(C_1$–$C_{18}$alkyl), —$CO(OCH_2CH_2)_m OCH_3$, phenyl or benzoyl;

m is 1 to 20;

$M_1$ is —$NR_3R_4$ or —OH, or, when $R_1$ and $R_2$ are $R_7O$—, $M_1$ is Ar;

$M_1'$ is a group

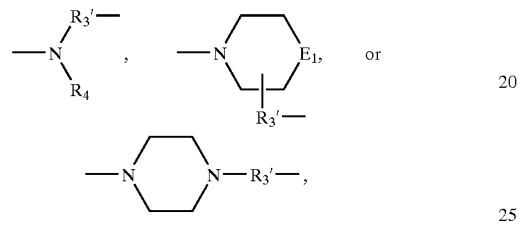

or, when $R_1$ and $R_2$ are $R_7O$—, $M_1'$ is $Ar_2$;

$R_1'$ and $R_3'$ independently of one another are a direct bond, $C_1$–$C_{12}$alkylene, or phenylene;

$E_1$ is —$CH_2$—, —O—, —$N(R_6)$— or —S—;

$R_3$ is hydrogen, $C_1$–$C_{12}$alkyl; $C_2$–$C_4$alkyl, which is substituted by OH, SH, $C_1$–$C_4$alkoxy, CN or —$COO(C_1$–$C_4$alkyl); or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl; $C_2$–$C_4$alkyl, which is substituted by OH, SH, $C_1$–$C_4$alkoxy, CN or —$COO(C_1$–$C_4$alkyl); or $R_4$ is $C_3$–$C_5$alkenyl, $C_5$–$C_{12}$-cycloalkyl, phenyl-$C_1$–$C_3$alkyl; phenyl which is unsubstituted or substituted by halogen, $C_1$–$C_{12}$alkyl, $C_1$–$C_4$alkoxy or —$COO(C_1$–$C_4$alkyl);

or $R_4$ together with $R_2$ is $C_1$–$C_7$alkylene, phenyl-$C_1$–$C_4$alkylene, o-xylylene, 2-butenylene, $C_2$–$C_3$oxaalkylene or $C_2$–$C_3$azaalkylene;

or $R_3$ and $R_4$ together are $C_3$–$C_7$alkylene, optionally interrupted by —O—, —S—, —CO— or —$N(R_6)$— and which $C_3$–$C_7$alkylene is unsubstituted or substituted by OH, SH, $C_1$–$C_4$alkoxy or —$COO(C_1$–$C_4$alkyl);

$R_6$ is hydrogen, $C_1$–$C_{12}$alkyl, OH-substituted $C_1$–$C_{12}$alkyl, SH-substituted $C_1$–$C_{12}$alkyl or HS—$(CH_2)_n$—COO-substituted $C_1$–$C_{12}$alkyl; $C_2$–$C_{12}$alkyl, which is interrupted by —O—, —NH— or —S—; or $R_6$ is $C_3$–$C_5$alkenyl, phenyl-$C_1$–$C_3$-alkyl, —$CH_2CH_2CN$, $C_1$–$C_4$alkyl-CO—$CH_2CH_2$—, OH-substituted $C_1$–$C_4$alkyl-CO—$CH_2CH_2$—, SH-substituted $C_1$–$C_4$alkyl-CO—$CH_2CH_2$—, $C_2$–$C_8$alkanoyl, OH-substituted $C_2$–$C_8$alkanoyl, SH-substituted $C_2$–$C_8$alkanoyl or benzoyl;

$R_7$ is hydrogen, $C_1$–$C_{12}$alkyl, $C_3$–$C_{12}$-alkenyl, cyclohexyl, hydroxycyclohexyl; $C_1$–$C_4$alkyl, which is mono- or polysubstituted by Cl, Br, CN, SH, —$N(C_1$–$C_4$alkyl)$_2$, piperidinyl, morpholinyl, OH, $C_1$–$C_4$alkoxy, —$OCH_2CH_2CN$, —$OCH_2CH_2COO(C_1$–$C_4$alkyl), —$O(CO)R_{19}$, —COOH, —$COO(C_1$–$C_8$alkyl), —$CONH(C_1$–$C_4$alkyl), —$CON(C_1$–$C_4$alkyl)$_2$,

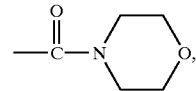

—$CO(C_1$–$C_4$alkyl) or by

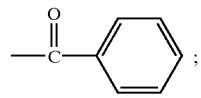

or $R_7$ is 2,3-epoxypropyl, —$(CH_2CH_2O)_n H$; phenyl which is unsubstituted or substituted by halogen, $C_1$–$C_4$alkyl, $C_1$–$C_4$alkoxy or —$COO(C_1$–$C_4$alkyl); or $R_7$ is phenyl-$C_1$–$C_3$alkyl, tetrahydropyranyl, tetrahydrofuranyl, —$COOR_{19}$, —$COO(C_1$–$C_8$alkyl), —$CONH(C_1$–$C_4$alkyl), —$CON(C_1$–$C_8$alkyl)_2$, —$Si(R_{20})(R_{21})_2$, or —$SO_2R_{22}$;

$R_8$ is hydrogen, $C_1$–$C_{12}$alkyl, $C_3$–$C_{12}$alkenyl, cyclohexyl, hydroxycyclohexyl; $C_1$–$C_4$alkyl, which is mono- or polysubstituted by Cl, Br, CN, SH, —$N(C_1$–$C_4$alkyl)$_2$, piperidinyl, morpholinyl, OH, $C_1$–$C_4$alkoxy, —$OCH_2CH_2CN$, —$OCH_2CH_2COO(C_1$–$C_4$alkyl), —$O(CO)R_{19}$, —COOH, —$COO(C_1$–$C_8$alkyl), —$CON(C_1$–$C_4$alkyl)$_2$,

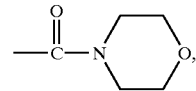

—$CO(C_1$–$C_4$alkyl) or

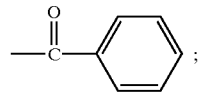

or $R_8$ is 2,3-epoxypropyl, phenyl-$C_1$–$C_3$alkyl, phenyl-$C_1$–$C_3$hydroxyalkyl; phenyl which is unsubstituted or mono- or poly-substituted by halogen, SH, $C_1$–$C_4$alkyl, $C_1$–$C_4$alkoxy or —$COO(C_1$–$C_4$alkyl); or $R_8$ is 2-benzothiazyl, 2-benzimidazolyl, —$CH_2CH_2$—O—$CH_2CH_2$—SH or —$CH_2CH_2$—S—$CH_2CH_2$—SH;

$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —$COO(C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or polysubstituted by $C_1$–$C_{12}$alkyl or halogen; or $R_9$ and $R_{10}$ together are $C_2$–$C_7$alkylene, optionally interrupted by —O—, —S—, —CO— or —$N(R_6)$—;

$R_{11}$ and $R_{12}$ independently of one another are a direct bond, —$CH_2$—, —$CH_2CH_2$—, —O—, —S—, —CO— or —$N(R_6)$—; provided that $R_{11}$ and $R_{12}$ are not a direct bond simultaneously;

$R_{13}$ is hydrogen, $C_1$–$C_8$alkyl or phenyl;

$R_{14}$, $R_{15}$ and $R_{16}$ independently of one another are hydrogen or $C_1$–$C_4$alkyl;

$R_{17}$ is hydrogen, $C_1$–$C_8$alkyl or phenyl;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl; or phenyl which is unsubstituted or substituted by $C_1$–$C_{14}$alkyl;

$A_1$ and $A_2$ independently of one another are a direct bond, —X[(CH$_2$)$_l$X']$_q$—[(C$_6$H$_4$)$_o$X"]$_r$—, —O—, —S— or —N(R$_6$)—;

X, X' and X" independently of each other are a direct bond, —O—, —S—, —N(R$_6$)—, —O(CO)—, —COO— —NHCO—, —CONH— or —CO—;

l is an integer from 0 to 10;

q is an integer from 0 to 5:

o and r independently of one another are an integer 0, 1 or 2;

CT when n is 1, is a group of formula IXa, IXb, Xa or Xb,

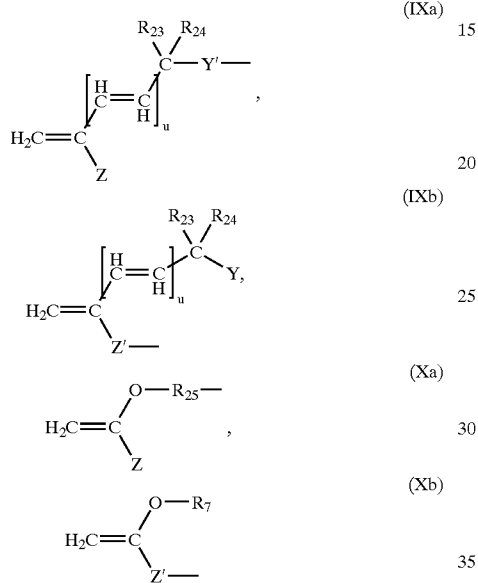

or, when n is 2, CT is a group of formula XI and XII,

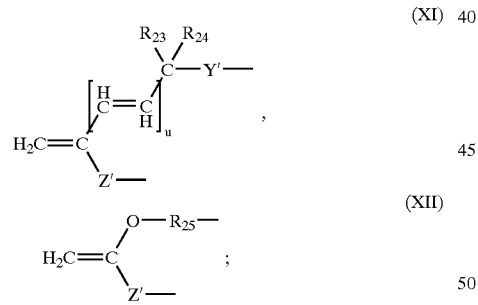

Y is —W(R$_8$)$_s$;

Y' is —W(R$_8$)$_t$—R$_{25}$—;

W is S, Si, Se, P, Br, Cl, Sn, —O—O—, S(=O), S(=O)$_2$, or P(=O);

Z is —COOR$_7$, —CONR$_9$R$_{10}$, —CN, or —Ar;

Z' is —COOR$_{25}$—, —CONR$_9$R$_{25}$—, or —Ar$_2$—;

s is an integer from 0 to 3;

t is an integer 0, 1 or 2;

u is 0 or 1;

$R_{23}$ and $R_{24}$ independently of one another are hydrogen, or $C_1$–$C_8$alkyl; or $R_{23}$ and $R_{24}$ together are $C_5$–$C_7$cyloalkyl; and $R_{25}$ is a direct bond, $C_1$–$C_4$alkylene or phenylene.

2. Compounds according to claim 1 of formula Ia, wherein when n is 1, CT is a group of formula IXa or IXb and when n is 2, CT is a group of formula XI.

3. Compounds according to claim 2, wherein PI is a group of formula IIa;

Ar$_2$ is

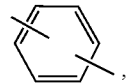

which is unsubstituted or substituted 1 to 4 times by halogen, $C_1$–$C_{12}$alkyl, or —OR$_7$;

$R_1$ and $R_2$ independently of one another are $C_1$–$C_8$alkyl, which is unsubstituted or substituted by OH, or $C_1$–$C_4$alkoxy, or $R_1$ and $R_2$ independently of one another are $C_3$–$C_6$alkenyl, phenyl, chlorophenyl, or phenyl-$C_1$–$C_3$-alkyl or $R_1$ and $R_2$ independently of one another are a radical of formula VII or VIII;

Ar$_3$ is phenyl;

M$_1$ is —NR$_3$R$_4$;

$R_3$ is hydrogen, $C_1$–$C_{12}$alkyl; or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl; or $R_3$ and $R_4$ together are $C_3$–$C_7$alkylene, optionally interrupted by —O—;

$R_7$ is hydrogen, or $C_1$–$C_{12}$alkyl;

$R_{13}$, $R_{14}$, $R_{15}$ and $R_{16}$ are hydrogen;

$A_1$ is a direct bond, —X[(CH$_2$)$_l$X']$_q$—[(C$_6$H$_4$)$_o$X"]$_r$—, —O—, —S— or —N(R$_6$)—;

$R_6$ is hydrogen or $C_1$–$C_{12}$alkyl;

X, X' and X" independently of each other are a direct bond, —O—, —S—, or —N(R$_6$)—;

l is an integer from 0 to 4;

q is an integer 0 or 1;

CT when n is 1, is a group of formula IXa or IXb or, when n is 2, CT is a group of formula XI;

Y is —W(R$_8$)$_s$;

Y' is —W(R$_8$)$_t$R$_{25}$—;

W is S;

$R_8$ is hydrogen or $C_1$–$C_{12}$alkyl;

Z is —COOR$_7$, —CONR$_9$R$_{10}$, or —Ar;

$R_9$ and $R_{10}$ are independently of each other are hydrogen or $C_1$–$C_{12}$alkyl;

Ar is phenyl;

Z' is —COOR$_{25}$— or —CONR$_9$R$_{25}$—;

u and t are 0;

s is 1;

$R_{23}$ and $R_{24}$ are hydrogen; and $R_{25}$ is a direct bond or $C_1$–$C_4$ alkylene.

4. Macrophotoinitiator obtained by thermally polymerizing a monomer and a photoinitiator compound of formula Ia or Ib according to claim 1.

5. Macrophotoinitiator according to claim 4, wherein the monomer is of formula XIII

wherein $X_1$ is —CN, —OSi(R$_{26}$)$_3$, —R$_{27}$, —OR$_{28}$, —SR$_{28}$, —NR$_{29}$R$_{30}$,

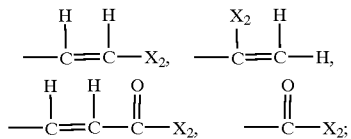

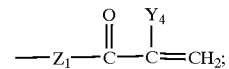

or X₁ is phenyl or benzyl each of which is unsubstituted or substituted by halogen, $C_1$–$C_{12}$alkyl, $C_1$–$C_{12}$alkoxy, $C_3$–$C_8$cycloalkyl, —COOH, —COO($C_1$–$C_{12}$-alkyl), —O(CO)O($C_1$–$C_{12}$alkyl), tetrahydropyranyloxy, tetrahydrofuranyloxy, or tetrahydrofurfuryloxy;

$Y_1$, $Y_2$ and $Y_3$ independently of one another are hydrogen, $C_1$–$C_4$alkyl, halogen, —CN or —COOR₇; or $Y_1$ and $Y_3$ together are $C_3$–$C_7$alkylene, optionally interrupted by —O—, —S—, —CO— or —N($R_6$)— and which $C_3$–$C_7$alkylene is unsubstituted or substituted by OH, $C_1$–$C_4$alkoxy or —COO($C_1C_4$alkyl);

$X_2$ is —OSi($R_{26}$)₃, —$R_{27}$, —O$R_{28}$, —S$R_{28}$, —N$R_{29}R_{30}$;

$R_{26}$ independently of one another are hydrogen; $C_1$–$C_{20}$alkyl, $C_3$–$C_{12}$-alkenyl, $C_3$–$C_8$cycloalkyl, $C_4$–$C_8$cycloalkenyl, each of which is unsubstituted or mono- or polysubstituted by F, Cl, Br, CN, —N($C_1$–$C_4$alkyl)₂, piperidino, morpholino, OH, $C_1$–$C_4$alkoxy, —OCH₂CH₂CN, —OCH₂CH₂COO($C_1$–$C_4$alkyl), —O(CO)$R_{19}$, —COOH, —COO($C_1$–$C_8$alkyl), —CONH($C_1$–$C_4$alkyl), —CON($C_1$–$C_4$alkyl)₂, —CO($C_1$–$C_4$alkyl) or by

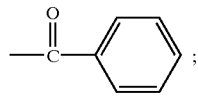

or $R_{26}$ is 2,3-epoxypropyl, —(CH₂CH₂O)$_m$H or —(CH₂CH₂O)$_m$$R_{19}$;

or $R_{26}$ is phenyl, pyridinyl, biphenylyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, or —COO($C_1$–$C_{12}$alkyl); or $R_{26}$ is phenyl-$C_1$–$C_3$alkyl, OR₇, —NR₉R₁₀, or —NHCOR₉;

$R_{27}$ is hydrogen; $C_1$–$C_{20}$alkyl, $C_3$–$C_{12}$-alkenyl, $C_3$–$C_8$cycloalkyl, $C_4$–$C_8$cycloalkenyl each of which is unsubstituted or mono- or polysubstituted by F, Cl, Br, CN, —N($C_1$–$C_4$alkyl)₂, phenyl, phenoxy, piperidino, morpholino, OH, $C_1$–$C_4$alkoxy, —OCH₂CH₂CN, —OCH₂CH₂COO($C_1$–$C_4$-alkyl), —O(CO)$R_{19}$, —COOH, —COO($C_1$–$C_8$alkyl), —CONH($C_1$–$C_4$alkyl), —CON($C_1$–$C_4$alkyl)₂, —CO($C_1$–$C_4$alkyl) or by

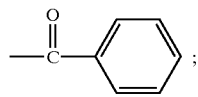

or $R_{27}$ is 2,3-epoxypropyl, or —(CH₂CH₂O)$_m$H;

or $R_{27}$ is phenyl, pyridinyl, biphenylyl, benzyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, —COO($C_1$–$C_{12}$alkyl), —O(CO)O($C_1$–$C_{12}$alkyl), tetrahydropyranyloxy, tetrahydrofuranyloxy, or tetrahydrofurfuryloxy;

or $R_{27}$ is phenyl-$C_1$–$C_3$alkyl, tetrahydropyranyl, tetrahydrofuranyl, adamantyl, camphoryl; and optionally $R_{27}$ contains one or more reactive substituents of formula

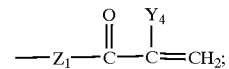

$R_{28}$ is hydrogen; $C_1$–$C_{20}$alkyl, $C_3$–$C_{12}$-alkenyl, $C_3$–$C_8$cycloalkyl, $C_4$–$C_8$cycloalkenyl each of which is unsubstituted or mono- or polysubstituted by F, Cl, Br, CN, —N($C_1$–$C_4$alkyl)₂, phenyl, phenoxy, piperidino, morpholino, OH, $C_1$–$C_4$alkoxy, —OCH₂CH₂CN, —OCH₂CH₂COO($C_1$–$C_4$-alkyl), —O(CO)$R_{19}$, —COOH, —COO($C_1$–$C_8$alkyl), —CONH($C_1$–$C_4$alkyl), —CON($C_1$–$C_4$alkyl)₂, —CO($C_1$–$C_4$alkyl) or by

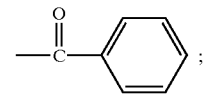

or $R_{28}$ is 2,3-epoxypropyl, or —(CH₂CH₂O)$_m$H;

or $R_{28}$ is phenyl, pyridinyl, biphenylyl, benzyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, —COO($C_1$–$C_{12}$alkyl), —O(CO)O($C_1$–$C_{12}$alkyl), tetrahydropyranyloxy, tetrahydrofuranyloxy, or tetrahydrofurfuryloxy;

or $R_{28}$ is phenyl-$C_1$–$C_3$alkyl, tetrahydropyranyl, tetrahydrofuranyl, adamantyl, camphoryl; and optionally $R_{28}$ contains one or more reactive substituents of formula

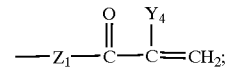

$R_{29}$ and $R_{30}$ independently of one another are hydrogen; $C_1$–$C_{12}$alkyl, or $C_2$–$C_4$alkyl each of which is substituted by OH, $C_1$–$C_4$alkoxy, CN or +COO($C_1$–$C_4$alkyl);

or $R_{29}$ and $R_{30}$ independently of one another are $C_3$–$C_5$alkenyl, cyclohexyl, phenyl-$C_1$–$C_3$alkyl, adamantyl, camphoryl unsubstituted phenyl or phenyl which is mono- or poly-substituted by $C_1$–$C_{12}$alkyl or halogen;

or $R_{29}$ and $R_{30}$ together are $C_2$–$C_7$alkylene optionally interrupted by —O—, —S— or —N($R_6$)—;

$Y_4$ is hydrogen or CH₃;

$Z_1$ is —O— or —N($R_{28}$)—;

$R_6$ is hydrogen, $C_1$–$C_{12}$alkyl, OH-substituted $C_1$–$C_{12}$alkyl, SH-substituted $C_1$–$C_{12}$alkyl or HS—(CH₂)$_n$—COO-substituted $C_1$–$C_{12}$alkyl; $C_2$–$C_{12}$alkyl, which is interrupted by —O—, —NH— or —S—; or $R_6$ is $C_3$–$C_5$alkenyl, phenyl-$C_1$–$C_3$-alkyl, —CH₂CH₂CN, $C_1$–$C_4$alkyl-CO—CH₂CH₂—, OH-substituted $C_1$–$C_4$alkyl-CO—CH₂CH₂—, SH-substituted $C_1$–$C_4$alkyl-CO—CH₂CH₂—, $C_2$–$C_8$alkanoyl, OH-substituted $C_2$–$C_8$alkanoyl, SH-substituted $C_2$–$C_8$alkanoyl or benzoyl; and n is 1 or 2.

6. Macrophotoinitiator according to claim 5 of formula XIII, wherein
$X_1$ is —CN, or

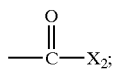

or $X_1$ is phenyl or benzyl each of which is unsubstituted or substituted by halogen, $C_1$-$C_{12}$alkyl, $C_1$-$C_{12}$alkoxy, $C_3$-$C_8$cycloalkyl, —COOH, —COO($C_1$-$C_{12}$alkyl), —O(CO)O($C_1$-$C_{12}$alkyl), tetrahydropyranyloxy, tetrahydrofuranyloxy, or tetrahydrofurfuryloxy;
$Y_1$ and $Y_2$ are hydrogen;
$Y_3$ is hydrogen or $C_1$-$C_4$ alkyl;
$X_2$ is —O$R_{28}$ or —N$R_{29}R_{30}$.

7. Macrophotoinitiator according to claim 4, which is of formula XIV

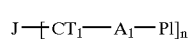  (XIV), wherein
n is 1 or 2;
PI is a photoinitiator moiety
$CT_1$ is —Y'—, —$R_{25}$—,

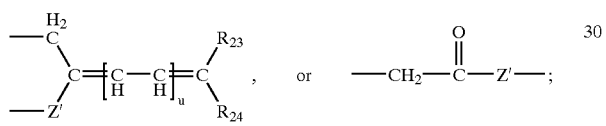

u is 0 or 1;
J is a polymeric group;
$A_1$ is a direct bond, —X[(CH$_2$)$_l$X']$_q$—[(C$_6$H$_4$)$_o$X"]$_r$—, —O—, —S— or —N(R$_6$)—;
X, X' and X" independently of each other are a direct bond, —O—, —S—, —N(R$_6$)—, —O(CO)—, —COO—, —NHCO—, —CONH— or —CO—;
l is an integer from 0 to 10;
q is an integer from 0 to 5;
o and r independently of one another are an integer 0, 1 or 2;
Z' is —COO$R_{25}$—, —CONR$_9$R$_{25}$—, or —Ar$_2$—;
Y' is —W(R$_8$)$_t$—R$_{25}$—;
t is an integer 0, 1 or 2;
W is S, Si, Se, P, Br, Cl, Sn, —O—O—, S(=O), S(=O)$_2$, or P(=O);
$Ar_2$ is

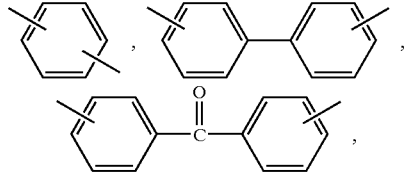

each of which is unsubstituted or substituted 1 to 5 times by halogen, $C_1$-$C_{12}$alkyl, $C_3$-$C_{12}$alkenyl, $C_5$-$C_6$cycloalkyl, phenyl-$C_1$-$C_3$alkyl, —COOH, —COO($C_1$-$C_4$alkyl), —OR$_7$, —SR$_8$, —SOR$_8$, —SO$_2$R$_8$, —CN, —SO$_2$NH$_2$, —SO$_2$NH($C_1$-$C_4$alkyl), —SO$_2$—N($C_1$-$C_4$alkyl)$_2$, —NR$_9$R$_{10}$, —NHCOR$_9$, or by a group of formula IV

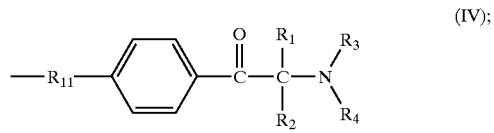  (IV);

or $Ar_2$ is a group of formula Va or VIa

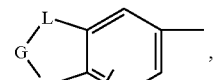  (Va)

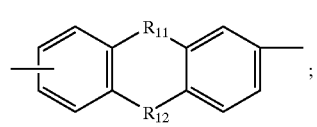  (VIa);

G is unbranched or branched $C_1$-$C_7$alkylene;
L and E independently of one another are a direct bond, —O—, —S— or —N(R$_6$)—, provided that L and E are not both a direct bond simultaneously;
$R_1$ and $R_2$ independently of one another are $R_7$O—, $C_1$-$C_8$alkyl, which is unsubstituted or substituted by OH, $C_1$-$C_4$alkoxy, SR$_8$, CN, ($C_1$-$C_8$alkyl)O(CO)—, ($C_1$-$C_4$alkyl)-(OC)O— or —N(R$_3$)(R$_4$), or $R_1$ and $R_2$ independently of one another are $C_3$-$C_6$alkenyl, phenyl, chlorophenyl, $R_7$—O-phenyl, $R_8$—S-phenyl or phenyl-$C_1$-$C_3$-alkyl, or $R_1$ and $R_2$ together are unbranched or branched $C_2$-$C_9$alkylene, $C_3$-$C_9$oxaalkylene or $C_3$-$C_9$azaalkylene, or $R_1$ and $R_2$ independently of one another are a radical of formula VII or VIII

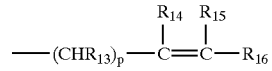  (VII)

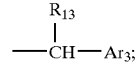  (VIII)

$Ar_3$ is phenyl, naphthyl, furyl, thienyl or pyridiyl, each of which is unsubstituted or substituted by halogen, SH, OH, $C_1$-$C_{12}$alkyl, OH-substituted $C_1$-$C_4$alkyl, halogen-substituted $C_1$-$C_4$alkyl, SH-substituted $C_1$-$C_4$alkyl, N(R$_{17}$)$_2$-substituted $C_1$-$C_4$alkyl, $C_1$-$C_{12}$alkoxy-substituted $C_1$-$C_4$alkyl, ($C_1$-$C_{18}$alkyl)O(OC)-substituted $C_1$-$C_4$alkyl, CH$_3$O(CH$_2$CH$_2$O)$_m$CO-substituted $C_1$-$C_4$alkyl, ($C_1$-$C_4$alkyl)(OC)O-substituted $C_1$-$C_4$alkyl, $C_1$-$C_{12}$alkoxy, ($C_1$-$C_{18}$alkyl)(OC)O-substituted $C_1$-$C_4$-alkoxy, CH$_3$O(CH$_2$CH$_2$O)$_m$CO-substituted $C_1$-$C_4$alkoxy, —(OCH$_2$CH$_2$)$_m$OH, —(OCH$_2$CH$_2$)$_m$OCH$_3$, $C_1$-$C_8$alkylthio, phenoxy, —COO ($C_1$–$C_{18}$alkyl), —CO(OCH$_2$CH$_2$)$_m$OCH$_3$, phenyl or benzoyl;

m is 1 to 20;

$R_3$ is hydrogen, $C_1$–$C_{12}$alkyl, $C_2$–$C_4$alkyl, which is substituted by OH, SH, $C_1$–$C_4$alkoxy, CN or —COO($C_1$–$C_4$alkyl); or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl; $C_2$–$C_4$alkyl, which is substituted by OH, SH, $C_1$–$C_4$alkoxy, CN or —COO($C_1$–$C_4$alkyl); or $R_4$ is $C_3$–$C_5$alkenyl, $C_5$–$C_{12}$-cycloalkyl, phenyl-$C_1$–$C_3$alkyl; phenyl which is unsubstituted or substituted by halogen, $C_1$–$C_{12}$alkyl, $C_1$–$C_4$alkoxy or —COO($C_1$–$C_4$alkyl);

or $R_4$ together with $R_2$ is $C_1$–$C_7$alkylene, phenyl-$C_1$–$C_4$alkylene, o-xylylene, 2-butenylene, $C_2$–$C_3$oxaalkylene or $C_2$–$C_3$azaalkylene;

or $R_3$ and $R_4$ together are $C_3$–$C_7$alkylene, optionally interrupted by —O—, —S—, —CO— or —N($R_6$)— and which $C_3$–$C_7$alkylene is unsubstituted or substituted by OH, SH, $C_1$–$C_4$alkoxy or —COO($C_1$–$C_4$alkyl);

$R_6$ is hydrogen, $C_1$–$C_{12}$alkyl, OH-substituted $C_1$–$C_{12}$alkyl, SH-substituted $C_1$–$C_{12}$alkyl or HS—(CH$_2$)$_n$—COO-substituted $C_1$–$C_{12}$alkyl; $C_2$–$C_{12}$alkyl, which is interrupted by —O—, —N— or —S—;

or $R_6$ is $C_3$–$C_5$alkenyl, phenyl-$C_1$–$C_3$-alkyl, —CH$_2$CH$_2$CN, $C_1$–$C_4$alkyl-CO—CH$_2$CH$_2$—, OH-substituted $C_1$–$C_4$alkyl-CO—CH$_2$CH$_2$—, SH-substituted $C_1$–$C_4$alkyl-CO—CH$_2$CH$_2$—, $C_2$–$C_8$alkanoyl, OH-substituted $C_2$–$C_8$alkanoyl, SH-substituted $C_2$–$C_8$alkanoyl or benzoyl;

$R_7$ is hydrogen, $C_1$–$C_{12}$alkyl, $C_3$–$C_{12}$-alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidinyl, morpholinyl, OH, $C_1$–$C_4$alkoxy, —OCH$_2$CH$_2$CN, —OCH$_2$CH$_2$COO($C_1$–$C_4$alkyl), —O(CO)$R_{19}$, —COOH, —COO($C_1$–$C_8$alkyl), —CONH($C_1$–$C_4$alkyl), —CON($C_1$–$C_4$alkyl)$_2$,

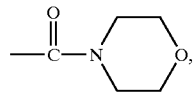

—CO($C_1$–$C_4$alkyl) or by

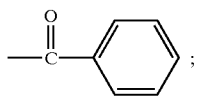

;

or $R_7$ is 2,3-epoxypropyl, —(CH$_2$CH$_2$O)$_n$H; phenyl which is unsubstituted or substituted by halogen, $C_1$–$C_4$alkyl, $C_1$–$C_4$alkoxy or —COO($C_1$–$C_4$alkyl); or $R_7$ is phenyl-$C_1$–$C_3$alkyl, tetrahydropyranyl, tetrahydrofuranyl, —COO$R_{19}$, —COO($C_1$$C_8$alkyl), —CONH($C_1$–$C_4$-alkyl), —CON($C_1$–$C_8$alkyl)$_2$, —Si($R_{20}$)($R_{21}$)$_2$, or —SO$_2$$R_{22}$;

$R_8$ is hydrogen, $C_1$–$C_{12}$alkyl, $C_3$–$C_{12}$alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidinyl, morpholinyl, OH, $C_1$–$C_4$alkoxy, —OCH$_2$CH$_2$CN, —OCH$_2$CH$_2$COO($C_1$–$C_4$alkyl), —O(CO)$R_{19}$, —COOH, —COO($C_1$–$C_8$alkyl), —CON($C_1$–$C_4$alkyl)$_2$,

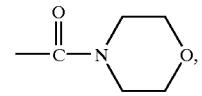

—CO($C_1$–$C_4$alkyl) or

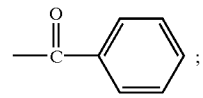

;

or $R_8$ is 2,3-epoxypropyl, phenyl-$C_1$–$C_3$alkyl, phenyl-$C_1$–$C_3$hydroxyalkyl; phenyl which is unsubstituted or mono- or poly-substituted by halogen, SH, $C_1$–$C_4$alkyl, $C_1$–$C_4$alkoxy or —COO($C_1$–$C_4$alkyl); or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or poly-substituted by $C_1$–$C_{12}$alkyl or halogen; or $R_9$ and $R_{10}$ together are $C_2$–$C_7$alkylene, optionally interrupted by —O—, —S— or —N($R_6$)—;

$R_{11}$ and $R_{12}$ independently of one another are a direct bond, —CH$_2$—, —CH$_2$CH$_2$—, —O—, —S—, —CO— or —N($R_6$)—; provided that $R_{11}$ and $R_{12}$ are not a direct bond simultaneously;

$R_{13}$ is hydrogen, $C_1$–$C_8$alkyl or phenyl;

$R_{14}$, $R_{15}$ and $R_{16}$ independently of one another are hydrogen or $C_1$–$C_4$alkyl;

$R_{17}$ is hydrogen, $C_1$–$C_8$alkyl or phenyl;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl; or phenyl which is unsubstituted or substituted by $C_1$–$C_{14}$alkyl;

$R_{23}$ and $R_{24}$ independently of one another are hydrogen, or $C_1$–$C_8$alkyl; or $R_{23}$ and $R_{24}$ together are $C_5$–$C_7$cyloalkyl; and $R_{25}$ is a direct bond, $C_1$–$C_4$alkylene or phenylene.

8. Macrophotoinitiator according to claim 7 of formula XIV, wherein

PI is a group of formula IIa

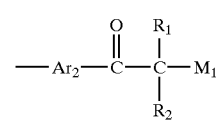

(IIa);

$CT_1$ is —Y'—, —$R_{25}$— or

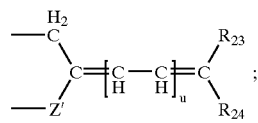

u and t are 0;
l is an integer from 0 to 4;
q is an integer 0 or 1;
o and r independently of one another are an integer 0, 1 or 2;
Z' is —$COOR_{25}$— or —$CONR_9R_{25}$—;
Y' is —$W(R_8)_t$—$R_{25}$—;
W is S;
$Ar_2$ is

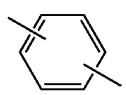

which is unsubstituted or substituted 1 to 4 times by halogen, $C_1$–$C_{12}$alkyl or —$OR_7$;
$R_1$ and $R_2$ independently of one another are $C_1$–$C_8$alkyl which is unsubstituted or substituted by OH, or $C_1$–$C_4$alkoxy; or $R_1$ and $R_2$ independently of one another are $C_3$–$C_6$alkenyl, phenyl, chlorophenyl, or phenyl-$C_1$–$C_3$-alkyl; or $R_1$ and $R_2$ independently of one another are a radical of formula VII or VIII;
$Ar_3$ is phenyl;
$M_1$ is —$NR_3R_4$;
$R_3$ is hydrogen, $C_1$–$C_{12}$alkyl, $C_3$–$C_5$alkenyl, $C_5$–$C_{12}$cycloalkyl or phenyl-$C_1$–$C_3$alkyl;
$R_4$ is $C_1$–$C_{12}$alkyl; or $R_3$ and $R_4$ together are $C_3$–$C_7$alkylene, optionally interrupted by —O—;
$R_6$, $R_7$, $R_8$ and $R_9$ independently of each other are hydrogen or $C_1$–$C_{12}$alkyl;
$R_{13}$, $R_{14}$, $R_{15}$, $R_{16}$, $R_{23}$ and $R_{24}$ are hydrogen; and
$R_{25}$ is a direct bond, or $C_1$–$C_4$alkylene.

9. Process for the preparation of a macrophotoinitiator according to claim 7, characterized in that a photoinitiator with a chain transfer group is thermally polymerized with a monomer.

10. Photopolymerizable composition comprising
(A) at least one ethylenically unsaturated photopolymerizable compound and
(B) at least one macrophotoinitiator according to claim 4.

11. Photopolymerizable composition according to claim 10, which additionally to the component (B) comprises at least one further photoinitiator (C), and/or further coinitiators (D) and/or other additives (E).

12. Block-copolymer obtained by photopolymerizing monomers of formula XIII

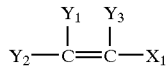

(XIII), wherein
$X_1$ is —CN, —$OSi(R_{26})_3$, —$R_{27}$, —$OR_{28}$, —$SR_{28}$, —$NR_{29}R_{30}$,

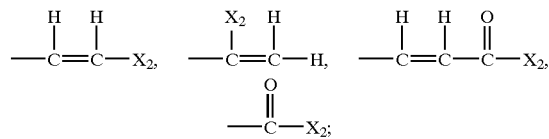

or $X_1$ is phenyl or benzyl each of which is unsubstituted or substituted by halogen, $C_1$–$C_{12}$alkyl, $C_1$–$C_{12}$alkoxy, $C_3$–$C_8$cycloalkyl, —COOH, —COO($C_1$–$C_{12}$alkyl), —O(CO)O($C_1$–$C_{12}$alkyl), tetrahydropyranyloxy, tetrahydrofuranyloxy, or tetrahydrofurfuryloxy;
$Y_1$, $Y_2$ and $Y_3$ independently of one another are hydrogen, $C_1$–$C_4$alkyl, halogen, —CN or —$COOR_7$; or $Y_1$ and $Y_3$ together are $C_3$–$C_7$alkylene, optionally interrupted by —O—, —S—, —CO— or —N($R_6$)— and which $C_3$–$C_7$alkylene is unsubstituted or substituted by OH, $C_1$–$C_4$alkoxy or —COO($C_1$–$C_4$alkyl);
$X_2$ is —$OSi(R_{26})_3$, —$R_{27}$, —$OR_{28}$, —$SR_{28}$, —$NR_{29}R_{30}$;
$R_{26}$ independently of one another are hydrogen; $C_1$–$C_{20}$alkyl, $C_3$–$C_{12}$-alkenyl, $C_3$–$C_8$cycloalkyl, $C_4$–$C_8$cycloalkenyl, each of which is unsubstituted or mono- or polysubstituted by F, Cl, Br, CN, —N($C_1$–$C_4$alkyl)$_2$, piperidino, morpholino, OH, $C_1$–$C_4$alkoxy, —$OCH_2CH_2CN$, —$OCH_2CH_2COO$($C_1$–$C_4$alkyl), —$O(CO)R_{19}$, —COOH, —COO($C_1$–$C_8$alkyl), —CONH($C_1$–$C_4$alkyl), —CON($C_1$–$C_4$alkyl)$_2$, —CO($C_1$–$C_4$alkyl) or by

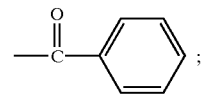

or $R_{26}$ is 2,3-epoxypropyl, —$(CH_2CH_2O)_m$H or —$(CH_2CH_2O)_mR_{19}$;
or $R_{26}$ is phenyl, pyridinyl, biphenylyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, or —COO($C_1$–$C_{12}$alkyl);
or $R_{26}$ is phenyl-$C_1$–$C_3$alkyl, $OR_7$, —$NR_9R_{10}$, or —$NHCOR_9$;
$R_{27}$ is hydrogen; $C_1$–$C_{20}$alkyl, $C_3$–$C_{12}$-alkenyl, $C_3$–$C_8$cycloalkyl, $C_4$–$C_8$ cycloalkenyl each of which is unsubstituted or mono- or polysubstituted by F, Cl, Br, CN, —N($C_1$–$C_4$alkyl)$_2$, phenyl, phenoxy, piperidino, morpholino, OH, $C_1$–$C_4$alkoxy, —$OCH_2CH_2CN$, —$OCH_2CH_2COO$($C_1$–$C_4$alkyl), —$O(CO)R_{19}$, —COOH, —COO($C_1$–$C_8$alkyl), —CONH($C_1$–$C_4$alkyl), —CON($C_1$–$C_4$alkyl)$_2$, —CO($C_1$–$C_4$alkyl) or by

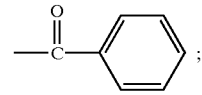

or $R_{27}$ is 2,3-epoxypropyl, or —$(CH_2CH_2O)_m$ H;
or $R_{27}$ is phenyl, pyridinyl, biphenylyl, benzyl or benzoylphenyl each of which is unsubstituted or mono- or polysubstituted by halogen, $C_1$–$C_{12}$alkyl, $C_1$–$C_{12}$alkoxy, $C_3$–$C_8$cycloalkyl, —COOH, —COO($C_1$–$C_{12}$alkyl), —O(CO)O($C_1$–$C_{12}$alkyl), tetrahydropyranyloxy, tetrahydrofuranyloxy, or tetrahydrofurfuryloxy;

or $R_{27}$ is phenyl-$C_1$-$C_3$alkyl, tetrahydropyranyl, tetrahydrofuranyl, adamantyl, camphoryl; and optionally $R_{27}$ contains one or more reactive substituents of formula $$-Z_1-\overset{O}{\underset{\|}{C}}-\overset{Y_4}{\underset{|}{C}}=CH_2;$$

$R_{28}$ is hydrogen; $C_1$-$C_{20}$alkyl, $C_3$-$C_{12}$-alkenyl, $C_3$-$C_8$cycloalkyl, $C_4$-$C_8$cycloalkenyl each of which is unsubstituted or mono- or polysubstituted by F, Cl, Br, CN, —N($C_1$-$C_4$alkyl)$_2$, phenyl, phenoxy, piperidino, morpholino, OH, $C_1$-$C_4$alkoxy, —OCH$_2$CH$_2$CN, —OCH$_2$CH$_2$COO($C_1$-$C_4$alkyl), —O(CO)R$_{19}$, —COOH, —COO($C_1$-$C_8$alkyl), —CONH($C_1$-$C_4$alkyl), —CON($C_1$-$C_4$alkyl)$_2$, —CO($C_1$-$C_4$alkyl) or by

[structure: —C(=O)-phenyl]

or $R_{28}$ is 2,3-epoxypropyl, or —(CH$_2$CH$_2$O)$_m$H;

or $R_{28}$ is phenyl, pyridinyl, biphenylyl, benzyl or benzoylphenyl each of which is unsubstituted or mono- or polysubstituted by halogen, $C_1$-$C_{12}$alkyl, $C_1$-$C_{12}$alkoxy, $C_3$-$C_8$cycloalkyl, —COOH, —COO ($C_1$-$C_{12}$alkyl), —O(CO)O($C_1$-$C_{12}$alkyl), tetrahydropyranyloxy, tetrahydrofuranyloxy, or tetrahydrofurfuryloxy; or $R_{28}$ is phenyl-$C_1$-$C_3$alkyl, tetrahydropyranyl, tetrahydrofuranyl, adamantyl, camphoryl; and optionally $R_{28}$ contains one or more reactive substituents of formula $$-Z_1-\overset{O}{\underset{\|}{C}}-\overset{Y_4}{\underset{|}{C}}=CH_2;$$

$R_{29}$ and $R_{30}$ independently of one another are hydrogen; $C_1$-$C_{12}$alkyl, or $C_2$-$C_4$alkyl each of which is substituted by OH, $C_1$-$C_4$alkoxy, CN or —COO ($C_1$-$C_4$alkyl);

or $R_{29}$ and $R_{30}$ independently of one another are $C_3$-$C_5$alkenyl, cyclohexyl, phenyl-$C_1$-$C_3$alkyl, adamantyl, camphoryl unsubstituted phenyl or phenyl which is mono- or poly-substituted by $C_1$-$C_{12}$alkyl or halogen;

or $R_{29}$ and $R_{30}$ together are $C_2$-$C_7$alkylene optionally interrupted by —O—, —S— or —N(R$_6$)—;

$Y_4$ is hydrogen or CH$_3$;

$Z_1$ is —O— or —N(R$_{28}$)—;

$R_6$ is hydrogen, $C_1$-$C_{12}$alkyl, OH-substituted $C_1$-$C_{12}$alkyl, SH-substituted $C_1$-$C_{12}$alkyl or HS—(CH$_2$)$_n$—COO-substituted $C_1$-$C_{12}$alkyl; $C_2$-$C_{12}$alkyl, which is interrupted by —O—, —NH— or —S—; or $R_6$ is $C_3$-$C_5$alkenyl, phenyl-$C_1$-$C_3$-alkyl, —CH$_2$CH$_2$CN, $C_1$-$C_4$alkyl-CO—CH$_2$CH$_2$—, OH-substituted $C_1$-$C_4$alkyl-CO—CH$_2$CH$_2$—, SH-substituted $C_1$-$C_4$alkyl-CO—CH$_2$CH$_2$—, $C_2$-$C_8$alkanoyl, OH-substituted $C_2$-$C_8$alkanoyl, SH-substituted $C_2$-$C_8$alkanoyl or benzoyl; and n is 1 or 2 and a macrophotoinitiator obtained by thermally polymerizing a monomer and a photoinitiator compound of formula Ia or Ib according to claim 1.

13. Block copolymer according to claim 12, which is of formula XV $$J-[CT_1-A_1-Ar_2-\overset{O}{\underset{\|}{C}}]_n-J_1 \quad (XV),$$

wherein n is 1 or 2;

Ar$_2$ is

[structures: phenyl, biphenyl, and benzophenone-type groups]

each of which is unsubstituted or substituted 1 to 5 times by halogen, $C_1$-$C_{12}$alkyl, $C_3$-$C_{12}$alkenyl, $C_5$-$C_6$cycloalkyl, phenyl-$C_1$-$C_3$alkyl, —COOH, —COO($C_1$-$C_4$alkyl), —OR$_7$, —SR$_8$, —SOR$_8$, —SO$_2$R$_8$, —CN, —SO$_2$NH$_2$, —SO$_2$NH($C_1$-$C_4$alkyl), —SO$_2$—N($C_1$-$C_4$alkyl)$_2$, —NR$_9$R$_{10}$, —NHCOR$_9$, or by a group of formula IV $$-R_{11}-\text{[phenyl]}-\overset{O}{\underset{\|}{C}}-\overset{R_1}{\underset{R_2}{C}}-\overset{R_3}{\underset{R_4}{N}} \quad (IV);$$

or Ar$_2$ is a group of formula Va or VIa

[structure Va: bicyclic with G, L, E]

(Va)

[structure VIa: tricyclic with R$_{11}$, R$_{12}$]

(VIa)

G is unbranched or branched $C_1$-$C_7$alkylene;

L and E independently of one another are a direct bond, —O—, —S— or —N(R$_6$)—, provided that L and E are not both a direct bond simultaneously;

$R_1$ and $R_2$ independently of one another are R$_7$O—, $C_1$-$C_8$alkyl, which is unsubstituted or substituted by OH, $C_1$-$C_4$alkoxy, SR$_8$, CN, ($C_1$-$C_8$alkyl)O(CO)—, ($C_1$-$C_4$alkyl)-(OC)O— or —N(R$_3$)(R$_4$), or $R_1$ and $R_2$ independently of one another are $C_3$-$C_6$alkenyl, phenyl, chlorophenyl, R$_7$—O-phenyl, R$_8$—S-phenyl or phenyl-$C_1$-$C_3$-alkyl, or $R_1$ and $R_2$ together are unbranched or branched $C_2$-$C_9$alkylene, $C_3$-$C_9$oxaalkylene or $C_3$-$C_9$azaalkylene, or $R_1$ and $R_2$ independently of one another are a radical of formula VII or VIII

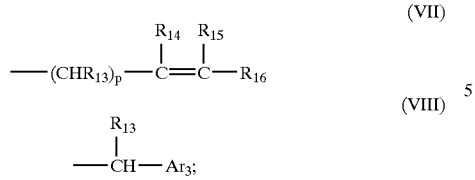  (VII)

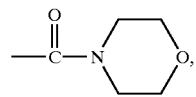

(VIII)

p is 0 or 1;
Ar$_3$ is phenyl, naphthyl, furyl, thienyl or pyridiyl, each of which is unsubstituted or substituted by halogen, SH, OH, C$_1$–C$_{12}$alkyl, OH-substituted C$_1$–C$_4$alkyl, halogen-substituted C$_1$–C$_4$alkyl, SH-substituted C$_1$–C$_4$alkyl, N(R$_{17}$)$_2$-substituted C$_1$–C$_4$alkyl, C$_1$–C$_{12}$alkoxy-substituted C$_1$–C$_4$alkyl, (C$_1$–C$_{18}$alkyl)O(OC)-substituted C$_1$–C$_4$alkyl, CH$_3$O(CH$_2$CH$_2$O)$_m$CO-substituted C$_1$–C$_4$alkyl, (C$_1$–C$_4$alkyl)(OC)O-substituted C$_1$–C$_4$alkyl, C$_1$–C$_{12}$alkoxy, (C$_1$–C$_{18}$alkyl)(OC)O-substituted C$_1$–C$_4$alkoxy, CH$_3$O(CH$_2$CH$_2$O)$_m$CO-substituted C$_1$–C$_4$alkoxy, —(OCH$_2$CH$_2$)$_m$OH, —(OCH$_2$CH$_2$)$_m$OCH$_3$, C$_1$–C$_8$alkylthio, phenoxy, —COO(C$_1$–C$_{18}$alkyl), —CO(OCH$_2$CH$_2$)$_m$OCH$_3$, phenyl or benzoyl;

m is 1 to 20;

R$_3$ is hydrogen, C$_1$–C$_{12}$alkyl, C$_2$–C$_4$alkyl, which is substituted by OH, SH, C$_1$–C$_4$alkoxy, CN or —COO(C$_1$–C$_4$alkyl); or R$_3$ is C$_3$–C$_5$alkenyl, C$_5$–C$_{12}$-cycloalkyl or phenyl-C$_1$–C$_3$alkyl;

R$_4$ is C$_1$–C$_{12}$alkyl; C$_2$–C$_4$alkyl, which is substituted by OH, SH, C$_1$–C$_4$alkoxy, CN or —COO(C$_1$–C$_4$alkyl); or R$_4$ is C$_3$–C$_5$alkenyl, C$_5$–C$_{12}$-cycloalkyl, phenyl-C$_1$–C$_3$alkyl; phenyl which is unsubstituted or substituted by halogen, C$_1$–C$_{12}$alkyl, C$_1$–C$_4$alkoxy or —COO(C$_1$–C$_4$alkyl);

or R$_4$ together with R$_2$ is C$_1$–C$_7$alkylene, phenyl-C$_1$–C$_4$alkylene, o-xylylene, 2-butenylene, C$_2$–C$_3$oxaalkylene or C$_2$–C$_3$azaalkylene;

or R$_3$ and R$_4$ together are C$_3$–C$_7$alkylene, optionally interrupted by —O—, —S—, —CO— or —N(R$_6$)— and which C$_3$–C$_7$alkylene is unsubstituted or substituted by OH, SH, C$_1$–C$_4$alkoxy or —COO(C$_1$–C$_4$alkyl);

R$_6$ is hydrogen, C$_1$–C$_{12}$alkyl, OH-substituted C$_1$–C$_{12}$alkyl, SH-substituted C$_1$–C$_{12}$alkyl or HS—(CH$_2$)$_n$—COO-substituted C$_1$–C$_{12}$alkyl; C$_2$–C$_{12}$alkyl, which is interrupted by —O—, —NH— or —S—;

or R$_6$ is C$_3$–C$_5$alkenyl, phenyl-C$_1$–C$_3$-alkyl, —CH$_2$CH$_2$CN, C$_1$–C$_4$alkyl-CO—CH$_2$CH$_2$—, OH-substituted C$_1$–C$_4$alkyl-CO—CH$_2$CH$_2$—, SH-substituted C$_1$–C$_4$alkyl-CO—CH$_2$CH$_2$—, C$_2$–C$_8$alkanoyl, OH-substituted C$_2$–C$_8$alkanoyl, SH-substituted C$_2$–C$_8$alkanoyl or benzoyl;

R$_7$ is hydrogen, C$_1$–C$_{12}$alkyl, C$_3$–C$_{12}$-alkenyl, cyclohexyl, hydroxycyclohexyl; C$_1$–C$_4$alkyl, which is mono- or polysubstituted by Cl, Br, CN, SH, —N(C$_1$–C$_4$alkyl)$_2$, piperidinyl, morpholinyl, OH, C$_1$–C$_4$alkoxy, —OCH$_2$CH$_2$CN, —OCH$_2$CH$_2$COO(C$_1$–C$_4$alkyl), —O(CO)R$_{19}$, —COOH, —COO(C$_1$–C$_8$alkyl), —CONH(C$_1$–C$_4$alkyl), —CON(C$_1$–C$_4$alkyl)$_2$,

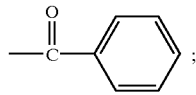

—CO(C$_1$–C$_4$alkyl) or by

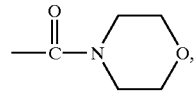

or R$_7$ is 2,3-epoxypropyl, —(CH$_2$CH$_2$O)$_n$H; phenyl which is unsubstituted or substituted by halogen, C$_1$–C$_4$alkyl, C$_1$–C$_4$alkoxy or —COO(C$_1$–C$_4$alkyl); or R$_7$ is phenyl-C$_1$–C$_3$-alkyl, tetrahydropyranyl, tetrahydrofuranyl, —COOR$_{19}$, —COO(C$_1$–C$_8$alkyl), —CONH(C$_1$–C$_4$alkyl), —CON(C$_1$–C$_8$alkyl)$_2$, —Si(R$_{20}$)(R$_{21}$)$_2$, or —SO$_2$R$_{22}$;

R$_8$ is hydrogen, C$_1$–C$_{12}$alkyl, C$_3$–C$_{12}$alkenyl, cyclohexyl, hydroxycyclohexyl; C$_1$–C$_4$alkyl, which is mono- or polysubstituted by Cl, Br, CN, SH, —N(C$_1$–C$_4$alkyl)$_2$, piperidinyl, morpholinyl, OH, C$_1$–C$_4$alkoxy, —OCH$_2$CH$_2$CN, —OCH$_2$CH$_2$COO(C$_1$–C$_4$alkyl), —O(CO)R$_{19}$, —COOH, —COO(C$_1$–C$_8$alkyl), —CON(C$_1$–C$_4$alkyl)$_2$,

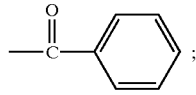

—CO(C$_1$–C$_4$alkyl) or

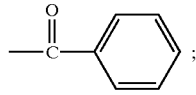

or R$_8$ is 2,3-epoxypropyl, phenyl-C$_1$–C$_3$alkyl, phenyl-C$_1$–C$_3$hydroxyalkyl; phenyl which is unsubstituted or mono- or poly-substituted by halogen, SH, C$_1$–C$_4$alkyl, C$_1$–C$_4$alkoxy or —COO(C$_1$–C$_4$alkyl); or R$_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

R$_9$ and R$_{10}$ independently of one another are hydrogen, C$_1$–C$_{12}$alkyl; C$_2$–C$_4$alkyl, which is substituted by OH, SH, C$_1$–C$_4$alkoxy, CN or —COO(C$_1$–C$_4$alkyl); or R$_9$ and R$_{10}$ independently of one another are C$_3$–C$_5$alkenyl, cyclohexyl, phenyl-C$_1$–C$_3$alkyl; phenyl which is unsubstituted or mono- or polysubstituted by C$_1$–C$_{12}$alkyl or halogen; or R$_9$ and R$_{10}$ together are C$_2$–C$_7$alkylene, optionally interrupted by —O—, —S— or —N(R$_6$)—, R$_{11}$ and R$_{12}$ independently of one another are a direct bond, —CH$_2$—, —CH$_2$CH$_2$—, —O—, —S—, —CO— or —N(R$_6$)—; provided that R$_{11}$ and R$_{12}$ are not a direct bond simultaneously;

R$_{13}$ is hydrogen, C$_1$–C$_8$alkyl or phenyl;

R$_{14}$, R$_{15}$ and R$_{16}$ independently of one another are hydrogen or C$_1$–C$_4$alkyl;

R$_{17}$ is hydrogen, C$_1$–C$_8$alkyl or phenyl;

R$_{19}$ is C$_1$–C$_4$alkyl, C$_2$–C$_4$alkenyl or phenyl;

R$_{20}$ and R$_{21}$ independently of one another are C$_1$–C$_4$alkyl or phenyl;

$R_{22}$ is $C_1$–$C_{18}$alkyl; or phenyl which is unsubstituted or substituted by $C_1$–$C_{14}$alkyl;

$A_1$ is a direct bond, —X[(CH$_2$)$_l$X']$_q$—[(C$_6$H$_4$)$_o$X"]$_r$—, —O—, —S— or —N(R$_6$)—;

X, X' and X" independently of each other are a direct bond, —O—, —S—, —N(R$_6$)—, —O(CO)—, —COO—, —NHCO—, —CONH— or —CO—;

l is an integer from 0 to 10;

q is an integer from 0 to 5;

o and r independently of one another are an integer 0, 1 or 2;

$CT_1$ is —Y'—, —$R_{25}$—,

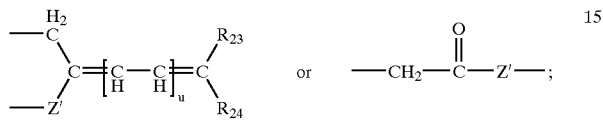

or —CH$_2$—C(=O)—Z'—;

Z' is —COOR$_{25}$—, —CONR$_9$R$_{25}$—, or —Ar$_2$—;

Y' is —W(R$_8$)$_t$—R$_{25}$—;

t is an integer 0, 1 or 2;

W is S, Si, Se, P, Br, Cl, Sn, —O—O—, S(=O), S(=O)$_2$, or P(=O);

$R_{23}$ and $R_{24}$ independently of one another are hydrogen, or $C_1$–$C_8$alkyl; or $R_{23}$ and $R_{24}$ together are $C_5$–$C_7$cyloalkyl; and p2 $R_{25}$ is a direct bond, $C_1$–$C_4$alkylene or phenylene.

u is 0 or 1; and

J and $J_1$ independently of one another are a polymeric group, provided that J and $J_1$ are not simultaneously the same groups.

14. Block copolymer according to claim 13 of formula XV wherein $Ar_2$ is

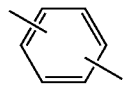

which is unsubstituted or substituted 1 to 4 times by halogen, $C_1$–$C_{12}$alkyl or —OR$_7$;

$R_7$ is hydrogen or $C_1$–$C_{12}$alkyl;

X, X' and X" independently of each other are a direct bond, —O—, —S— or —N(R$_6$)—;

$R_6$ is hydrogen or $C_1$–$C_{12}$alkyl;

l is an integer from 0 to 4;

q is an integer from 0 or 1;

o and r independently of one another are an integer 0, 1 or 2;

$CT_1$ is —Y'— or

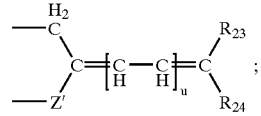

Z' is —COOR$_{25}$— or —CONR$_9$R$_{25}$—;

t and u are 0;

W is S;

$R_8$ and $R_9$ independently of one another are hydrogen or $C_1$–$C_{12}$alkyl;

$R_{23}$ and $R_{24}$ are hydrogen; and $R_{25}$ is a direct bond or $C_1$–$C_4$alkylene.

15. Process for preparing a block copolymer of formula XV

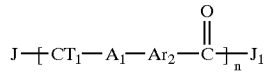

(XV), wherein n is 1 or 2;

$Ar_2$ is

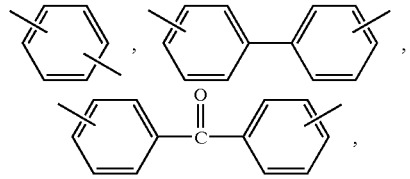

each of which is unsubstituted or substituted 1 to 5 times by halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SR$_8$, —SOR$_8$, —SO$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of formula IV

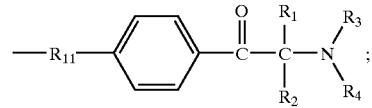

(IV)

or $Ar_2$ is a group of formula Va or VIa

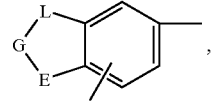

(Va)

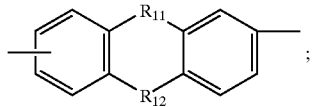

(VIa)

G is unbranched or branched $C_1$–$C_7$alkylene;

L and E independently of one another are a direct bond, —O—, —S— or —N(R$_6$)—, provided that L and E are not both a direct bond simultaneously;

$R_1$ and $R_2$ independently of one another are R$_7$O—, $C_1$–$C_8$alkyl, which is unsubstituted or substituted by OH, $C_1$–$C_4$alkoxy, SR$_8$, CN, ($C_1$–$C_8$alkyl)O(CO)—, ($C_1$–$C_4$alkyl)-(OC)O— or —N(R$_3$)(R$_4$), or $R_1$ and $R_2$ independently of one another are $C_3$–$C_6$alkenyl, phenyl, chlorophenyl, R$_7$—O-phenyl, R$_8$—S-phenyl or phenyl-$C_1$–$C_3$-alkyl, or $R_1$ and $R_2$ together are unbranched or branched $C_2$–$C_9$alkylene, $C_3$–$C_9$oxaalkylene or $C_3$–$C_9$azaalkylene, or $R_1$ and $R_2$ independently of one another are a radical of formula VII or VIII

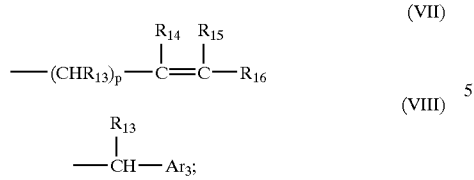

(VII)

(VIII)

p is 0 or 1;

Ar$_3$ is phenyl, naphthyl, furyl, thienyl or pyridiyl, each of which is unsubstituted or substituted by halogen, SH, OH, C$_1$–C$_{12}$alkyl, OH-substituted C$_1$–C$_4$alkyl, halogen-substituted C$_1$–C$_4$alkyl, SH-substituted C$_1$–C$_4$alkyl, N(R$_{17}$)$_2$-substituted C$_1$–C$_4$alkyl, C$_1$–C$_{12}$alkoxy-substituted C$_1$–C$_4$alkyl, (C$_1$–C$_{18}$alkyl)(OC)O-substituted C$_1$–C$_4$alkyl, C$_1$–C$_{12}$alkoxy, (C$_1$–C$_{18}$alkyl)(OC)O-substituted C$_1$–C$_4$alkoxy, CH$_3$O(CH$_2$CH$_2$O)$_m$CO-substituted C$_1$–C$_4$alkoxy, —(OCH$_2$CH$_2$)$_m$OH, —(OCH$_2$CH$_2$)$_m$OCH$_3$, C$_1$–C$_8$alkylthio, phenoxy, —COO(C$_1$–C$_{18}$alkyl), —CO(OCH$_2$CH$_2$)$_m$OCH$_3$, phenyl or benzoyl;

m is 1 to 20;

R$_3$ is hydrogen, C$_1$–C$_{12}$alkyl, C$_2$–C$_4$alkyl, which is substituted by OH, SH, C$_1$–C$_4$alkoxy, CN or —COO(C$_1$–C$_4$alkyl); or R$_3$ is C$_3$–C$_5$alkenyl, C$_5$–C$_{12}$-cycloalkyl or phenyl-C$_1$–C$_3$alkyl;

R$_4$ is C$_1$–C$_{12}$alkyl; C$_2$–C$_4$alkyl, which is substituted by OH, SH, C$_1$–C$_4$alkoxy, CN or —COO(C$_1$–C$_4$alkyl);

or R$_4$ is C$_3$–C$_5$alkenyl, C$_5$–C$_{12}$-cycloalkyl, phenyl-C$_1$–C$_3$alkyl; phenyl which is unsubstituted or substituted by halogen, C$_1$–C$_{12}$alkyl, C$_1$–C$_4$alkoxy or —COO(C$_1$–C$_4$alkyl);

or R$_4$ together with R$_2$ is C$_1$–C$_7$alkylene, phenyl-C$_1$–C$_4$alkylene, o-xylylene, 2-butenylene, C$_2$–C$_3$oxaalkylene or C$_2$–C$_3$azaalkylene;

or R$_3$ and R$_4$ together are C$_3$–C$_7$alkylene, optionally interrupted by —O—, —S—, —CO— or —N(R$_6$)— and which C$_3$–C$_7$alkylene is unsubstituted or substituted by OH, SH, C$_1$–C$_4$alkoxy or —COO(C$_1$–C$_4$alkyl);

R$_6$ is hydrogen, C$_1$–C$_{12}$alkyl, OH-substituted C$_1$–C$_{12}$alkyl, SH-substituted C$_1$–C$_{12}$alkyl or HS—(CH$_2$)$_n$—COO-substituted C$_1$–C$_{12}$alkyl; C$_2$–C$_{12}$alkyl, which is interrupted by —O—, —NH— or —S—; or R$_6$ is C$_3$–C$_5$alkenyl, phenyl-C$_1$–C$_3$-alkyl, —CH$_2$CH$_2$CN, C$_1$–C$_4$alkyl-CO—CH$_2$CH$_2$—, OH-substituted C$_1$–C$_4$alkyl-CO—CH$_2$CH$_2$—, SH-substituted C$_1$–C$_4$alkyl-CO—CH$_2$CH$_2$—, C$_2$–C$_8$alkanoyl, OH-substituted C$_2$–C$_8$alkanoyl, SH-substituted C$_2$–C$_8$alkanoyl or benzoyl;

R$_7$ is hydrogen, C$_1$–C$_{12}$alkyl, C$_3$–C$_{12}$-alkenyl, cyclohexyl, hydroxycyclohexyl; C$_1$–C$_4$alkyl, which is mono- or polysubstituted by Cl, Br, CN, SH, —N(C$_1$–C$_4$alkyl)$_2$, piperidinyl, morpholinyl, OH, C$_1$–C$_4$alkoxy, —OCH$_2$CH$_2$CN, —OCH$_2$CH$_2$COO(C$_1$–C$_4$alkyl), —O(CO)R$_{19}$, —COOH, —COO(C$_1$–C$_8$alkyl), —CONH(C$_1$–C$_4$alkyl), —CON(C$_1$–C$_4$alkyl)$_2$,

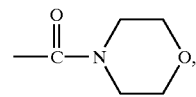

—CO(C$_1$–C$_4$alkyl) or by

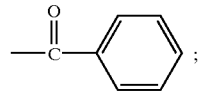

or R$_7$ is 2,3-epoxypropyl, —(CH$_2$CH$_2$O)$_n$H; phenyl which is unsubstituted or substituted by halogen, C$_1$–C$_4$alkyl, C$_1$–C$_4$alkoxy or —COO(C$_1$–C$_4$alkyl); or R$_7$ is phenyl-C$_1$–C$_3$alkyl, tetrahydropyranyl, tetrahydrofuranyl, —COOR$_{19}$, —COO(C$_1$–C$_8$alkyl), —CONH(C$_1$–C$_4$alkyl), —CON(C$_1$–C$_8$alkyl)$_2$, —Si(R$_{20}$)(R$_{21}$)$_2$, or —SO$_2$R$_{22}$;

R$_8$ is hydrogen, C$_1$–C$_{12}$alkyl, C$_3$–C$_{12}$alkenyl, cyclohexyl, hydroxycyclohexyl; C$_1$–C$_4$alkyl, which is mono- or polysubstituted by Cl, Br, CN, SH, —N(C$_1$–C$_4$alkyl)$_2$, piperidinyl, morpholinyl, OH, C$_1$–C$_4$alkoxy, —OCH$_2$CH$_2$CN, —OCH$_2$CH$_2$COO(C$_1$–C$_4$alkyl), —O(CO)R$_{19}$, —COOH, —COO(C$_1$–C$_8$alkyl), —CON(C$_1$–C$_4$alkyl)$_2$,

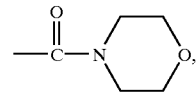

—CO(C$_1$–C$_4$alkyl) or

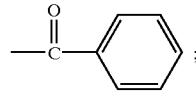

or R$_8$ is 2,3-epoxypropyl, phenyl-C$_1$–C$_3$alkyl, phenyl-C$_1$–C$_3$hydroxyalkyl; phenyl which is unsubstituted or mono- or poly-substituted by halogen, SH, C$_1$–C$_4$alkyl, C$_1$–C$_4$alkoxy or —COO(C$_1$–C$_4$alkyl); or R$_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

R$_9$ and R$_{10}$ independently of one another are hydrogen, C$_1$–C$_{12}$alkyl; C$_2$–C$_4$alkyl, which is substituted by OH, SH, C$_1$–C$_4$alkoxy, CN or —COO(C$_1$–C$_4$alkyl); or R$_9$ and R$_{10}$ independently of one another are C$_3$–C$_5$alkenyl, cyclohexyl, phenyl-C$_1$–C$_3$alkyl; phenyl which is unsubstituted or mono- or poly-substituted by C$_1$–C$_{12}$alkyl or halogen; or R$_9$ and R$_{10}$ together are C$_2$–C$_7$alkylene, optionally interrupted by —O—,—S— or —N(R$_6$)—;

R$_{11}$ and R$_{12}$ independently of one another are a direct bond, —CH$_2$—, —CH$_2$CH$_2$—, —O—, —S—, —CO— or —N(R$_6$)—; provided that R$_{11}$ and R$_{12}$ are not a direct bond simultaneously;

R$_{13}$ is hydrogen, C$_1$–C$_8$alkyl or phenyl;

R$_{14}$, R$_{15}$ and R$_{16}$ independently of one another are hydrogen or C$_1$–C$_4$alkyl;

R$_{17}$ is hydrogen, C$_1$–C$_8$alkyl or phenyl;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl; or phenyl which is unsubstituted or substituted by $C_1$–$C_{14}$alkyl;

$A_1$ is a direct bond, —X[(CH$_2$)$_l$X']$_q$—[(C$_6$H$_4$)$_o$X'']$_r$—, —O—, —S— or —N(R$_6$)—;

X, X' and X'' independently of each other are a direct bond, —O—, —S—, —N(R$_6$)—, —O(CO)—, —COO—, —NHCO—, —CONH— or —CO—;

l is an integer from 0 to 10;

q is an integer from 0 to 5;

o and r independently of one another are an integer 0, 1 or 2;

$CT_1$ is —Y'—, —$R_{25}$—,

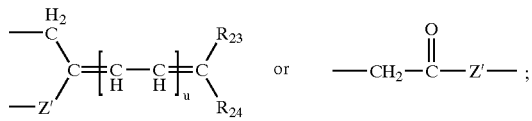

Z' is —COOR$_{25}$—, —CONR$_9$R$_{25}$—, or —Ar$_2$—;

Y' is —W(R$_8$)$_t$—R$_{25}$—;

t is an integer 0, 1 or 2;

W is S, Si, Se, P, Br, Cl, Sn, —O—O—, S(=O), S(=O)$_2$, or P(=O);

$R_{23}$ and $R_{24}$ independently of one another are hydrogen, or $C_1$–$C_8$alkyl; or $R_{23}$ and $R_{24}$ together are $C_5$–$C_7$cyloalkyl; and $R_{25}$ is a direct bond, $C_1$–$C_4$alkylene or phenylene u is 0 or 1; and J and $J_1$ independently of one another are a polymeric group, provided that J and $J_1$ are not simultaneously the same groups, characterized in that a macrophotoinitiator obtained by thermally polymerizing a monomer and a photoinitiator compound of formula Ia or Ib according to claim 1 and at least one radically polymerizable monomer are mixed and irradiated with light.

* * * * *